US009657276B2

(12) United States Patent
Philippe et al.

(10) Patent No.: US 9,657,276 B2
(45) Date of Patent: May 23, 2017

(54) NEUROVIRULENT STRAIN OF THE WEST NILE VIRUS AND USES THEREOF

(71) Applicants: Despres Philippe, La Garenne-colombes (FR); Vincent Deubel, Vanves (FR); Jean-Louis Guenet, Longjumeau (FR); Marie-Therese Drouet, Paris (FR); Mertyn Malkinson, Beit Dagan (IL); Caroline Banet, Beit Dagan (IL); Marie-Pascale Frenkiel, Levallois (FR); Marie-Pierre Courageot, Paris (FR); Fasseli Coulibaly, Paris (FR); Adeline Catteau, Savigny Sur Orge (FR); Marie Flamand, Paris (FR); Patrick Weber, Montreuil (FR); Pierre-Emmanuel Ceccaldi, Boissise-la-bertrand (FR)

(72) Inventors: Despres Philippe, La Garenne-colombes (FR); Vincent Deubel, Vanves (FR); Jean-Louis Guenet, Longjumeau (FR); Marie-Therese Drouet, Paris (FR); Mertyn Malkinson, Beit Dagan (IL); Caroline Banet, Beit Dagan (IL); Marie-Pascale Frenkiel, Levallois (FR); Marie-Pierre Courageot, Paris (FR); Fasseli Coulibaly, Paris (FR); Adeline Catteau, Savigny Sur Orge (FR); Marie Flamand, Paris (FR); Patrick Weber, Montreuil (FR); Pierre-Emmanuel Ceccaldi, Boissise-la-bertrand (FR)

(73) Assignees: Institut Pasteur, Paris (FR); Kimron Veterinary Institute, Beit Dagan (IL)

( * ) Notice: Subject to any disclaimer, the term of this patent is extended or adjusted under 35 U.S.C. 154(b) by 0 days.

(21) Appl. No.: 14/230,776

(22) Filed: Mar. 31, 2014

(65) Prior Publication Data
US 2014/0237631 A1    Aug. 21, 2014

Related U.S. Application Data

(60) Continuation of application No. 13/423,161, filed on Mar. 16, 2012, now Pat. No. 8,715,693, which is a continuation of application No. 12/112,366, filed on Apr. 30, 2008, now abandoned, which is a division of application No. 10/956,085, filed on Oct. 4, 2004, now Pat. No. 7,390,495.

(51) Int. Cl.
| | | |
|---|---|---|
| *C12N 7/00* | (2006.01) | |
| *C07K 14/005* | (2006.01) | |
| *A61K 39/00* | (2006.01) | |
| *A01K 67/027* | (2006.01) | |
| *C12Q 1/70* | (2006.01) | |
| *G01N 33/569* | (2006.01) | |

(52) U.S. Cl.
CPC .............. *C12N 7/00* (2013.01); *A01K 67/027* (2013.01); *C07K 14/005* (2013.01); *C12Q 1/701* (2013.01); *G01N 33/56983* (2013.01); *A01K 2267/02* (2013.01); *A61K 39/00* (2013.01); *C12N 2770/24121* (2013.01)

(58) Field of Classification Search
None
See application file for complete search history.

(56) References Cited

U.S. PATENT DOCUMENTS 7,390,495 B2    6/2008    Despres et al.
8,715,693 B2    5/2014    Despres et al.

OTHER PUBLICATIONS

Tardei et al., Evaluation of Immunoglobulin M (IgM) and IgG Enzyme Immunoassays in Serologic Diagnosis of West Nile Virus Infection, 2000, Journal of Clinical Microbiology, vol. 38, No. 6, pp. 2232-2239.*
Le Cann et al., Detection of Antibodies to L1, L2, and E4 Proteins of Human Papillomavirus Types 6, 11, and 16 by ELISA Using Synthetic Peptides, 1995, Journal of Medical Virology, vol. 45, pp. 410-414.*
Fiona, J. May et al., "Phylogeography of West Nile Virus: From the Cradle of Evolution in Africa to Eurasia, Australia, and the Americas", Journal of Virology, Mar. 2011, (pp. 2964-2974).
Odelola and Oduye, West Nile Virus Infection of Adult Mice by Oral Route Brief Report, 1977, Archives of Virology, vol. 54, pp. 251-253.
Rodhain et al. Arboviruses and Lemurs in Madagascar: Experimental Infection of Lemur Ful Vus With Yellow Fever and West Nile Viruses, 1985, American Journal of Tropical Medicine and Hygiene, vol. 34, No. 4, pp. 816-822.
GenBank Accession # GQ851607, West Nile virus strain IBAN7019 polyprotein gene, complete cds, 2010.
GenBank Accession #ADM88866, polyprotein [West Nile virus], 2010.
GenBank Accession #EU081844, West Nile virus strain Egypt 101, complete genome, 2007.
GenBank Accession #ABU52997, polyprotein [West Nile virus], 2007.
X-Y Jia, et al.: "Genetic analysis of West Nile New York 1999 encephalitis virus" LANCET, XX, XX, vol. 354, No. 9194, pp. 1971-1972, Dec. 4, 1999.
RS Lanciotti, et al., "Origin of the West Nile virus responsible for an out break of encephalitis in the northeastern United States" Science (Washington DC), vol. 286, No. 5448, pp. 2333-2337, Dec. 17, 1999.
John F. Anderson, et al., "Isolation of West Nile virus from mosquitoes, crows, and a Cooper's hawk in Connecticut" Science (Washington DC), vol. 286, No. 5448, pp. 2331-2333, Dec. 17, 1999.

(Continued)

*Primary Examiner* — Benjamin P Blumel
(74) *Attorney, Agent, or Firm* — Arrigo, Lee & Guttman LLP

(57) ABSTRACT

Neuroinvasive and neurovirulent strain of the West Nile virus, named IS-98-ST1, nucleic acid molecules derived from its genome, proteins and peptides encoded by said nucleic acid molecules, and uses thereof.

13 Claims, 13 Drawing Sheets

(56) References Cited

OTHER PUBLICATIONS

Figure 2:
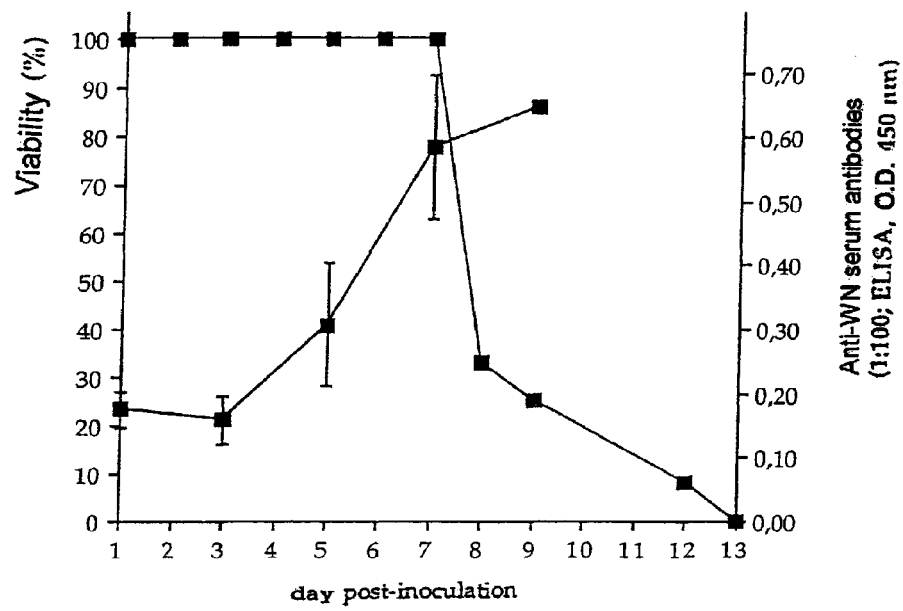

G. Wengler, et al., "An analysis of the antibody response against West Nile virus E protein purified by SDS-page indicates that this protein does not contain sequential epitopes for efficient induction of neutralizingantibodies," Journal of General Virology, vol. 70, No. 4, pp. 987-992, 1989.

Urosevic, et al., Molecular characterization of virus-specific RNA produced in the brains of flavivirus-susceptible and -resistant mice after challenge with Murray Valley encephalitis virus, 1997, Journal of General Virology, vol. 78, pp. 23-29.

Platonov, et al., Outbreak of West Nile Virus Infection, Volgograd Region, Russia, 2001, Emerging Infectious Diseases, vol. 7, No. 1, pp. 128-132.

Malkinson, et al., Introduction of West Nile Virus in the Middle East by Migrating White Storks, 2002, Emerging Infectious Diseases, vol. 8, No. 4, pp. 392-397.

GenBank Accession# AAF20205, polyprotein precursor [West Nile virus], May 8

```
                    C
CI      MSKKPGGPGKSRAVNMLKRGMPRVLSLIGLKRAMLSLIDGKGPIRFVLAL
FLA     MSKKPGGPGKSRAVNMLKRGMPRVLSLIGLKRAMLSLIDGKGPIRFVLAL
        **************************************************

CI      LAFFRFTAIAPTRAVLDRWRGVNKQTAMKHLLSFKKELGTLTSAINRRSS
FLA     LAFFRFTAIAPTRAVLDRWRGVNKQTAMKHLLSFKKELGTLTSAINRRSS
        **************************************************
                                prM
CI      KQKKRGGKTGIAVMIGLIASVGAVTLSNFQGKVMMTVNATDVTDVITIPT
FLA     KQKKRGGKTGIAVMIGLIASVGAVTLSNFQGKVMMTVNATDVTDVITIPT
        **************************************************

CI      AAGKNLCIVRAMDVGYMCDDTITYECPVLSAGNDPEDIDCWCTKSAVYVR
FLA     AAGKNLCIVRAMDVGYMCDDTITYECPVLSAGNDPEDIDCWCTKSAVYVR
        **************************************************
                        M
CI      YGRCTKTRHSRRSRRSLTVQTHGESTLANKKGAWMDSTKATRYLVKTESW
FLA     YGRCTKTRHSRRSRRSLTVQTHGESTLANKKGAWMDSTKATRYLVKTESW
        **************************************************
                                                        E
CI      ILRNPGYALVAAVIGWMLGSNTMQRVVFVVLLLLVAPAYSFNCLGMSNRD
FLA     ILRNPGYALVAAVIGWMLGSNTMQRVVFVVLLLLVAPAYSFNCLGMSNRD
        **************************************************

CI      FLEGVSGATWVDLVLEGDSCVTIMSKDKPTIDVKMMNMEAANLAEVRSYC
FLA     FLEGVSGATWVDLVLEGDSCVTIMSKDKPTIDVKMMNMEAVNLAEVRSYC
        **************************************** *********

CI      YLATVSDLSTKAACPTMGEAHNDKRADPAFVCRQGVVDRGWGNGCGLFGK
FLA     YLATVSDLSTKAACPTMGEAHNDKRADPAFVCRQGVVDRGWGNGCGLFGK
        **************************************************

CI      GSIDTCAKFACSTKAIGRTILKENIKYEVAIFVHGPTTVESHGNYSTQVG
FLA     GSIDTCAKFACSTKAIGRTILKENIKYEVAIFVHGPTTVESHGNYSTQVG
        **************************************************

CI      ATQAGRFSITPAAPSYTLKLGEYGEVTVDCEPRSGIDTNAYYVMTVGTKT
FLA     ATQAGRFSITPAAPSYTLKLGEYGEVTVDCEPRSGIDTNAYYVMTVGTKT
        **************************************************

CI      FLVHREWFMDLNLPWSSAGSTVWRNRETLMEFEEPHATKQSVIALGSQEG
FLA     FLVHREWFMDLNLPWSSAGSTVWRNRETLMEFEEPHATKQSVIALGSQEG
        **************************************************

CI      ALHQALAGAIPVEFSSNTVKLTSGHLKCRVKMEKLQLKGTTYGVCSKAFK
FLA     ALHQALAGAIPVEFSSNTVKLTSGHLKCRVKMEKLQLKGTTYGVCSKAFK
        **************************************************

CI      FLGTPADTGHGTVVLELQYTGTDGPCKVPISSVASLNDLTPVGRLVTVNP
FLA     FLGTPADTGHGTVVLELQYTGTDGPCKVPISSVASLNDLTPVGRLVTVNP
        **************************************************

CI      FVSVATANAKVLIELEPPFGDSYIVVGRGEQQINHHWHKSGSSIGKAFTT
FLA     FVSVATANAKVLIELEPPFGDSYIVVGRGEQQINHHWHKSGSSIGKAFTT
        **************************************************
```

*FIG. 1A*

| | |
|---|---|
| CI | TLKGAQRLAALGDTAWDFGSVGGVFTSVGKAVHQVFGGAFRSLFGGMSWI |
| FLA | TLKGAQRLAALGDTAWDFGSVGGVFTSVGKAVHQVFGGAFRSLFGGMSWI |
| | ************************************************* |

NS1

| | |
|---|---|
| CI | TQGLLGALLLWMGINARDRSIALTFLAVGGVLLFLSVNVHADTGCAIDIS |
| FLA | TQGLLGALLLWMGINARDRSIALTFLAVGGVLLFLSVNVHADTGCAIDIS |
| | ************************************************* |
| CI | RQELRCGNGVFIHNDVEAWMDRYKYYPETPQGLAKIIQKAHKEGVCGLRS |
| FLA | RQELRCGSGVFIHNDVEAWMDRYKYYPETPQGLAKIIQKAHKEGVCGLRS |
| | ******* ****************************************** |
| CI | VSRLEHQMWEAVKDELNTLLKENGVDLSVVVEKQEGMYKSAPKRLTATTE |
| FLA | VSRLEHQMWEAVKDELNTLLKENGVDLSVVVEKQEGMYKSAPKRLTATTE |
| | ************************************************* |
| CI | KLEIGWKAWGKSILFAPELANNTFVVDGPETKECPTQNRAWNSLEVEDFG |
| FLA | KLEIGWKAWGKSILFAPELANNTFVVDGPETKECPTQNRAWNSLEVEDFG |
| | ************************************************* |
| CI | FGLTSTRMFLKVRESNTTECDSKIIGTAVKNNLAIHSDLSYWIESRLNDT |
| FLA | FGLTSTRMFLKVRESNTTECDSKIIGTAVKNNLAIHSDLSYWIESRLNDT |
| | ************************************************* |
| CI | WKLERAVLGEVKSCTWPETHTLWGDGILESDLIIPVTLAGPRSNHNRRPG |
| FLA | WKLERAVLGEVKSCTWPETHTLWGDGILESDLIIPVTLAGPRSNHNRRPG |
| | ************************************************* |
| CI | YKTQNQGPWDEGRVEIDFDYCPGTTVTLSESCGHRGPATRTTTESGKLIT |
| FLA | YKTQNQGPWDEGRVEIDFDYCPGTTVTLSESCGHRGPATRTTTESGKLIT |
| | ************************************************* |

NS2A

| | |
|---|---|
| CI | DWCCRSCTLPPLRYQTDSGCWYGMEIRPQRHDEKTLVQSQVNAYNADMID |
| FLA | DWCCRSCTLPPLRYQTDSGCWYGMEIRPQRHDEKTLVQSQVNAYNADMID |
| | ************************************************* |
| CI | PFQLGLLVVFLATQEVLRKRWTAKISMPAILIALLVLVFGGITYTDVLRY |
| FLA | PFQLGLLVVFLATQEVLRKRWTAKISMPAILIALLVLVFGGITYTDVLRY |
| | ************************************************* |
| CI | VILVGAAFAESNSGGDVVHLALMATFKIQPVFMVASFLKARWTNQENILL |
| FLA | VILVGAAFAESNSGGDVVHLALMATFKIQPVFMVASFLKARWTNQENILL |
| | ************************************************* |
| CI | MLAAVFFQMAYHDARQILLWEIPDVLNSLAVAWMILRAITFTTTSNVVVP |
| FLA | MLAAVFFQMAYHDARQILLWEIPDVLNSLAVAWMILRAITFTTTSNVVVP |
| | ************************************************* |
| CI | LLALLTPRLRCLNLDVYRILLLMVGIGSLIREKRSAAAKKKGASLLCLAL |
| FLA | LLALLTPGLRCLNLDVYRILLLMVGIGSLIREKRSAAAKKKGASLLCLAL |
| | ******* ****************************************** |

NS2B

| | |
|---|---|
| CI | ASTGLFNPMILAAGLIACDPNRKRGWPATEVMTAVGLMFAIVGGLAELDI |
| FLA | ASTGLFNPMILAAGLIACDPNRKRGWPATEVMTAVGLMFAIVGGLAELDI |
| | ************************************************* |
| CI | DSMAIPMTIAGLMFAAFVISGKSTDMWIERTADISWESDAEITGSSERVD |
| FLA | DSMAIPMTIAGLMFAAFVISGKSTDMWIERTADISWESDAEITGSSERVD |
| | ************************************************* |
| CI | VRLDDGENFQLMNDPGAPWKIWMLRMVCLAISAYTPWAILPSVVGFWITL |

FIG. 1B

```
FLA    VRLDDDGNFQLMNDPGAPWKIWMLRMVCLAISAYTPWAILPSVVGFWITL
       *****  ******************************************
              NS3
CI     QYTKRGGVLWDTPSPKEYKKGDTTTGVYRIMTRGLLGSYQAGAGVMVEGV
FLA    QYTKRGGVLWDTPSPKEYKKGDTTTGVYRIMTRGLLGSYQAGAGVMVEGV
       **************************************************

CI     FHTLWHTTKGAALMSGEGRLDPYWGSVKEDRLCYGGPWKLQHKWNGQDEV
FLA    FHTLWHTTKGAALMSGEGRLDPYWGSVKEDRLCYGGPWKLQHKWNGQDEV
       **************************************************

CI     QMIVVEPGKNVKNVQTKPGVFKTPEGEIGAVTLDFPTGTSGSPIVDKNGD
FLA    QMIVVEPGKNVKNVQTKPGVFKTPEGEIGAVTLDFPTGTSGSPIVDKNGD
       **************************************************

CI     VIGLYGNGVIMPNGSYISAIVQGERMDEPIPAGFEPEMLRKKQITVLDLH
FLA    VIGLYGNGVIMPNGSYISAIVQGERMDEPIPAGFEPEMLRKKQITVLDLH
       **************************************************

CI     PGAGKTRRILPQIIKEAINRRLRTAVLAPTRVVAAEMAEALRGLPIRYQT
FLA    PGAGKTRRILPQIIKEAINRRLRTAVLAPTRVVAAEMAEALRGLPIRYQT
       **************************************************

CI     SAVPREHNGNEIVDVMCHATLTHRLMSPHRVPNYNLFVMDEAHFTDPASI
FLA    SAVPREHNGNEIVDVMCHATLTHRLMSPHRVPNYNLFVMDEAHFTDPASI
       **************************************************

CI     AARGYISTKVELGEAAAIFMTATPPGTSDPFPESNSPISDLQTEIPDRAW
FLA    AARGYISTKVELGEAAAIFMTATPPGTSDPFPESNSPISDLQTEIPDRAW
       **************************************************

CI     NSGYEWITEYTGKTVWFVPSVKMGNEIALCLQRAGKKVVQLNRKSYETEY
FLA    NSGYEWITEYTGKTVWFVPSVKMGNEIALCLQRAGKKVVQLNRKSYETEY
       **************************************************

CI     PKCKNDDWDFVITTDISEMGANFKASRVIDSRKSVKPTIITEGEGRVILG
FLA    PKCKNDDWDFVITTDISEMGANFKASRVIDSRKSVKPTIITEGEGRVILG
       **************************************************

CI     EPSAVTAASAAQRRGRIGRNPSQVGDEYCYGGHTNEDDSNFAHWTEARIM
FLA    EPSAVTAASAAQRRGRIGRNPSQVGDEYCYGGHTNEDDSNFAHWTEARIM
       **************************************************

CI     PDNINMPNGLIAQFYQPEREKVYTMEGEYRLRGEERKNFLELLRTADLPV
FLA    LDNINMPNGLIAQFYQPEREKVYTMDGEYRLRGEERKNFLELLRTADLPV
        ************************ *************************

CI     WLAYKVAAAGVSYHDRRWCFDGPRTNTILEDNNEVEVITKLGERKILRPR
FLA    WLAYKVAAAGVSYHDRRWCFDGPRTNTILEDNNEVEVITKLGERKILRPR
       **************************************************
                                                     NS4A
CI     WIDARVYSDHQALKAFKDFASGKRSQIGLIEVLGKMPEHFMGKTWEALDT
FLA    WIDARVYSDHQALKAFKDFASGKRSQIGLIEVLGKMPEHFMGKTWEALDT
       **************************************************

CI     MYVVATAEKGGRAHRMALEELPDALQTIALIALLSVMTGVFFLLMQRKG
FLA    MYVVATAEKGGRAHRMALEELPDALQTIALIALLSVMTGVFFLLMQRKG
       *************************************************

CI     IGKIGLGGAVLGVATFFCWMAEVPGTKIAGMLLLSLLLMIVLIPEPEKQR
```

*FIG. 1C*

| | |
|---|---|
| FLA | IGKIGLGGAVLGVATFFCWMAEVPGTKIAGMLLLSLLLMIVLIPEPEKQR |
| | ************************************************** |
| | NS4B |
| CI | SQTDNQLAVFLICVMTLVSAVAANEMGWLDKTKSDISSLFGQRIEVKENF |
| FLA | SQTDNQLAVFLICVMTLVSAVAANEMGWLDKTKSDISSLFGQRIEVKENF |
| | ************************************************** |
| CI | SMGEFLLDLRPATAWSLYAVTTAVLTPLLKHLITSDYINTSLTSINVQAS |
| FLA | SMGEFLLDLRPATAWSLYAVTTAVLTPLLKHLITSDYINTSLTSINVQAS |
| | ************************************************** |
| CI | ALFTLARGFPFVDVGVSALLLAAGCWGQVTLTVTVTAATLLFCHYAYMVP |
| FLA | ALFTLARGFPFVDVGVSALLLAAGCWGQVTLTVTVTAATLLFCHYAYMVP |
| | ************************************************** |
| CI | GWQAEAMRSAQRRTAAGIMKNAVVDGIVATDVPELERTTPIMQKKVGQIM |
| FLA | GWQAEAMRSAQRRTAAGIMKNAVVDGIVATDVPELERTTPIMQKKVGQIM |
| | ************************************************** |
| CI | LILVSLAAVVVNPSVKTVREAGILITAAAVTLWENGASSVWNATTAIGLC |
| FLA | LILVSLAAVVVNPSVKTVREAGILITAAAVTLWENGASSVWNATTAIGLC |
| | ************************************************** |
| | NS5 |
| CI | HIMRGGWLSCLSITWTLIKNMEKPGLKRGGAKGRTLGEVVWKERLNQMTKE |
| FLA | HIMRGGWLSCLSITWTLIKNMEKPGLKRGGAKGRTLGEVVWKERLNQMTKE |
| | ************************************************** |
| CI | EFTRYRKEAIIEVDRSAAKHARKEGNVTGGHSVSRGTAKLRWLVERRFLE |
| FLA | EFTRYRKEAIIEVDRSAAKHARKEGNVTGGHPVSRGTAKLRWLVERRFLE |
| | ****************************** . ****************** |
| CI | PVGKVIDLGCGRGGWCYYMATQKRVQEVRGYTKGGPGHEEPQLVQSYGWN |
| FLA | PVGKVIDLGCGRGGWCYYMATQKRVQEVRGYTKGGPGHEEPQLVQSYGWN |
| | ************************************************** |
| CI | IVTMKSGVDVFYRPSECCDTLLCDIGESSSSAEVEEHRTIRVLEMVEDWL |
| FLA | IVTMKSGVDVFYRPSECCDTLLCDIGESSSSAEVEEHRTIRVLEMVEDWL |
| | ************************************************** |
| CI | HRGPREFCVKVLCPYMPKVIEKMELLQRRYGGGLVRNPLSRNSTHEMYWV |
| FLA | HRGPREFCVKVLCPYMPKVIEKMELLQRRYGGGLVRNPLSRNSTHEMYWV |
| | ************************************************** |
| CI | SRASGNVVHSVNMTSQVLLGRMEKRTWKGPQYEEDVNLGSGTRAVGKPLL |
| FLA | SRASGNVVHSVNMTSQVLLGRMEKRTWKGPQYEEDVNLGSGTRAVGKPLL |
| | ************************************************** |
| CI | NSDTSKINNRIERLRREYSSTWHHDENHPYRTWNYHGSYDVKPTGSASSL |
| FLA | NSDTSKIKNRIERLRREYSSTWHHDENHPYRTWNYHGSYDVKPTGSASSL |
| | ****** . ****************************************** |
| CI | VNGVVRLLSKPWDTITNVTTMAMTDTTPFGQQRVFKEKVDTKAPEPPEGA |
| FLA | VNGVVRLLSKPWDTITNVTTMAMTDTTPFGQQRVFKEKVDTKAPEPPEGV |
| | ************************************************ * |
| CI | KYVLNETTNWLWAFLAREKRPRMCSREEFIRKVNSNAALGAMFEEQNQWR |
| FLA | KYVLNETTNWLWAFLAREKRPRMCSREEFIRKVNSNAALGAMFEEQNQWR |
| | ************************************************** |
| CI | SAREAVEDPKFWEMVDEEREAHLRGECHTCIYNMMGKREKKPGEFGKAKG |

*FIG. 1D*

| | |
|---|---|
| FLA | SAREAVEDPKFWEMVDEEREAHLRGECHTCIYNMMGKREKKPGEFGKAKG |
| | ************************************************** |
| CI | SRAIWFMWLGARFLEFEALGFLNEDHWLGRKNSGGGVEGLGLQKLGYILR |
| FLA | SRAIWFMWLGARFLEFEALGFLNEDHWLGRKNSGGGVEGLGLQKLGYILR |
| | ************************************************** |
| CI | EVGTRPGGKIYADDTAGWDTRITRADLENEAKVLELLDGEHRRLARAIIE |
| FLA | EVGTRPGGKIYADDTAGWDTRITRADLENEAKVLELLDGEHRRLARAIIE |
| | ************************************************** |
| CI | LTYRHKVVKVMRPAADGRTVMDVISREDQRGSGQVVTYALNTFTNLAVQL |
| FLA | LTYRHKVVKVMRPAADGRTVMDVISREDQRGSGQVVTYALNTFTNLAVQL |
| | ************************************************** |
| CI | VRMMEGEGVIGPDDVEKLTKGKGPKVRTWLFENGEERLSRMAVSGDDCVV |
| FLA | VRMMEGEGVIGPDDVEKLTKGKGPKVRTWLFENGEERLSRMAVSGDDCVV |
| | ************************************************** |
| CI | KPLDDRFATSLHFLNAMSKVRKDIQEWKPSTGWYDWQQVPFCSNHFTELI |
| FLA | KPLDDRFATSLHFLNAMSKVRKDIQEWKPSTGWYDWQQVPFCSNHFTELI |
| | ************************************************** |
| CI | MKDGRTLVVPCRGQDELVGRARISPGAGWNVRDTACLAKSYAQMWLLLYF |
| FLA | MKDGRTLVVPCRGQDELVGRARISPGAGWNVRDTACLAKSYAQMWLLLYF |
| | ************************************************** |
| CI | HRRDLRLMANAICSAVPVNWVPTGRTTWSIHAGGEWMTTEDMLEVWNRVW |
| FLA | HRRDLRLMANAICSAVPVNWVPTGRTTWSIHAGGEWMTTEDMLEVWNRVW |
| | ************************************************** |
| CI | IEENEWMEDKTPVEKWSDVPYSGKREDIWCGSLIGTRARATWAENIQVAI |
| FLA | IEENEWMEDKTPVEKWSDVPYSGKREDIWCGSLIGTRARATWAENIQVAI |
| | ************************************************** |
| CI | NQVRAIIGDEKYVDYMSSLKRYEDTTLVEDTVL |
| FLA | NQVRAIIGDEKYVDYMSSLKRYEDTTLVEDTVL |
| | ********************************* |

*FIG. 1E*

Mice
Inbred laboratory mice:

BALB/c, C57BL/6, DDK, 129, C3H and DBA/1
    → sensitive to infection with the WN virus Wild mice:

SEG/Pas (*Mus spretus*), MAI/Pas, MBT/Pas (*Mus m. musculus*)
    → resistant to infection with the WN virus Virus
Injection of West Nile (WN

| Flv* Phenotype | Survivors | Deaths | Total |
|---|---|---|---|
| Resistant ($Flv^r/Flv^r$) | 108 | 0 | 108 (55%) |
| Sensitive ($Flv^s/Flv^s$) | 21 | 74 | 95 (45%) |
| Total | 129 (66%) | 74 (34%) | 203 |

\* one $Flv^r$ allele is sufficient to confer resistance

*FIG. 10*

NEUROVIRULENT STRAIN OF THE WEST NILE VIRUS AND USES THEREOF

This application is a continuation of application Ser. No. 13/423,161, filed Mar. 16, 2012, which is a continuation of application Ser. No. 12/112,366, filed Apr. 30, 2008 (abandoned), which is a divisional of application Ser. No. 10/956,085, filed Oct. 4, 2004 (now U.S. Pat. No. 7,390,495), which is a continuation of application Ser. No. 10/474,186 (abandoned), which is a National Stage Application of PCT/FR02/01168, filed Apr. 4, 2002, which claims priority to French Application No. 01/04599, filed Apr. 4, 2001, and French Application No. 01/11525, filed Sep. 6, 2001. The entire disclosure of each of the above listed applications for which priority is claimed are hereby incorporated herein by reference for all purposes.

The present invention relates to a neuroinvasive and neurovirulent strain of the West Nile virus, named IS-98-ST1, to nucleic acid molecules derived from its genome, to the proteins and peptides encoded by said nucleic acid molecules and to uses thereof.

The present invention also relates to all variants of the viral strain IS-98-ST1 which have at least one mutation in the nucleic acid sequence corresponding to NS5.

The family Flaviviridae includes the viruses of the flavivirus genus which are responsible for serious human pathological conditions such as dengue, yellow fever, tick-borne encephalitis, Japanese encephalitis or West Nile encephalitis and the hepatitis C and G viruses. While flaviviruses are capable of causing considerable morbidity and mortality in humans, the infection is generally asymptomatic and only a fraction of the individuals infected develop a serious disease.

Flaviviruses are small enveloped viruses. Their genome is a single-stranded RNA molecule of positive polarity, approximately 11 000 bases in length. The genomic RNA is associated with several copies of capsid protein C, so as to form the nucleocapsid; it is surrounded by a viral envelope consisting of a double lipid layer derived from the membranes of the endoplasmic reticulum (ER), in which the envelope protein E and the membrane protein M are anchored. The genomic RNA of flaviviruses contains a single open reading frame of approximately 10 500 nucleotides flanked by two short noncoding regions at its 5' and 3' ends. The genome is translated into a polyprotein of approximately 3 400 amino acids which is the precursor of the structural proteins C, prM (intracellular precursor of M) and E in its N-terminal portion, and of at least seven nonstructural (NS) proteins, from NS 1 to NS5, in its C-terminal portion.

Until very recently, the West Nile virus was recognized as being a relatively nonpathogenic virus responsible for a flu-like syndrome and present in Africa, in southern Europe and in the Middle East; it was isolated during epidemics which occurred, in particular, in Israel in the 1950s and in South Africa in the 1970s.

Very recently, the epidemiology of the West Nile virus became modified and an increasing number of cases of encephalitis was observed during the epidemics occurring in Romania in 1996, in Israel in 1998 and in the USA in 1999.

Pathogenic strains were isolated during these epidemics (Anderson et al., and Lanciotti et al., Science, 1999, 286: 2331-2333, 2333-2337), in particular the strain NY1999 (GenBank No. AF202541, Lanciotti et al., mentioned above), the pathogenicity of which is thought to be correlated with the presence of an NTS glycosylation site in the envelope protein E (Jordan et al., Viral Immunol., 2000, 13, 4: 435-446).

All the poorly identified viral factors may be responsible for the seriousness of the infection, whereas the genetic constitution of the host (human or nonhuman) is thought to contribute to resistance to infection.

However, the data relating to these recently isolated pathogenic strains have not made it possible to determine all the viral factors and host genes involved in sensitivity/resistance to infection with Flaviviridae.

Murine models have made it possible to establish the existence of genetic resistance to infection with flaviviruses. It has been shown that certain mouse lines recently derived from the wild and belonging to the species *Mus musculus musculus* or *Mus spretus* (Det, BSVR, BRVR, PRI, CASA/Rk and CAST/Ei) are resistant to infection with flaviviruses, whereas the most common inbred laboratory lines, which derive mainly from the species *Mus musculus domesticus*, are not resistant to it (Sangster et al., J. Virol., 1993, 67: 340-347).

Resistance is controlled by at least one autosomal locus named Flv, located on chromosome 5, in mice, and three alleles, $Flv^s$, $Flv^r$ and $Flv^{mr}$, confer, respectively, sensitivity, resistance and intermediate resistance to infection with flaviviruses. Using a Murray valley encephalitis flavivirus strain and mice derived from backcrossing the resistant mouse line C3H/RV with the sensitive mouse line C3/He or BALB/c, the Flv locus was located in a 0.9 cM region of chromosome 5, in mice, between the markers D5Mit68 and D5Mit242 (G. R. Shellam et al., Rev. Sci. Tech. Off. Epiz. 1998, 17: 231-248).

The inventors have now isolated a novel strain of the West Nile virus, from samples taken from storks in Israel (in the town of Eilat) in September 1998, which was selected for studying the resistance/sensitivity of a host (human or nonhuman mammal) to infection with viruses of the family Flaviviridae.

In accordance with the invention, said isolated neurovirulent and neuroinvasive strain of the West Nile virus, named IS-98-ST1, is characterized in that its genome consists of the sequence SEQ ID No. 1 which encodes a polyprotein having the sequence SEQ ID No. 2.

The inventors have in particular shown that laboratory mice are extremely sensitive to infection with the strain IS-98-ST1, whereas the mouse lines SEG, WMP, STF and MAI, which derive from wild mice belonging to species which are different although of the same genus *Mus*, are completely resistant to infection with this strain; an intraperitoneal inoculation of 1 000 FFU (focus-forming units; FFU:LD50=100) is 100% lethal for laboratory mice, whereas the wild mice do not show any symptoms; in addition, the virus replicates in these mice, as shown by the appearance of specific serum antibodies.

A subject of the present invention is also reagents, derived from the strain IS-98-ST1, used for studying and diagnosing infections with Flaviviridae, which reagents are selected from the group consisting of the following reagents:

(a) a nucleic acid molecule chosen from the sequence SEQ ID No. 1, the fragments of at least 15 nucleotides of the sequence SEQ ID No. 1 and the sense and antisense sequences complementary to the above sequences, excluding the fragment having the GENBANK sequence AF205882.

(b) a recombinant vector comprising a nucleic acid molecule as defined in (a), (c) a cell transformed with a nucleic acid molecule as defined in (a), a vector as defined in (b) or a neurovirulent strain of the West Nile virus as defined in (a), (d) a protein or a peptide encoded by a nucleic acid molecule as defined in (a), (e) a polyclonal antibody which can be obtained by immunizing a nonhuman mammal with the strain IS-98-ST1 of the West Nile virus, as defined above; preferably, said nonhuman mammal is a mouse homozygous for the $Flv^r$ allele, resistant to infection with Flaviviridae, and (f) a polyclonal or monoclonal antibody which can be obtained by immunizing a nonhuman mammal with a recombinant vector as defined in (b) or a protein or a peptide as defined in (d).

These various reagents are prepared and used according to the conventional techniques of molecular biology and immunology, according to standard protocols such as those described in *Current Protocols in Molcular Biology* (Frederick M. AUSUBEL, 2000, Wiley and Son Inc. Library of Congress, USA) and in *Current Protocols in Immunology* (John E. Coligan, 2000, Wiley and Son Inc. Library of Congress, USA).

The nucleic acid fragments as defined above, in particular those corresponding to the sequences SEQ ID Nos. 3-11, are used, for example, as a probe or as a primer for diagnosing infection with the West Nile virus; the infection is detected, for example, by PCR and/or hybridization, using the nucleic acids extracted from a biological sample taken from an individual liable to be infected or a laboratory animal inoculated with said virus.

According to an advantageous embodiment of said fragments, they comprise at least 15 nucleotides of SEQ ID No. 1, upstream or downstream of one of the codons at the following position.

alanine (A) codon at positions 1117-1119, corresponding to the residue at position 51 of the E protein or at position 341 of the sequence of the viral polyprotein of sequence SEQ ID No. 2 (the sequence of the E protein extends from the codons at position 291 to 791 of the sequence SEQ ID No. 2, corresponding to nucleotides 967 to 2469 of the sequence SEQ ID No. 1), asparagine (N) codon at positions 2518-2520, corresponding to the residue at position 17 of the NS1 protein or at position 808 of the sequence SEQ ID No. 2 (the sequence of the NS1 protein extends from the codons at position 792 to 1144 of the sequence SEQ ID No. 2, corresponding to nucleotides 2470 to 3528 of the sequence SEQ ID No. 1), arginine (R) codon at positions 4018-4020, corresponding to the residue at position 164 of the NS2A protein or at position 1308 of the sequence SEQ ID No. 2 (the sequence of the NS2A protein extends from the codons at position 1145 to 1374 of the sequence SEQ ID No. 2, corresponding to nucleotides 3529 to 4218 of the sequence SEQ ID No. 1), glycine (G) codon at positions 4462-4464 and glutamic acid (E) codon at positions 4465-4467, corresponding, respectively, to the residue at position 82 and 83 of the NS2B protein or at position 1456 and 1457 of the sequence SEQ ID No. 2 (the sequence of the NS2B protein extends from the codons at position 1375 to 1505 of the sequence SEQ ID No. 2, corresponding to nucleotides 4219 to 4611 of the sequence SEQ ID No. 1), proline (P) codon at positions 6097-6099 and glutamic acid codon at positions 6172-6174, corresponding, respectively, to the residue at position 496 and 521 of the NS3 protein or at position 2001 and 2026 of the sequence SEQ ID No. 2 (the sequence of the NS3 protein extends from the codons at position 1506 to 2124 of the sequence SEQ ID No. 2, corresponding to nucleotides 4612 to 6468 of the sequence SEQ ID No. 1), and serine (S) codon at positions 7840-7842, asparagine (N) codon at positions 8518-8520 and alanine (A) codon at positions 8794-8796, corresponding, respectively, to the residue at position 54, 280 and 372 of NS5 or at position 2582, 2808 and 2900 of the sequence SEQ ID No. 2 (the sequence of the NS5 protein extends from the codons at position 2529 to 3430 of the sequence SEQ ID No. 2, corresponding to nucleotides 7681 to 10386 of the sequence SEQ ID No. 1).

Such primers are useful for amplifying fragments containing said codons.

Said primers are preferably located between 10 and 100 nucleotides upstream or downstream of said codons.

According to another advantageous embodiment of said fragments, they consist of the fragments comprising the abovementioned codons, preferably of between 50 and 200 nucleotides, which are amplified using the primers as defined above.

The recombinant vectors as defined above, in particular the expression vectors, and the cells transformed with said expression vectors, are advantageously used for producing the corresponding peptides and proteins.

Said proteins and said peptides, which can be recognized by, and/or can induce the production of, antibodies specific for the West Nile virus, in particular for neurovirulent strains, are useful for diagnosing infection with a West Nile virus; the infection is detected using a suitable technique, in particular EIA, ELISA, RIA or immunofluorescence, using a biological sample taken from an individual liable to be infected or a laboratory animal inoculated with said virus. The proteins and peptides as defined above are also used to investigate cellular partners of these viral proteins which may be involved in the pathogenicity (neurovirulence) of the West Nile virus; these partners are identified using immunoaffinity techniques, for example using immunoaffinity column chromatography.

The antibodies according to the invention are useful for diagnosing infection with a West Nile virus, in particular neurovirulent strains; the infection is detected using a suitable technique, in particular EIA, ELISA, RIA or immunofluorescence, using a biological sample taken from an individual liable to be infected or a laboratory animal inoculated with said virus. Among these antibodies, those produced by immunizing $Flv^r/Flv^r$ mice with the strain IS-98-ST1 advantageously have a high titer and a very high specificity for the West Nile virus.

The transformed cells according to the invention, in particular neural cells (neurons and endothelial cells) infected with a neurovirulent strain as defined above, are used to identify the genes derived from these cells, the expression of which may be modulated during the viral infection; these genes are detected, for example, using biochip technology according to conventional protocols as described in Atlas Mouse Arrays (#membranes) ATLAS™ NYLON cDNA EXPRESSION ARRAYS (CLONTECH, USA).

A subject of the present invention is also a model for studying sensitivity/resistance to infection with a virus of the family Flaviviridae, characterized in that it comprises at least one neurovirulent strain of the West Nile virus as defined above.

According to an advantageous embodiment of said model, it also comprises a mouse homozygous for the $Flv^r$ or $Flv^s$ allele.

A subject of the present invention is also a method for detecting Flaviviridae infection, in particular a West Nile virus infection, characterized in that it comprises:

amplifying the RNAs derived from a biological sample to be tested, using the primers as defined above, and sequencing the amplification product obtained.

Such a detection may advantageously make it possible to establish a prognosis for the severity of a viral encephalitis caused by the West Nile virus.

The neurovirulent strain of the West Nile virus according to the invention is used to screen cellular genes involved in the resistance of a mammal to infection with a virus of the family Flaviviridae, preferably the hepatitis C virus.

Advantageously, said screening method comprises the following steps:

culturing cells derived from a host (human or nonhuman) selected for its resistance or its sensitivity to infection with a Flaviviridae, infecting said cells with a Flaviviridae, in vitro, and detecting genes expressed differentially in said infected cells.

In accordance with the invention, said detection may comprise establishing the transcript or protein profile using said cells.

A subject of the present invention is also the use of the model as defined above for sorting molecules which are active against a viral infection due to a virus of the family Flaviviridae.

A subject of the present invention is also a method for sorting molecules which are active against infection with a Flavivirus, characterized by:

bringing a culture of eukaryotic cells, derived from a mammal (human or nonhuman) sensitive to infection with a Flaviviridae, into contact with a viral suspension of the strain as claimed in claim 1, in the presence or absence of the molecule to be tested, and detecting the amplification/replication of the virus, by any known method (quantification genome, mRNA, proteins, viral particles).

A subject of the present invention is also a variant of the viral strain as defined above, characterized in that its genome comprises at least one mutation in the nucleotide sequence corresponding to the NS5 protein.

Figure 3:
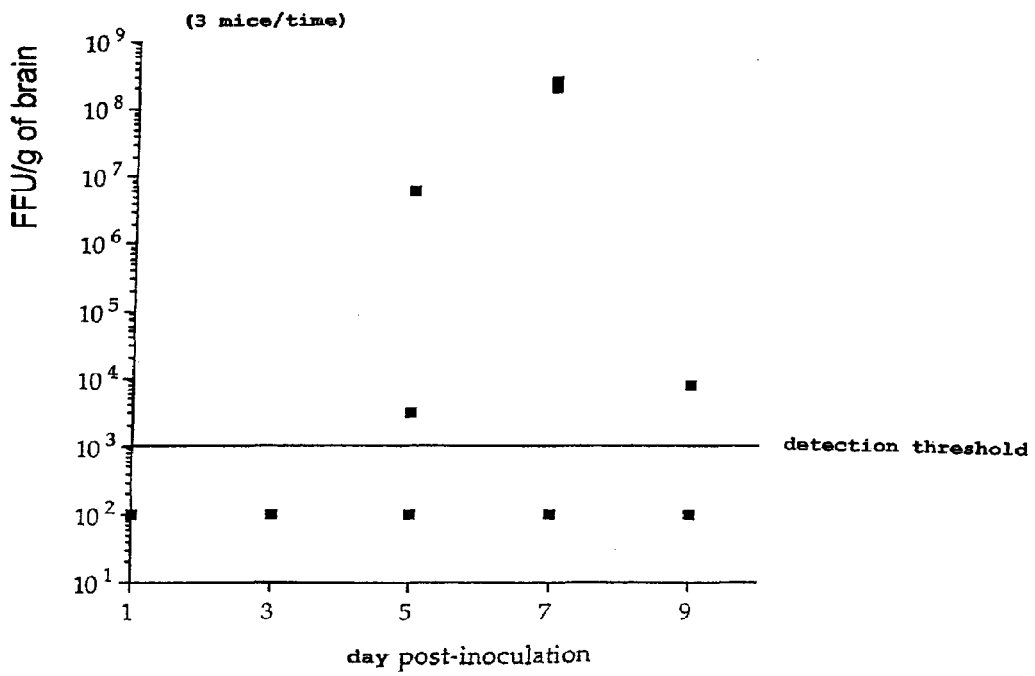
Figure 4:
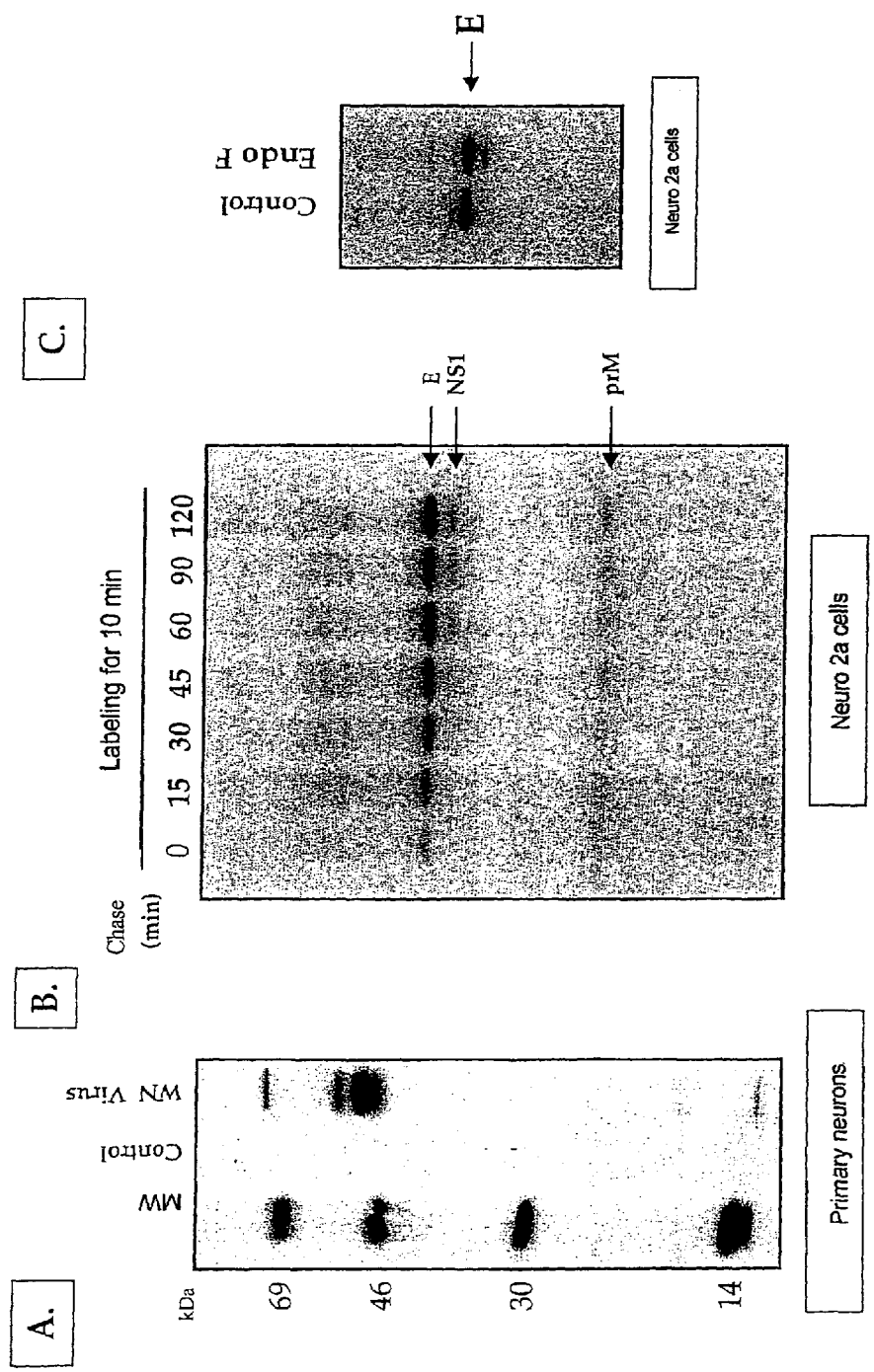
Figure 5:
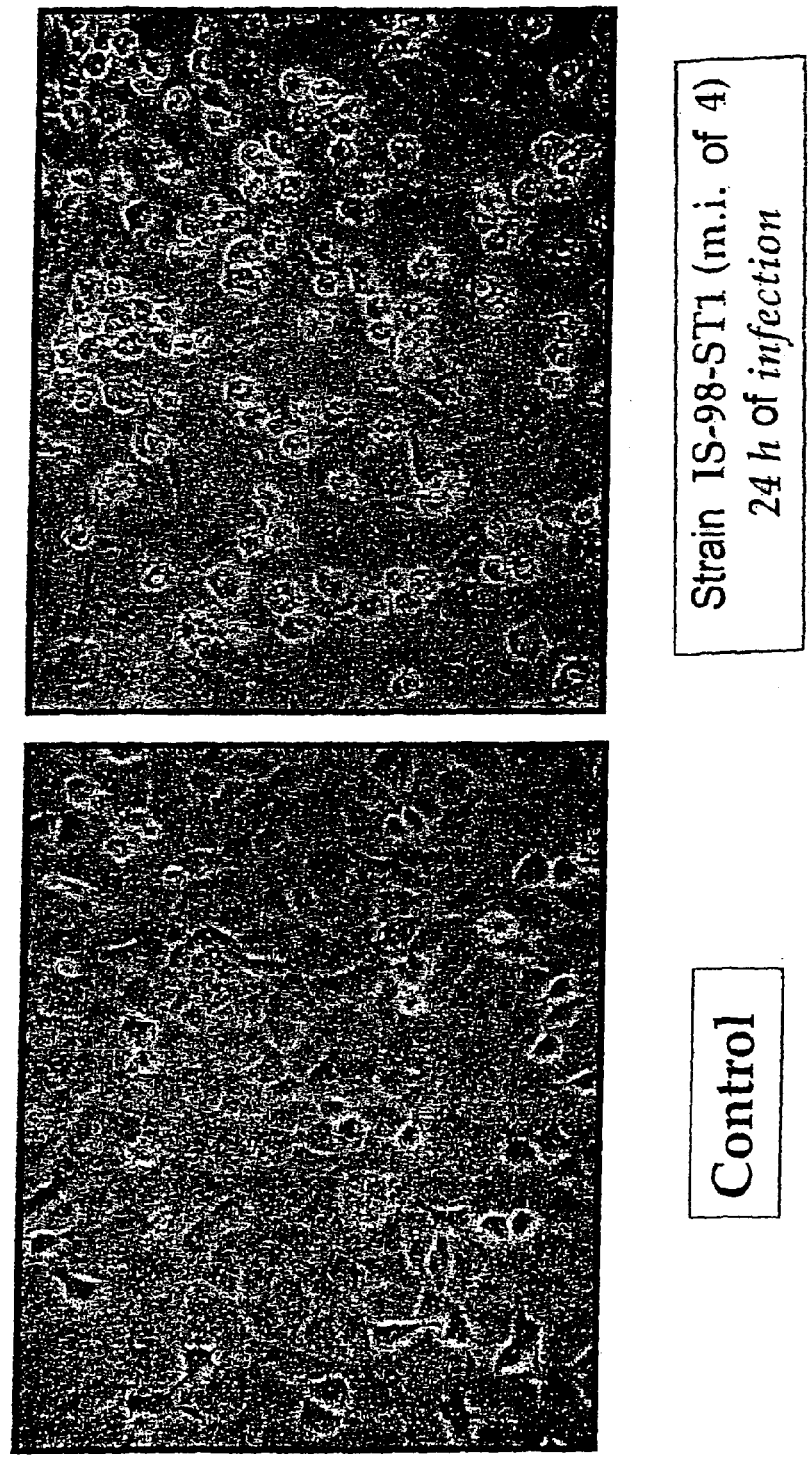
Figure 6:
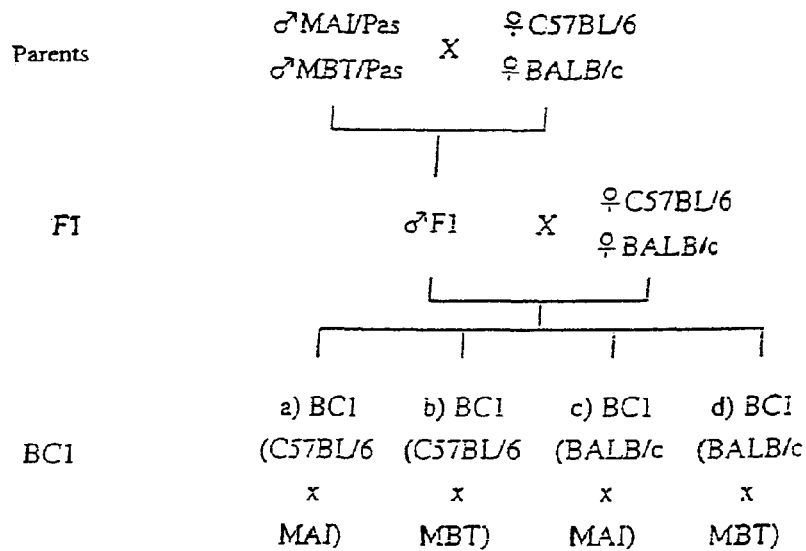
Figure 7:
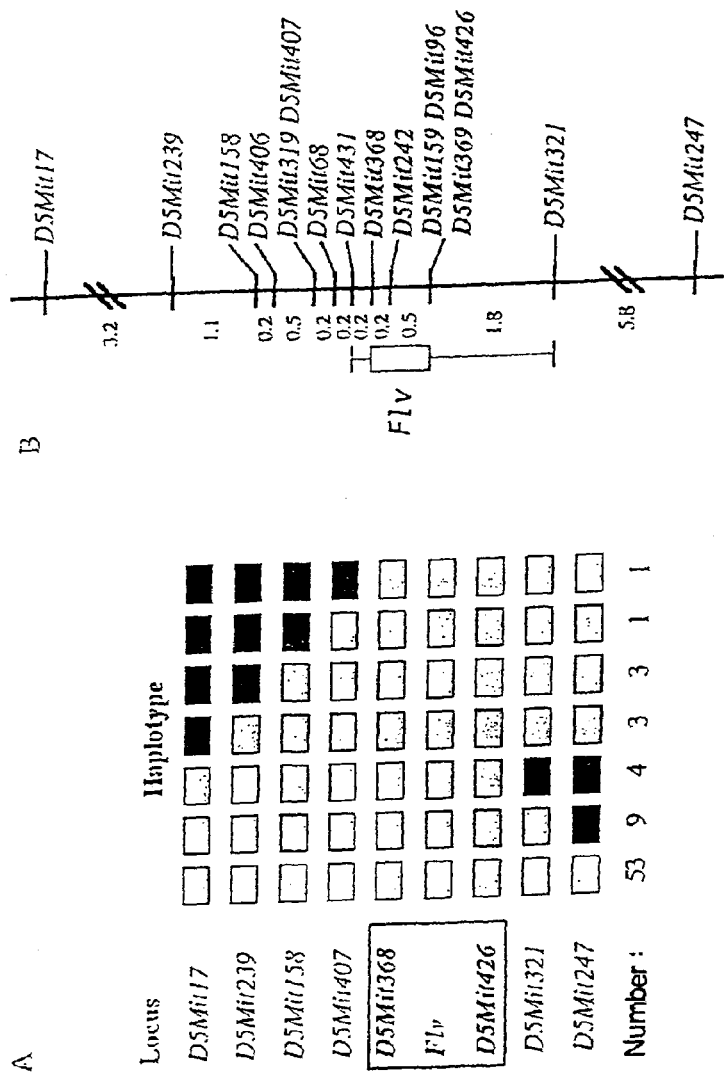
Figure 8:
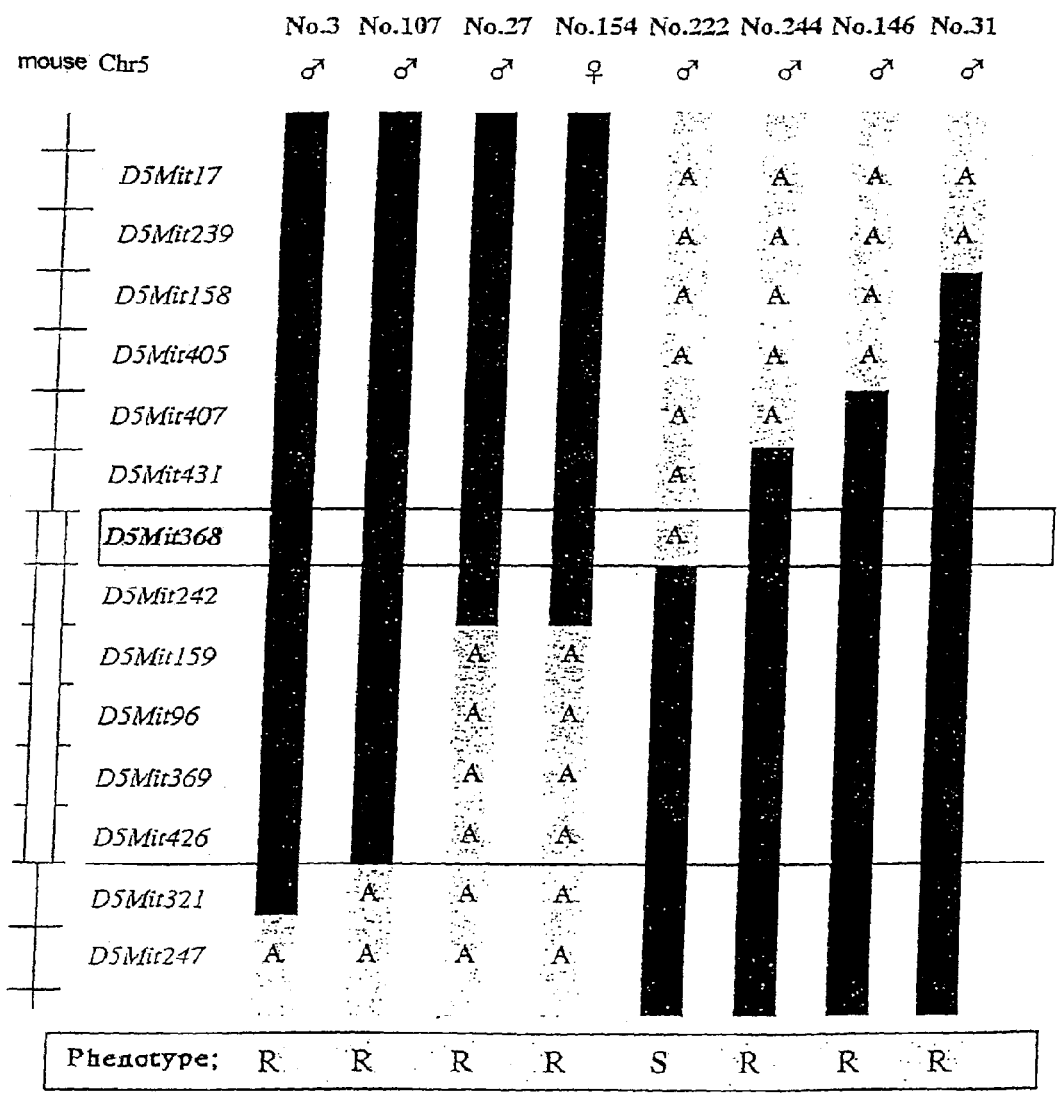

Besides the above arrangements, the invention also comprises other arrangements which will emerge from the following description, which refers to examples of implementation of the subject of the present invention, with references to the attached drawings in which:

FIGS. 1A to 1E represent the comparison of the amino acid sequence of the viral proteins of the strain IS-98-ST1 (SEQ ID No. 2), isolated from storks (CI), and of the New York strain (NY99; Genbank AF196835-SEQ ID NO:12) isolated from pink flamingos during the 1999 epidemic in the United States, FIG. 2 represents the kinetics of mortality and the kinetics of appearance of specific serum antibodies in $Flv^s/Flv^s$ sensitive mice (BALB/c) infected with the IS-98-ST1 strain of the West Nile virus, FIG. 3 represents the kinetics of propagation of the strain IS-98-ST1 in the central nervous system of $Flv^s/Flv^s$ sensitive mice (BALB/c), FIGS. 4(A, B and C) represent the kinetics of appearance of the viral antigens in Neuro 2a cells and primary neurons from sensitive mice (BALB/c) infected with the West Nile virus (strain IS-98-ST1), FIG. 5 represents the death by necrosis of Neuro 2a cells infected with the West Nile virus (strain IS-98-ST1), FIG. 6 represents the experimental protocol used to specify the location of the Flv locus on mouse chromosome 5, FIG. 7 represents the genetic map of the Flv locus, determined using sensitive mice derived from the first backcross between resistant lines (MAI/Pas and MBT/Pas) and sensitive lines (C57BL/6 or BALB/c). The white boxes represent the BALB/c or C57Bl/6 alleles and the black boxes represent the MAI/Pas or MBT/Pas alleles, FIG. 8 represents the genetic map of the Flv locus, determined using resistant mice and sensitive mice, derived from the first backcross (BC1) between resistant lines (MAI/Pas and MBT/Pas) and sensitive lines (C57BL/6 and BALB/c). The shaded lines represent the BALB/c or C57Bl/6 alleles and the black lines represent the MAI/Pas or MBT/Pas alleles.

Figure 9:
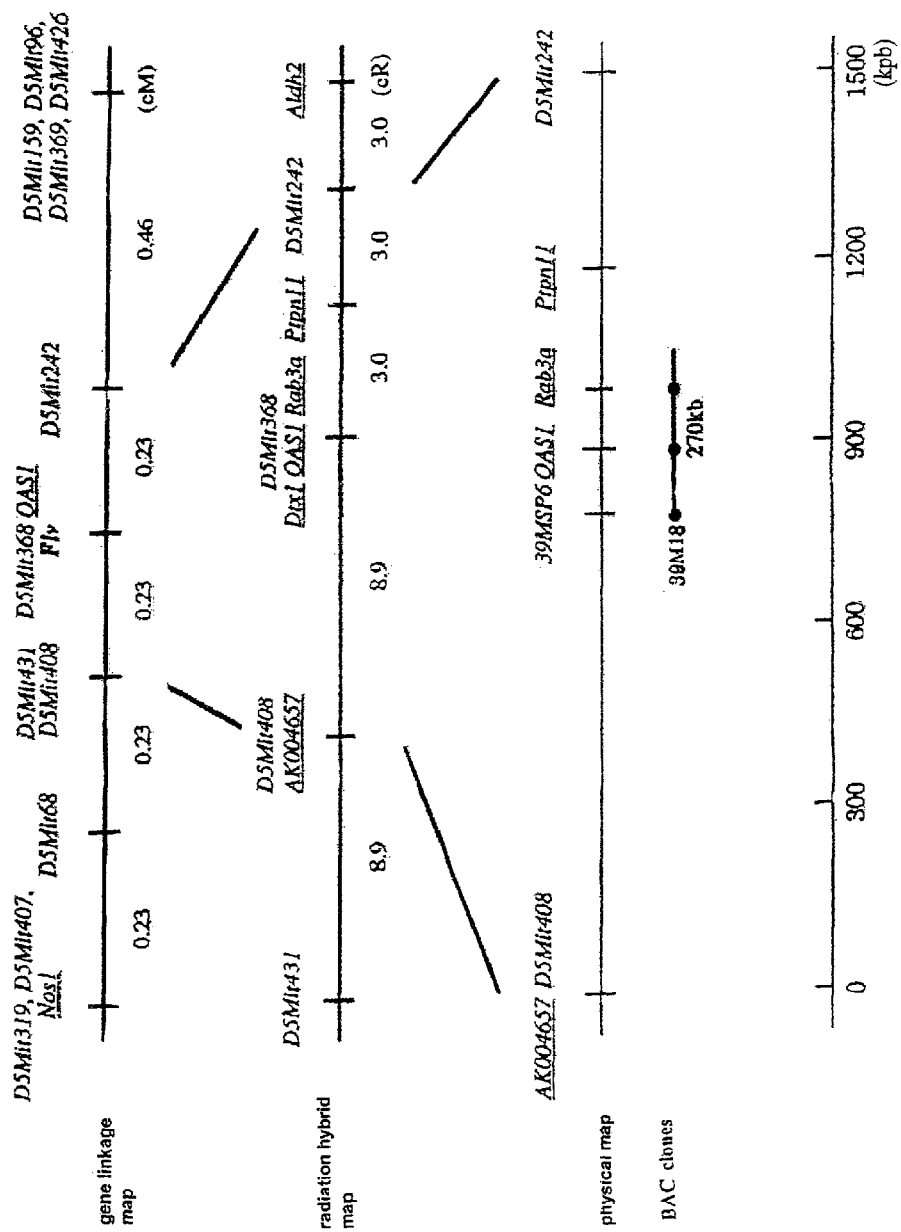

FIG. 9 represents the genetic map and the physical map of the Flv locus and the position of the OAS gene in this locus, and FIG. 10 represents the distribution of Flv alleles in resistant mice and sensitive mice, derived from the first backcross (BC1) between resistant lines (MAI/Pas and MBT/Pas) and sensitive lines (C57BL/6 and BALB/c).

EXAMPLE 1

Isolating, Amplifying, Purifying and Titering the Neuroinvasive Strain of the West Nile Virus, 15-98-ST1

An isolate of the West Nile (WN) virus was obtained from the central nervous system of a stork exhibiting severe neuropathological problems, in September 1998 in Eilat (Israel). Infection of VERO cells with this isolate is cytolytic and indirect immunofluorescence with an immune mouse ascites specific for the West Nile virus (immune serum of reference WN 8907) is 100% positive. The virus produced on VERO cells was harvested and amplified on AP61 mosquito cells (Després et al., Virol., 1993, 196, 209-219).

Passage 1 (or P1) of the WN virus on AP61 cells was harvested 3 days after infection; it has a titer of $2.5 \times 10^8$ FFU/ml (Focus-Forming Unit) by the technique for titering on AP61 cells described in Després et al. (mentioned above). The P1 inoculum of the WN virus on AP61 cells was identified as the strain IS-98-ST1.

A P2 was obtained from AP61 cells infected with the strain IS-98-ST1, P1 (titer: $6 \times 10^7$ FFU/ml). The P2 inoculum of IS-98-ST1 is used for the tests for sensitivity to viral infection in adult mice.

A P3 viral inoculum of the strain IS-98-ST1, with a titer of $5 \times 10^7$ FFU/ml, was produced on PA61 cells. A highly purified viral preparation, prepared according to the flavivirion purification protocol described in Després et al., 1993) was obtained from twenty 150 cm² dishes of AP61 cells harvested 3 days after infection with the P3 inoculum of the WN virus strain IS-98-ST1 (multiplicity of infection of 0.4). The strain IS-98-ST1 purified on sucrose gradients has a final titer of $2 \times 10^{10}$ FFU/ml. The RNAs extracted from this purified virus are used to amplify the cDNAs corresponding to the C, prM and NS 1 viral proteins or to the noncoding sequences at the 5' and 3' ends of the viral genome.

EXAMPLE 2

Sequencing the Genome of the Neuroinvasive Strain 15-98-ST1

The viral genome was extracted from the culture supernatant of the infected VERO cells of example 1 using the "QIAamp Viral RNA" kit (QUIAGEN), according to the manufacturer's instructions. 6 overlapping RT-PCR products were amplified from these RNAs using the primers described by Lanciotti et al. (mentioned above). The 5' and 3' ends of the viral genome were amplified, respectively, using the following primers:

```
                                           (SEQ ID No. 5)
    5'AGTAGTTCGCCTGTGTGAGCTGACAAAC 3',
    and (SEQ ID No. 6)
    5'AGATCCTGTGTTCTCGCACCACCAGCCAC 3'.
```

The cDNA corresponding to the E viral protein was amplified using the primers 5' GGATGGATGCT(A/T)GG(G/T)AGCAAC 3' (SEQ ID No. 7) and 5' CCATCCAAGCCTCCACATC 3' (SEQ ID No. 8), which hybridize, respectively, in the gene of the M protein (positions 889 to 909 of the sequence SEQ ID No. 1) and in the gene of the NS1 protein (positions 2539 to 2557 of the sequence SEQ ID No. 1).

The cDNAs obtained were purified by ion exchange chromatography and precipitated in 2 volumes of isopropanol. The cDNAs were then sequenced on both strands using the "Taq Dye Deoxy Terminator Cycle Sequencing" kit (PERKIN ELMER CORP./APPLIED BIOSYSTEM) and primers 400 base pairs apart on the viral genome (Lanciotti et al., mentioned above). The sequencing was performed with 0.2 pmol of purified cDNA and 30 pmol of primers, according to the protocol recommended by the manufacturer. The sequence alignment is produced using the CLUSTAL W program.

The complete genomic sequence of the strain IS-98-ST1 of the West Nile virus corresponds to the sequence SEQ ID No. 1.

The amino acid sequence alignment for the strain IS-98-ST1 (SEQ ID No. 2) and the strain NY99, given in FIG. 1, shows that the strain IS-98-ST1 isolated in Israel in 1998 and the strain NY-99 isolated in New York in 1999 are very close (less than 0.2% divergence at the amino acid sequence level).

However, the differences observed in the strain IS-98-ST1 in the E ($A_{51}$), NS1 ($N_{17}$), NS2A ($R_{164}$), NS2B ($G_{82}$, $E_{83}$), NS3 ($P_{496}$, $E_{521}$) and NS5 ($S_{54}$, $N_{280}$, $A_{372}$) proteins, respectively, are potentially responsible for the neurovirulence and for the neuroinvasive properties observed with this strain and may be used as a virulence marker for the West Nile virus.

EXAMPLE 3

Cloning the Proteins of the Neuroinvasive Strain IS-98-ST1 and Uses of the Recombinant Plasmids Obtained 1—the C Protein The genomic RNA extracted from the IS-98-ST1 virions purified on sucrose gradients described in example 1, using the RNA PLUS 2 solution (Q.BIOGEN), is used as a matrix for amplifying the sequence encoding the C protein (amino acids 1 to 123) using the RT-PCR technique (Titan One Tube RT-PCR kit; Roche Biochemicals #1939 823).

The pair of primers used on the RNA matrix is as follows:
5'C/WNV (sequence of nt 81-117 of the sequence SEQ ID No. 1) 5' TAGCACGAAGAATTCGATGTCTAAAAAC-CAGGAGGG 3' (SEQ ID No. 11), which contains the EcoRI restriction site, and 3'C/WNV (antisense sequence of nt 433 to 482 of the sequence SEQ ID No. 1) 5' AAGTTAGCCCGGGTTAAT-GCTCCTACGCTGGCGATCAGGCCAATCAGGAC 3' (SEQ ID No. 4), which contains the SmaI restriction site.

The cDNA of the C protein of the strain IS-98-ST1 (amino acids 1 to 123) of the WN virus was cloned, firstly, between the EcoRI and SmaI sites of the plasmid pCI-neo (Promega #E1841) and, secondly, between the KspI and SmaI sites of the plasmid pIVEX 2.4a (Roche).

The recombined plasmid pCI-C/WN (registered on Jun. 21, 2001, with the Collection Nationale de Culture de Microorganismes [National Collection of Microorganism Cultures] of the Pasteur Institute in Paris, 28, rue du Docteur Roux, 75724, PARIS Cedex 15, under the number 1-2688) contains the complete sequence of the C protein gene of the strain IS-98-ST1 of the WN virus, between the T7 and T3 promoters. The transcription, in vitro, of pCI-C/WN linearized with NheI, under the control of the T3 promoter, synthesizes an RNA of approximately 350 bases complementary to the genomic viral sequence. The riboprobe labeled with DIG (digoxigenin) is used to detect the positive-sense viral RNAs in cells infected with the WN virus, using the in situ hybridization technique, according to the protocol described in Després et al., (*J. Virol.*, 1998, 72: 823-829).

The recombinant plasmid pIVEX-C/WN is used for the mass production of the WN virus C protein (amino acids 1 to 123) in bacterial lysate (Roche RTS 500 system). The recombinant C protein produced in vitro has, at its N-terminal end, a $[His]_6$ sequence and the cleavage site recognized by the Xa protease, so as, firstly, to allow it to be purified on an Ni column and, secondly, to allow the histidine residues to be removed. The C protein of the strain IS-98-ST1 of the WN virus thus produced is used for structural studies, to search for cellular partners for this protein on an immunoaffinity column, and to produce monospecific antibodies in rabbits.

2—The M Protein

The cDNAs, of the strain IS-98-ST1 of the WN virus, encoding the M protein (amino acids 215 to 290 of the viral polyprotein) or its 41 amino acid ectodomain (amino acids 215 to 255; acronym ectoM) are cloned:

(1) in phase with the C-terminal end of EGFP, into the plasmid p[95-114]EGFP, derived from the plasmid pEGFP-N1 (Clontech), which comprises residues 95-114 of the C protein of dengue virus type 1 (strain BR/90), fused in phase with the N-terminal sequence of the protein EGFP[215-290] WNV, to give the plasmid p[95-114]EGFP[215-290]WNV, (2) into the plasmid pIVEX (Roche RTS 500 system), to give the plasmid pIVEX[EGFP][215-255]WNV, (3) into the retroviral vector TRIPdeltaU3CMV, to give the plasmid TRIPdeltaU3CMV[95-114]EGFP[215-255] WNV.

The plasmid pIVEX[EGFP][215-255]WNV allows the extracellular synthesis and the purification of the chimeric protein EGFP-ectoM WNV, which is used, firstly, to produce monospecific antibodies directed against the M protein of the WN virus and, secondly, to search for cellular partners of the ectoM WNV molecule on an immunoaffinity column.

The plasmid TRIPdeltaU3CMV[95-114]EGFP[215-255] WNV is cotransfected into 293T cells with the plasmids 8.7 and G-VSV, in order to produce the viral particles pseudotyped with the G envelope of the vesicular stomatitis virus (VSV), containing the inner proteins of the acquired immunodeficiency virus (HIV) and chimeric CMV[95-114] EGFP[215-255]WNV RNA molecules. Infection of target cells with the nonreplicative recombined vector allows intele;.5qgration of the CMV[95-114]EGFP[215-255]WNV DNA into the cellular genome and stable expression of the ectodomain of the M-WN protein under the control of the CMV promoter.

3—The NS 1 Protein

The genomic RNA extracted from the purified IS-98-ST1 virions is amplified using the RT-PCR technique (Titan One Tube RT-PCR kit; Roche Biochemicals #1939 823) using the following pair of primers:

5' TGGATGGGATCCAATATGCGTGATAGGTCC 3' (SEQ ID No. 9), which contains the BamHI restriction site, and 3' AAAAGGGTCAATGGTACCAGCATTTTAAGCAT-TCACGTT 3' (SEQ ID No. 10), which contains the KpnI restriction site.

The cDNA encoding the NS1 glycoprotein with its signal peptide (amino acids 767 to 1143 of the viral polyprotein) is cloned between the BamHI and KpnI sites of the retroviral vector TRIPdeltaU3, so as to produce the recombined plasmid TRIPdeltaU3-CMV-NS1-WN (registered on Jan. 9, 2002, with the Collection Nationale de Culture de Microorganismes [National Collection of Microorganism Cultures] of the Pasteur Institute in Paris, 28 rue du Docteur ROUX, 75724, PARIS Cedex 15, under the number 1-2770). The plasmid TRIPdeltaU3-CMV-NS1-WN is cotransfected into 293T cells with the plasmids 8.7 and G-VSV, in order to produce viral particles pseudotyped with the G envelope of the vesicular stomatitis virus (VSV), containing the inner proteins of the acquired immunodeficiency virus (HIV) and chimeric CMV-NS1-WN RNA molecules. Infection of target cells with the nonreplicative recombined vector allows integration of the CMV-NS1-WN DNA into the cellular genome and stable expression of the NS 1 protein of the WN virus under the control of the CMV promoter. The NS1 protein of the strain IS-98-ST1 of the WN virus thus produced is used for structural studies, to search for cellular partners of this protein on an immunoaffinity column, and to produce monospecific antibodies in rabbits

EXAMPLE 4

Wild Mice and Inbred Laboratory Mice Differ in their Sensitivity to Infection with the Neuroinvasive Strain IS-98-ST1 of the West Nile Virus 1—Sensitive Mouse Lines and Cells a) Sensitive Mouse Lines 6-week-old mice from $Flv^s$ sensitive inbred lines (BALB/c) are inoculated intraperitoneally with 100 FFU of the strain IS-98-ST1 of the West Nile virus (FFU:LD50=10), prepared as described in example 1.

100% of these mice die with a mean mortality time of 9±2 days (FIG. 2).

The kinetics of propagation of the strain IS-98-ST1 in the central nervous system of the sensitive mice (BALB/c) was analyzed using brain extracts from the infected mice titered on AP61 cells, according to the technique described in according to the technique described in Després et al. (*J. Virol.*, 1998, 72, 823-829). The results show that the virus is detected in the murine central nervous system (CNS) on the 5th day of infection and viral production is at a maximum on the 7th day (FIG. 3). On the 9th day of infection, the virus is no longer detected in the murine CNS (FIG. 3).

Replication of the WN virus in the CNS and the peripheral organs of the mice infected with the strain IS-98-ST1 is also detected by immunohistology, according to conventional protocols as described in Després et al., 1998 (mentioned above) and by in situ hybridization, according to the protocols described in example 3.

The serum antibodies specifically directed against the proteins of the WN virus are titered by ELISA according to the protocol described in Després et al., 1993 (mentioned above), using the strain IS-98-ST1 purified on a sucrose gradient as described in example 1, as antigen. The results show that the serum antibodies appear on the 5th day of infection and are significantly detected on the 7th day (FIG. 2).

b) Sensitive Cells b1) Primary Cultures

Primary neurons and astrocytes from the CNS of sensitive mice homozygous for the $Flv^s$ allele (Swiss mice, Janvier) are prepared according to conventional protocols. The cells are infected with the strain IS-98-ST1 at a multiplicity of infection of 20 FFU per cell (m.i. of 20). The cytopathic effect is observed by light microscopy, viral production is analyzed by titering on AP61 cells as described previously in example 1, and expression of the viral antigens is analyzed by radioimmunoprecipitation using an anti-West Nile mouse immune serum, according to conventional protocols as described in Duarte Dos Santos et al. (*Virology*, 2000, 274: 292-308).

The results show that 80% of the neurons in culture produce the viral antigens:

their SDS-polyacrylamide gel profile is given in FIG. 4A;

the viral production is $[3.0 \pm 1.5] \times 10^6$ FFU/ml after 20 h of infection and $[7.0 \pm 0.5] \times 10^7$ FFU/ml at 40 h;

the cytopathic effects (CPEs) of the necrotic type are observed after 48 h of viral infection.

On the other hand, astrocytes of the murine CNS are not permissive to replication of the WN virus strain IS-98-ST1.

$b_2$) Cell Lines

Neuro 2a murine neuroblastoma cells and HepG2 human hepatoma cells, cultured under conventional conditions as described in Marianneau et al. (*J. Virol.*, 1996, 77: 2547-2554), are infected at various multiplicities of infection with the WN virus strain IS-98-ST1, prepared as described in example 1. The cytopathic effect is observed by light microscopy, viral production is analyzed by titering on AP61 cells as previously described in example 1, and expression of the viral antigens is analyzed by radioimmunoprecipitation using an anti-West Nile mouse immune serum, according to conventional protocols as described in Duarte Dos Santos et al., Virol., 2000, 274, 292-308.

The results show that Neuro 2a murine neuroblastoma cells are permissive to replication of the strain IS-98-ST1 of the WN virus. An m.i. of 4 is necessary to infect 80% of the Neuro 2a cells in monolayer. The viral production of $10^7$ FFU/ml (m.i. of 4) after 40 h of infection, and there is massive cell death by necrosis (FIG. 5). The kinetics of production of the major antigens prM, E and NS 1 from the viral polyprotein, given in FIG. 4B, shows that the half-time of formation of the envelope glycoprotein E is approximately 30 min. The E protein of the strain IS-98-ST1 appears to have only one N-glycan residue (FIG. 4C).

The results also show that HepG2 human hepatoma cells are permissive to replication of the strain IS-98-ST1 of the WN virus. At an m.i. of 10, the viral production is $[2 \pm 1] \times 10^6$ FFU/ml after 48 h of infection and the CPEs are observed from 72 h.

2—Resistant Mice

The resistant (F10 mouse lines which derive from wild mice of the species *Mus spretus* (SEG/Pas and STF/Pas), *Mus musculus musculus* (MBT/Pas, MAI/pas) and *Mus musculus domesticus* (WMP/Pas) are inoculated intraperitoneally with 1 000 FFU (100 LD50) of the strain IS-98-ST1 prepared according to the protocol described in example 1.

Unlike the laboratory mice which are sensitive to infection with the strain IS-98-ST1 and die in about ten days, these mice derived from wild mice are resistant to inoculation with the strain IS-98-ST1 and, nevertheless, permissive to replication of the strain IS-98-ST1. In fact, viral infection of the mice derived from wild mice is asymptomatic, although the virus multiplies, in toto, as demonstrated by the production of anti-WN serum antibodies at high titers; by ELISA, the titers of the sera at a dilution of 1:100, for $10^6$ FFU of purified IS-98-ST1 virion, are greater than 1 O.D. unit at 450 nm.

The mice resistant to viral infection are used to produce immune sera specifically directed against the proteins of the strain IS-98-ST1 of the WN virus. Three weeks after inoculation with the WN virus, the sera taken from resistant mice (0.045 ml per mouse) are mixed, decomplemented for 30 min at 56° C. and then diluted to 1:10 in DPBS* (v/v) supplemented with 0.2% (v/v) of bovine serum albumin (Life Technologies) and 0.05% (w/v) of sodium azide. The diluted sera are divided up into 0.2 ml aliquots and stored at −20° C. The immune sera directed against the strain IS-98-ST1 are used at the final dilutions of 1:500 for indirect immunofluorescence and at 1:1 000 for immunoprecipitation of radiolabeled viral proteins

EXAMPLE 5

Use of the Strain IS-98-ST1 of the West Nile Virus to Identify the Cellular Genes Involved in Host Sensitivity to Infection with Viruses of the Family Flaviviridae 1) Methods
a) Model for Analyzing Resistance to Infection with Flaviviridae (FIG. 6)

Male mice of the resistant lines MAI/Pas and MBT/Pas are crossed with female mice of the sensitive lines C57BL/6 and BALB/c. The male mice of the F1 generation are backcrossed with female mice of the sensitive lines C57BL/6 and BALB/c, to give a generation of first backcross (BC1) mice.

Five-week-old BC1 mice are inoculated intraperitoneally with the strain IS-98-ST1, prepared according to the protocol described in example 1, under the conditions described in example 2.

The animals are observed every day and the mortality and survival rates are determined 14 days after infection.

b) Genotyping of Flv Alleles

The Flv alleles of the BC1 individuals were mapped by genomic PCR using primers specific for 16 microsatellites of chromosome 5 (Catalogue Research Genetics) surrounding the Flv locus (FIGS. 7-9), according to common techniques of molecular biology using standard protocols such as those described in *Current Protocols in Molecular Biology* (Frederick M. AUSUBEL, 2000, Wiley and Son Inc. Library of Congress, USA).

2) Results

Analysis of Flv allele distribution in the BC1 mice sensitive and resistant to infection with the strain IS-98ST1 shows that one Flv$^r$ allele is sufficient to confer resistance to infection (FIG. 10). The results also show that, in this model, a perfect correlation exists between the resistant phenotype and the presence of the Flv$^r$ allele and an almost perfect correlation exists between the sensitive phenotype and the absence of the Flv$^r$ allele (FIG. 10).

The genotyping of the Flv alleles shows that the Flv locus is located in a 0.2 cM region containing the OASI gene (FIGS. 7-9).

The invention claimed is:

1. An immunoassay method for detecting a west nile virus (WNV) infection comprising:
   (a) providing a biological sample suspected of containing anti-WNV antibodies
   (b) contacting the biological sample with an immunoassay composition comprising at least one isolated peptide consisting of an amino acid sequence encoded by a polynucleotide fragment consisting of between 50 and 200 contiguous nucleotides of the coding sequence SEQ ID NO: 1,
   wherein the 50 and 200 contiguous nucleotides of the coding sequence SEQ ID NO: 1 include a codon selected from:
   the alanine codon at positions 1117-1119 of SEQ ID NO: 1,
   the asparagine codon at positions 2518-2520 of SEQ ID NO: 1,
   the arginine codon at positions 4018-4020 of SEQ ID NO: 1,
   the glycine codon at positions 4462-4464 and/or and the glutamic acid codon at positions 4465-4467 of SEQ ID NO: 1,
   the proline codon at positions 6097-6099 and/or the glutamic acid codon at positions 6172-6174 of SEQ ID NO: 1,
   the serine codon at positions 7840-7842 of SEQ ID NO: 1,
   the asparagine codon at positions 8518-8520 of SEQ ID NO: 1, and
   the alanine codon at positions 8794-8796 of SEQ ID NO: 1; and
   (c) detecting an immunological reaction between an antibody present in the sample and at least one peptide present in the immunoassay composition.

2. The method of claim 1, wherein the polynucleotide fragment includes the alanine codon at positions 1117-1119 of SEQ ID NO: 1.

3. The method of claim 1, wherein the polynucleotide fragment includes the asparagine codon at positions 2518-2520 of SEQ ID NO: 1.

4. The method of claim 1, wherein the polynucleotide fragment includes the arginine codon at positions 4018-4020 of SEQ ID NO: 1.

5. The method of claim 1, wherein the polynucleotide fragment includes the glycine codon at positions 4462-4464 and/or and the glutamic acid codon at positions 4465-4467 of SEQ ID NO: 1.

6. The method of claim 1, wherein the polynucleotide fragment includes the proline codon at positions 6097-6099 and/or the glutamic acid codon at positions 6172-6174 of SEQ ID NO: 1.

7. The method of claim 1, wherein the polynucleotide fragment includes the serine codon at positions 7840-7842 of SEQ ID NO: 1.

8. The method of claim 1, wherein the polynucleotide fragment includes the asparagine codon at positions 8518-8520 of SEQ ID NO: 1.

9. The method of claim 1, wherein the polynucleotide fragment includes the alanine codon at positions 8794-8796 of SEQ ID NO: 1.

10. The method of claim 1, wherein the immunological reaction between an antibody present in the sample and at least one peptide present in the immunoassay composition is detected by a method comprising EIA.

11. The method of claim 1, wherein the immunological reaction between an antibody present in the sample and at least one peptide present in the immunoassay composition is detected by a method comprising ELISA.

12. The method of claim 1, wherein the immunological reaction between an antibody present in the sample and at least one peptide present in the immunoassay composition is detected by a method comprising RIA.

13. The method of claim 1, wherein the immunological reaction between an antibody present in the sample and at least one peptide present in the immunoassay composition is detected by a method comprising immunofluorescence.

* * * * *

SEQUENCE LISTING

```
<160> NUMBER OF SEQ ID NOS: 12

<210> SEQ ID NO 1
<211> LENGTH: 11029
<212> TYPE: DNA
<213> ORGANISM: Flavivirus sp.
<220> FEATURE:
<221> NAME/KEY: CDS
<222> LOCATION: (97)..(10395)

<400> SEQUENCE: 1
agtagttcgc ctgtgtgagc tgacaaactt agtagtgttt gtgaggatta acaacaatta        60
acacagtgcg agctgtttct tagcacgaag atctcg atg tct aag aaa cca gga       114
                                       Met Ser Lys Lys Pro Gly
                                       1               5 ggg ccc ggc aag agc cgg gct gtc aat atg cta aaa cgc gga atg ccc       162
Gly Pro Gly Lys Ser Arg Ala Val Asn Met Leu Lys Arg Gly Met Pro
            10                  15                  20 cgc gtg ttg tcc ttg att gga ctg aag agg gct atg ttg agc ctg atc       210
Arg Val Leu Ser Leu Ile Gly Leu Lys Arg Ala Met Leu Ser Leu Ile
        25                  30                  35 gac ggc aag ggg cca ata cga ttt gtg ttg gct ctc ttg gcg ttc ttc       258
Asp Gly Lys Gly Pro Ile Arg Phe Val Leu Ala Leu Leu Ala Phe Phe
    40                  45                  50 agg ttc aca gca att gct ccg acc cga gca gtg ctg gat cga tgg aga       306
Arg Phe Thr Ala Ile Ala Pro Thr Arg Ala Val Leu Asp Arg Trp Arg
55                  60                  65                  70 ggt gtg aat aaa caa aca gcg atg aaa cac ctt ctg agt ttt aag aag       354
Gly Val Asn Lys Gln Thr Ala Met Lys His Leu Leu Ser Phe Lys Lys
                75                  80                  85 gaa cta ggg acc ttg acc agt gct atc aat cgg cgg agc tca aaa caa       402
Glu Leu Gly Thr Leu Thr Ser Ala Ile Asn Arg Arg Ser Ser Lys Gln
            90                  95                  100
```

```
aag aaa aga gga gga aag acc gga att gca gtc atg att ggc ctg atc    450
Lys Lys Arg Gly Gly Lys Thr Gly Ile Ala Val Met Ile Gly Leu Ile
        105                 110                 115 gcc agc gta gga gca gtt acc ctc tct aac ttc caa ggg aag gtg atg    498
Ala Ser Val Gly Ala Val Thr Leu Ser Asn Phe Gln Gly Lys Val Met
120                 125                 130 atg acg gta aat gct act gac gtc aca gat gtc atc acg att cca aca    546
Met Thr Val Asn Ala Thr Asp Val Thr Asp Val Ile Thr Ile Pro Thr
135                 140                 145                 150 gct gct gga aag aac cta tgc att gtc aga gca atg gat gtg gga tac    594
Ala Ala Gly Lys Asn Leu Cys Ile Val Arg Ala Met Asp Val Gly Tyr
                155                 160                 165 atg tgc gat gat act atc act tat gaa tgc cca gtg ctg tcg gct ggt    642
Met Cys Asp Asp Thr Ile Thr Tyr Glu Cys Pro Val Leu Ser Ala Gly
            170                 175                 180 aat gat cca gaa gac atc gac tgt tgg tgc aca aag tca gca gtc tac    690
Asn Asp Pro Glu Asp Ile Asp Cys Trp Cys Thr Lys Ser Ala Val Tyr
        185                 190                 195 gtc agg tat gga aga tgc acc aag aca cgc cac tca aga cgc agt cgg    738
Val Arg Tyr Gly Arg Cys Thr Lys Thr Arg His Ser Arg Arg Ser Arg
200                 205                 210 agg tca ctg aca gtg cag aca cac gga gaa agc act cta gcg aac aag    786
Arg Ser Leu Thr Val Gln Thr His Gly Glu Ser Thr Leu Ala Asn Lys
215                 220                 225                 230 aag ggg gct tgg atg gac agc acc aag gcc aca agg tat ttg gta aaa    834
Lys Gly Ala Trp Met Asp Ser Thr Lys Ala Thr Arg Tyr Leu Val Lys
                235                 240                 245 aca gaa tca tgg atc ttg agg aac cct gga tat gcc ctg gtg gca gcc    882
Thr Glu Ser Trp Ile Leu Arg Asn Pro Gly Tyr Ala Leu Val Ala Ala
            250                 255                 260 gtc att ggt tgg atg ctt ggg agc aac acc atg cag aga gtt gtg ttt    930
Val Ile Gly Trp Met Leu Gly Ser Asn Thr Met Gln Arg Val Val Phe
        265                 270                 275 gtc gtg cta ttg ctt ttg gtg gcc cca gct tac agc ttt aac tgc ctt    978
Val Val Leu Leu Leu Leu Val Ala Pro Ala Tyr Ser Phe Asn Cys Leu
280                 285                 290 gga atg agc aac aga gac ttc ttg gaa gga gtg tct gga gca aca tgg   1026
Gly Met Ser Asn Arg Asp Phe Leu Glu Gly Val Ser Gly Ala Thr Trp
295                 300                 305                 310 gtg gat ttg gtt ctc gaa ggc gac agc tgc gtg act atc atg tct aag   1074
Val Asp Leu Val Leu Glu Gly Asp Ser Cys Val Thr Ile Met Ser Lys
                315                 320                 325 gac aag cct acc atc gat gtg aag atg atg aat atg gag gcg gcc aac   1122
Asp Lys Pro Thr Ile Asp Val Lys Met Met Asn Met Glu Ala Ala Asn
            330                 335                 340 ctg gca gag gtc cgc agt tat tgc tat ttg gct acc gtc agc gat ctc   1170
Leu Ala Glu Val Arg Ser Tyr Cys Tyr Leu Ala Thr Val Ser Asp Leu
        345                 350                 355 tcc acc aaa gct gcg tgc ccg acc atg gga gaa gct cac aat gac aaa   1218
Ser Thr Lys Ala Ala Cys Pro Thr Met Gly Glu Ala His Asn Asp Lys
360                 365                 370 cgt gct gac cca gct ttt gtg tgc aga caa gga gtg gtg gac agg ggc   1266
Arg Ala Asp Pro Ala Phe Val Cys Arg Gln Gly Val Val Asp Arg Gly
375                 380                 385                 390 tgg ggc aac ggc tgc gga cta ttt ggc aaa gga agc att gac aca tgc   1314
Trp Gly Asn Gly Cys Gly Leu Phe Gly Lys Gly Ser Ile Asp Thr Cys
                395                 400                 405 gcc aaa ttt gcc tgc tct acc aag gca ata gga aga acc atc ttg aaa   1362
Ala Lys Phe Ala Cys Ser Thr Lys Ala Ile Gly Arg Thr Ile Leu Lys
```

-continued

```
             410                 415                 420
gag aat atc aag tac gaa gtg gcc att ttt gtc cat gga cca act act    1410
Glu Asn Ile Lys Tyr Glu Val Ala Ile Phe Val His Gly Pro Thr Thr
            425                 430                 435 gtg gag tcg cac gga aac tac tcc aca cag gtt gga gcc act cag gca    1458
Val Glu Ser His Gly Asn Tyr Ser Thr Gln Val Gly Ala Thr Gln Ala
    440                 445                 450 ggg aga ttc agc atc act cct gcg gcg cct tca tac aca cta aag ctt    1506
Gly Arg Phe Ser Ile Thr Pro Ala Ala Pro Ser Tyr Thr Leu Lys Leu
455                 460                 465                 470 gga gaa tat gga gag gtg aca gtg gac tgt gaa cca cgg tca ggg att    1554
Gly Glu Tyr Gly Glu Val Thr Val Asp Cys Glu Pro Arg Ser Gly Ile
                475                 480                 485 gac acc aat gca tac tac gtg atg act gtt gga aca aag acg ttc ttg    1602
Asp Thr Asn Ala Tyr Tyr Val Met Thr Val Gly Thr Lys Thr Phe Leu
            490                 495                 500 gtc cat cgt gag tgg ttc atg gac ctc aac ctc cct tgg agc agt gct    1650
Val His Arg Glu Trp Phe Met Asp Leu Asn Leu Pro Trp Ser Ser Ala
        505                 510                 515 gga agt act gtg tgg agg aac aga gag acg tta atg gag ttt gag gaa    1698
Gly Ser Thr Val Trp Arg Asn Arg Glu Thr Leu Met Glu Phe Glu Glu
520                 525                 530 cca cac gcc acg aag cag tct gtg ata gca ttg ggc tca caa gag gga    1746
Pro His Ala Thr Lys Gln Ser Val Ile Ala Leu Gly Ser Gln Glu Gly
535                 540                 545                 550 gct ctg cat caa gct ttg gct gga gcc att cct gtg gaa ttt tca agc    1794
Ala Leu His Gln Ala Leu Ala Gly Ala Ile Pro Val Glu Phe Ser Ser
                555                 560                 565 aac act gtc aag ttg acg tcg ggt cat ttg aag tgt aga gtg aag atg    1842
Asn Thr Val Lys Leu Thr Ser Gly His Leu Lys Cys Arg Val Lys Met
            570                 575                 580 gaa aaa ttg cag ttg aag gga aca acc tat ggc gtc tgt tca aag gct    1890
Glu Lys Leu Gln Leu Lys Gly Thr Thr Tyr Gly Val Cys Ser Lys Ala
        585                 590                 595 ttc aag ttt ctt ggg act ccc gca gac aca ggt cac ggc act gtg gtg    1938
Phe Lys Phe Leu Gly Thr Pro Ala Asp Thr Gly His Gly Thr Val Val
600                 605                 610 ttg gaa ttg cag tac act ggc acg gat gga cct tgc aaa gtt cct atc    1986
Leu Glu Leu Gln Tyr Thr Gly Thr Asp Gly Pro Cys Lys Val Pro Ile
615                 620                 625                 630 tcg tca gtg gct tca ttg aac gac cta acg cca gtg ggc aga ttg gtc    2034
Ser Ser Val Ala Ser Leu Asn Asp Leu Thr Pro Val Gly Arg Leu Val
                635                 640                 645 act gtc aac cct ttt gtt tca gtg gcc acg gcc aac gct aag gtc ctg    2082
Thr Val Asn Pro Phe Val Ser Val Ala Thr Ala Asn Ala Lys Val Leu
            650                 655                 660 att gaa ttg gaa cca ccc ttt gga gac tca tac ata gtg gtg ggc aga    2130
Ile Glu Leu Glu Pro Pro Phe Gly Asp Ser Tyr Ile Val Val Gly Arg
        665                 670                 675 gga gaa caa cag att aat cac cat tgg cac aag tct gga agc agc att    2178
Gly Glu Gln Gln Ile Asn His His Trp His Lys Ser Gly Ser Ser Ile
680                 685                 690 ggc aaa gcc ttt aca acc acc ctc aaa gga gcg cag aga cta gcc gct    2226
Gly Lys Ala Phe Thr Thr Thr Leu Lys Gly Ala Gln Arg Leu Ala Ala
695                 700                 705                 710 cta gga gac aca gct tgg gac ttt gga tca gtt gga ggg gtg ttc acc    2274
Leu Gly Asp Thr Ala Trp Asp Phe Gly Ser Val Gly Gly Val Phe Thr
                715                 720                 725 tca gtt ggg aag gct gtc cat caa gtg ttc gga gga gca ttc cgc tca    2322
```

|  |  |
|---|---|
| Ser Val Gly Lys Ala Val His Gln Val Phe Gly Gly Ala Phe Arg Ser<br>            730              735              740 | |
| ctg ttc gga ggc atg tcc tgg ata acg caa gga ttg ctg ggg gct ctc<br>Leu Phe Gly Gly Met Ser Trp Ile Thr Gln Gly Leu Leu Gly Ala Leu<br>        745              750              755 | 2370 |
| ctg ttg tgg atg ggc atc aat gct cgt gat agg tcc ata gct ctc acg<br>Leu Leu Trp Met Gly Ile Asn Ala Arg Asp Arg Ser Ile Ala Leu Thr<br>760                765              770 | 2418 |
| ttt ctc gca gtt gga gga gtt ctg ctc ttc ctc tcc gtg aac gtg cac<br>Phe Leu Ala Val Gly Gly Val Leu Leu Phe Leu Ser Val Asn Val His<br>775                780              785              790 | 2466 |
| gct gac act ggg tgt gcc ata gac atc agc cgg caa gag ctg aga tgt<br>Ala Asp Thr Gly Cys Ala Ile Asp Ile Ser Arg Gln Glu Leu Arg Cys<br>        795              800              805 | 2514 |
| gga aat gga gtg ttc ata cac aat gat gtg gag gct tgg atg gac cgg<br>Gly Asn Gly Val Phe Ile His Asn Asp Val Glu Ala Trp Met Asp Arg<br>            810              815              820 | 2562 |
| tac aag tat tac cct gaa acg cca caa ggc cta gcc aag atc att cag<br>Tyr Lys Tyr Tyr Pro Glu Thr Pro Gln Gly Leu Ala Lys Ile Ile Gln<br>                825              830              835 | 2610 |
| aaa gct cat aag gaa gga gtg tgc ggt cta cga tca gtt tcc aga ctg<br>Lys Ala His Lys Glu Gly Val Cys Gly Leu Arg Ser Val Ser Arg Leu<br>840                845              850 | 2658 |
| gag cat caa atg tgg gaa gca gtg aag gac gag ctg aac act ctt ttg<br>Glu His Gln Met Trp Glu Ala Val Lys Asp Glu Leu Asn Thr Leu Leu<br>855                860              865              870 | 2706 |
| aag gag aat ggt gtg gac ctt agt gtc gtg gtt gag aaa cag gag gga<br>Lys Glu Asn Gly Val Asp Leu Ser Val Val Val Glu Lys Gln Glu Gly<br>            875              880              885 | 2754 |
| atg tac aag tca gca cct aaa cgc ctc acc gcc acc acg gaa aaa ttg<br>Met Tyr Lys Ser Ala Pro Lys Arg Leu Thr Ala Thr Thr Glu Lys Leu<br>        890              895              900 | 2802 |
| gaa att ggc tgg aag gcc tgg gga aag agt att tta ttt gca cca gaa<br>Glu Ile Gly Trp Lys Ala Trp Gly Lys Ser Ile Leu Phe Ala Pro Glu<br>            905              910              915 | 2850 |
| ctc gcc aac aac acc ttt gtg gtt gat ggt ccg gag acc aag gaa tgt<br>Leu Ala Asn Asn Thr Phe Val Val Asp Gly Pro Glu Thr Lys Glu Cys<br>920                925              930 | 2898 |
| ccg act cag aat cgc gct tgg aat agc tta gaa gtg gag gat ttt gga<br>Pro Thr Gln Asn Arg Ala Trp Asn Ser Leu Glu Val Glu Asp Phe Gly<br>935                940              945              950 | 2946 |
| ttt ggt ctc acc agc act cgg atg ttc ctg aag gtc aga gag agc aac<br>Phe Gly Leu Thr Ser Thr Arg Met Phe Leu Lys Val Arg Glu Ser Asn<br>            955              960              965 | 2994 |
| aca act gaa tgt gac tcg aag atc att gga acg gct gtc aag aac aac<br>Thr Thr Glu Cys Asp Ser Lys Ile Ile Gly Thr Ala Val Lys Asn Asn<br>            970              975              980 | 3042 |
| ttg gcg atc cac agt gac ctg tcc tat tgg att gaa agc agg ctc aat<br>Leu Ala Ile His Ser Asp Leu Ser Tyr Trp Ile Glu Ser Arg Leu Asn<br>985                990              995 | 3090 |
| gat acg tgg aag ctt gaa agg gca gtt ctg ggt gaa gtc aaa tca<br>Asp Thr Trp Lys Leu Glu Arg Ala Val Leu Gly Glu Val Lys Ser<br>        1000              1005             1010 | 3135 |
| tgt acg tgg cct gag acg cat acc ttg tgg ggc gat gga atc ctt<br>Cys Thr Trp Pro Glu Thr His Thr Leu Trp Gly Asp Gly Ile Leu<br>        1015              1020             1025 | 3180 |
| gag agt gac ttg ata ata cca gtc aca ctg gcg gga cca cga agc<br>Glu Ser Asp Leu Ile Ile Pro Val Thr Leu Ala Gly Pro Arg Ser<br>        1030              1035             1040 | 3225 |

-continued

| | | | | | | | | | | | | | | |
|---|---|---|---|---|---|---|---|---|---|---|---|---|---|---|
| aat<br>Asn<br>1045 | cac<br>His | aat<br>Asn | cgg<br>Arg | aga<br>Arg | cct<br>Pro<br>1050 | ggg<br>Gly | tac<br>Tyr | aag<br>Lys | aca<br>Thr | caa<br>Gln<br>1055 | aac<br>Asn | cag<br>Gln | ggc<br>Gly | cca<br>Pro | 3270 |
| tgg<br>Trp<br>1060 | gac<br>Asp | gaa<br>Glu | ggc<br>Gly | cgg<br>Arg | gta<br>Val<br>1065 | gag<br>Glu | att<br>Ile | gac<br>Asp | ttc<br>Phe | gat<br>Asp<br>1070 | tac<br>Tyr | tgc<br>Cys | cca<br>Pro | gga<br>Gly | 3315 |
| act<br>Thr<br>1075 | acg<br>Thr | gtc<br>Val | acc<br>Thr | ctg<br>Leu | agt<br>Ser<br>1080 | gag<br>Glu | agc<br>Ser | tgc<br>Cys | gga<br>Gly | cac<br>His<br>1085 | cgt<br>Arg | gga<br>Gly | cct<br>Pro | gcc<br>Ala | 3360 |
| act<br>Thr<br>1090 | cgc<br>Arg | acc<br>Thr | acc<br>Thr | aca<br>Thr | gag<br>Glu<br>1095 | agc<br>Ser | gga<br>Gly | aag<br>Lys | ttg<br>Leu | ata<br>Ile<br>1100 | aca<br>Thr | gat<br>Asp | tgg<br>Trp | tgc<br>Cys | 3405 |
| tgc<br>Cys<br>1105 | agg<br>Arg | agc<br>Ser | tgc<br>Cys | acc<br>Thr | tta<br>Leu<br>1110 | cca<br>Pro | cca<br>Pro | ctg<br>Leu | cgc<br>Arg | tac<br>Tyr<br>1115 | caa<br>Gln | act<br>Thr | gac<br>Asp | agc<br>Ser | 3450 |
| ggc<br>Gly<br>1120 | tgt<br>Cys | tgg<br>Trp | tat<br>Tyr | ggt<br>Gly | atg<br>Met<br>1125 | gag<br>Glu | atc<br>Ile | aga<br>Arg | cca<br>Pro | cag<br>Gln<br>1130 | aga<br>Arg | cat<br>His | gat<br>Asp | gaa<br>Glu | 3495 |
| aag<br>Lys<br>1135 | acc<br>Thr | ctc<br>Leu | gtg<br>Val | cag<br>Gln | tca<br>Ser<br>1140 | caa<br>Gln | gtg<br>Val | aat<br>Asn | gct<br>Ala | tat<br>Tyr<br>1145 | aat<br>Asn | gct<br>Ala | gat<br>Asp | atg<br>Met | 3540 |
| att<br>Ile<br>1150 | gac<br>Asp | cct<br>Pro | ttt<br>Phe | cag<br>Gln | ttg<br>Leu<br>1155 | ggc<br>Gly | ctt<br>Leu | ctg<br>Leu | gtc<br>Val | gtg<br>Val<br>1160 | ttc<br>Phe | ttg<br>Leu | gcc<br>Ala | acc<br>Thr | 3585 |
| cag<br>Gln<br>1165 | gag<br>Glu | gtc<br>Val | ctt<br>Leu | cgc<br>Arg | aag<br>Lys<br>1170 | agg<br>Arg | tgg<br>Trp | aca<br>Thr | gcc<br>Ala | aag<br>Lys<br>1175 | atc<br>Ile | agc<br>Ser | atg<br>Met | cca<br>Pro | 3630 |
| gct<br>Ala<br>1180 | ata<br>Ile | ctg<br>Leu | att<br>Ile | gct<br>Ala | ctg<br>Leu<br>1185 | cta<br>Leu | gtc<br>Val | ctg<br>Leu | gtg<br>Val | ttt<br>Phe<br>1190 | ggg<br>Gly | ggc<br>Gly | att<br>Ile | act<br>Thr | 3675 |
| tac<br>Tyr<br>1195 | act<br>Thr | gat<br>Asp | gtg<br>Val | tta<br>Leu | cgc<br>Arg<br>1200 | tat<br>Tyr | gtc<br>Val | atc<br>Ile | ttg<br>Leu | gtg<br>Val<br>1205 | ggg<br>Gly | gca<br>Ala | gct<br>Ala | ttc<br>Phe | 3720 |
| gca<br>Ala<br>1210 | gaa<br>Glu | tct<br>Ser | aat<br>Asn | tcg<br>Ser | gga<br>Gly<br>1215 | gga<br>Gly | gac<br>Asp | gtg<br>Val | gta<br>Val | cac<br>His<br>1220 | ttg<br>Leu | gcg<br>Ala | ctc<br>Leu | atg<br>Met | 3765 |
| gcg<br>Ala<br>1225 | acc<br>Thr | ttc<br>Phe | aag<br>Lys | ata<br>Ile | caa<br>Gln<br>1230 | cca<br>Pro | gtg<br>Val | ttt<br>Phe | atg<br>Met | gtg<br>Val<br>1235 | gca<br>Ala | tcg<br>Ser | ttt<br>Phe | ctc<br>Leu | 3810 |
| aaa<br>Lys<br>1240 | gcg<br>Ala | aga<br>Arg | tgg<br>Trp | acc<br>Thr | aac<br>Asn<br>1245 | cag<br>Gln | gag<br>Glu | aac<br>Asn | att<br>Ile | ttg<br>Leu<br>1250 | ttg<br>Leu | atg<br>Met | ttg<br>Leu | gcg<br>Ala | 3855 |
| gct<br>Ala<br>1255 | gtt<br>Val | ttc<br>Phe | ttt<br>Phe | caa<br>Gln | atg<br>Met<br>1260 | gct<br>Ala | tat<br>Tyr | cac<br>His | gat<br>Asp | gcc<br>Ala<br>1265 | cgc<br>Arg | caa<br>Gln | att<br>Ile | ctg<br>Leu | 3900 |
| ctc<br>Leu<br>1270 | tgg<br>Trp | gag<br>Glu | atc<br>Ile | cct<br>Pro | gat<br>Asp<br>1275 | gtg<br>Val | ttg<br>Leu | aat<br>Asn | tca<br>Ser | ctg<br>Leu<br>1280 | gcg<br>Ala | gta<br>Val | gct<br>Ala | tgg<br>Trp | 3945 |
| atg<br>Met<br>1285 | ata<br>Ile | ctg<br>Leu | aga<br>Arg | gcc<br>Ala | ata<br>Ile<br>1290 | aca<br>Thr | ttc<br>Phe | aca<br>Thr | acg<br>Thr | aca<br>Thr<br>1295 | tca<br>Ser | aat<br>Asn | gtg<br>Val | gtc<br>Val | 3990 |
| gtc<br>Val<br>1300 | ccg<br>Pro | ctg<br>Leu | cta<br>Leu | gcc<br>Ala | ctg<br>Leu<br>1305 | cta<br>Leu | aca<br>Thr | ccc<br>Pro | cgg<br>Arg | ctg<br>Leu<br>1310 | aga<br>Arg | tgc<br>Cys | ttg<br>Leu | aat<br>Asn | 4035 |
| ctg<br>Leu<br>1315 | gat<br>Asp | gtg<br>Val | tac<br>Tyr | agg<br>Arg | ata<br>Ile<br>1320 | ctg<br>Leu | ctg<br>Leu | ttg<br>Leu | atg<br>Met | gtc<br>Val<br>1325 | gga<br>Gly | ata<br>Ile | ggc<br>Gly | agc<br>Ser | 4080 |
| ttg<br>Leu<br>1330 | atc<br>Ile | agg<br>Arg | gag<br>Glu | aag<br>Lys | agg<br>Arg<br>1335 | agt<br>Ser | gca<br>Ala | gct<br>Ala | gca<br>Ala | aaa<br>Lys<br>1340 | aag<br>Lys | aaa<br>Lys | gga<br>Gly | gca<br>Ala | 4125 |

```
agt ctg cta tgc ttg gct cta gcc tca aca gga ctt ttc aac ccc      4170
Ser Leu Leu Cys Leu Ala Leu Ala Ser Thr Gly Leu Phe Asn Pro
    1345            1350                1355 atg atc ctt gct gct gga ctg att gca tgt gat ccc aac cgt aaa      4215
Met Ile Leu Ala Ala Gly Leu Ile Ala Cys Asp Pro Asn Arg Lys
    1360            1365                1370 cgc gga tgg ccc gca act gaa gtg atg aca gct gtc ggc cta atg      4260
Arg Gly Trp Pro Ala Thr Glu Val Met Thr Ala Val Gly Leu Met
    1375            1380                1385 ttt gcc atc gtc gga ggg ctg gca gag ctt gac att gac tcc atg      4305
Phe Ala Ile Val Gly Gly Leu Ala Glu Leu Asp Ile Asp Ser Met
    1390            1395                1400 gcc att cca atg act atc gcg ggg ctc atg ttt gct gct ttc gtg      4350
Ala Ile Pro Met Thr Ile Ala Gly Leu Met Phe Ala Ala Phe Val
    1405            1410                1415 att tct ggg aaa tca aca gat atg tgg att gag aga acg gcg gac      4395
Ile Ser Gly Lys Ser Thr Asp Met Trp Ile Glu Arg Thr Ala Asp
    1420            1425                1430 att tcc tgg gaa agt gat gca gaa att aca ggc tcg agc gaa aga      4440
Ile Ser Trp Glu Ser Asp Ala Glu Ile Thr Gly Ser Ser Glu Arg
    1435            1440                1445 gtt gat gtt cgg ctt gat gat ggt gaa aac ttc cag ctc atg aat      4485
Val Asp Val Arg Leu Asp Asp Gly Glu Asn Phe Gln Leu Met Asn
    1450            1455                1460 gat cca gga gca cct tgg aag ata tgg atg ctc aga atg gtc tgt      4530
Asp Pro Gly Ala Pro Trp Lys Ile Trp Met Leu Arg Met Val Cys
    1465            1470                1475 ctc gcg att agt gcg tac acc ccc tgg gca atc ttg ccc tca gta      4575
Leu Ala Ile Ser Ala Tyr Thr Pro Trp Ala Ile Leu Pro Ser Val
    1480            1485                1490 gtt gga ttt tgg ata act ctc caa tac aca aag aga gga ggt gtg      4620
Val Gly Phe Trp Ile Thr Leu Gln Tyr Thr Lys Arg Gly Gly Val
    1495            1500                1505 ttg tgg gac act ccc tca cca aag gag tac aaa aag ggg gac acg      4665
Leu Trp Asp Thr Pro Ser Pro Lys Glu Tyr Lys Lys Gly Asp Thr
    1510            1515                1520 acc acc ggc gtc tac agg atc atg act cgt ggg ctg ctc ggc agt      4710
Thr Thr Gly Val Tyr Arg Ile Met Thr Arg Gly Leu Leu Gly Ser
    1525            1530                1535 tat caa gca gga gcg ggc gtg atg gtt gaa ggt gtt ttc cac acc      4755
Tyr Gln Ala Gly Ala Gly Val Met Val Glu Gly Val Phe His Thr
    1540            1545                1550 ctt tgg cat aca aca aaa gga gcc gct ttg atg agc gga gag ggc      4800
Leu Trp His Thr Thr Lys Gly Ala Ala Leu Met Ser Gly Glu Gly
    1555            1560                1565 cgc ctg gac cca tac tgg ggc agt gtc aag gag gat cga ctt tgt      4845
Arg Leu Asp Pro Tyr Trp Gly Ser Val Lys Glu Asp Arg Leu Cys
    1570            1575                1580 tac gga gga ccc tgg aaa ttg cag cac aag tgg aac ggg cag gat      4890
Tyr Gly Gly Pro Trp Lys Leu Gln His Lys Trp Asn Gly Gln Asp
    1585            1590                1595 gag gtg cag atg att gtg gtg gaa cct ggc aag aac gtt aag aac      4935
Glu Val Gln Met Ile Val Val Glu Pro Gly Lys Asn Val Lys Asn
    1600            1605                1610 gtc cag acg aaa cca ggg gtg ttc aaa aca cct gaa gga gaa atc      4980
Val Gln Thr Lys Pro Gly Val Phe Lys Thr Pro Glu Gly Glu Ile
    1615            1620                1625 ggg gcc gtg act ttg gac ttc ccc act gga aca tca ggc tca cca      5025
Gly Ala Val Thr Leu Asp Phe Pro Thr Gly Thr Ser Gly Ser Pro
```

|       |       |       |       |       |       |       |       |       |       |       |       |       |       |       |      |
|---|---|---|---|---|---|---|---|---|---|---|---|---|---|---|---|
|       |       |       | 1630  |       |       |       |       | 1635  |       |       |       |       | 1640  |       |      |
| ata   | gtg   | gac   | aaa   | aac   | ggt   | gat   | gtg   | att   | ggg   | ctt   | tat   | ggc   | aat   | gga   | 5070 |
| Ile   | Val   | Asp   | Lys   | Asn   | Gly   | Asp   | Val   | Ile   | Gly   | Leu   | Tyr   | Gly   | Asn   | Gly   |      |
|       | 1645  |       |       |       |       | 1650  |       |       |       |       | 1655  |       |       |       |      |
| gtc   | ata   | atg   | ccc   | aac   | ggc   | tca   | tac   | ata   | agc   | gcg   | ata   | gtg   | cag   | ggt   | 5115 |
| Val   | Ile   | Met   | Pro   | Asn   | Gly   | Ser   | Tyr   | Ile   | Ser   | Ala   | Ile   | Val   | Gln   | Gly   |      |
|       | 1660  |       |       |       |       | 1665  |       |       |       |       | 1670  |       |       |       |      |
| gaa   | agg   | atg   | gat   | gag   | cca   | atc   | cca   | gcc   | gga   | ttc   | gaa   | cct   | gag   | atg   | 5160 |
| Glu   | Arg   | Met   | Asp   | Glu   | Pro   | Ile   | Pro   | Ala   | Gly   | Phe   | Glu   | Pro   | Glu   | Met   |      |
|       | 1675  |       |       |       |       | 1680  |       |       |       |       | 1685  |       |       |       |      |
| ctg   | agg   | aaa   | aaa   | cag   | atc   | act   | gta   | ctg   | gat   | ctc   | cat   | ccc   | ggc   | gcc   | 5205 |
| Leu   | Arg   | Lys   | Lys   | Gln   | Ile   | Thr   | Val   | Leu   | Asp   | Leu   | His   | Pro   | Gly   | Ala   |      |
|       | 1690  |       |       |       |       | 1695  |       |       |       |       | 1700  |       |       |       |      |
| ggt   | aaa   | aca   | agg   | agg   | att   | ctg   | cca   | cag   | atc   | atc   | aaa   | gag   | gcc   | ata   | 5250 |
| Gly   | Lys   | Thr   | Arg   | Arg   | Ile   | Leu   | Pro   | Gln   | Ile   | Ile   | Lys   | Glu   | Ala   | Ile   |      |
|       | 1705  |       |       |       |       | 1710  |       |       |       |       | 1715  |       |       |       |      |
| aac   | aga   | aga   | ctg   | aga   | aca   | gcc   | gtg   | cta   | gca   | cca   | acc   | agg   | gtt   | gtg   | 5295 |
| Asn   | Arg   | Arg   | Leu   | Arg   | Thr   | Ala   | Val   | Leu   | Ala   | Pro   | Thr   | Arg   | Val   | Val   |      |
|       | 1720  |       |       |       |       | 1725  |       |       |       |       | 1730  |       |       |       |      |
| gct   | gct   | gag   | atg   | gct   | gaa   | gca   | ctg   | aga   | gga   | ctg   | ccc   | atc   | cgg   | tac   | 5340 |
| Ala   | Ala   | Glu   | Met   | Ala   | Glu   | Ala   | Leu   | Arg   | Gly   | Leu   | Pro   | Ile   | Arg   | Tyr   |      |
|       | 1735  |       |       |       |       | 1740  |       |       |       |       | 1745  |       |       |       |      |
| cag   | aca   | tcc   | gca   | gtg   | ccc   | aga   | gaa   | cat   | aat   | gga   | aat   | gag   | att   | gtt   | 5385 |
| Gln   | Thr   | Ser   | Ala   | Val   | Pro   | Arg   | Glu   | His   | Asn   | Gly   | Asn   | Glu   | Ile   | Val   |      |
|       | 1750  |       |       |       |       | 1755  |       |       |       |       | 1760  |       |       |       |      |
| gat   | gtc   | atg   | tgt   | cat   | gct   | acc   | ctc   | acc   | cac   | agg   | ctg   | atg   | tct   | cct   | 5430 |
| Asp   | Val   | Met   | Cys   | His   | Ala   | Thr   | Leu   | Thr   | His   | Arg   | Leu   | Met   | Ser   | Pro   |      |
|       | 1765  |       |       |       |       | 1770  |       |       |       |       | 1775  |       |       |       |      |
| cac   | agg   | gtg   | ccg   | aac   | tac   | aac   | ctg   | ttc   | gtg   | atg   | gat   | gag   | gct   | cat   | 5475 |
| His   | Arg   | Val   | Pro   | Asn   | Tyr   | Asn   | Leu   | Phe   | Val   | Met   | Asp   | Glu   | Ala   | His   |      |
|       | 1780  |       |       |       |       | 1785  |       |       |       |       | 1790  |       |       |       |      |
| ttc   | acc   | gac   | cca   | gct   | agt   | atc   | gca   | gca   | aga   | ggt   | tac   | att   | tcc   | aca   | 5520 |
| Phe   | Thr   | Asp   | Pro   | Ala   | Ser   | Ile   | Ala   | Ala   | Arg   | Gly   | Tyr   | Ile   | Ser   | Thr   |      |
|       | 1795  |       |       |       |       | 1800  |       |       |       |       | 1805  |       |       |       |      |
| aag   | gtc   | gag   | cta   | ggg   | gag   | gcg   | gcg   | gca   | ata   | ttc   | atg   | aca   | gcc   | acc   | 5565 |
| Lys   | Val   | Glu   | Leu   | Gly   | Glu   | Ala   | Ala   | Ala   | Ile   | Phe   | Met   | Thr   | Ala   | Thr   |      |
|       | 1810  |       |       |       |       | 1815  |       |       |       |       | 1820  |       |       |       |      |
| cca   | cca   | ggc   | act   | tca   | gat   | cca   | ttc   | cca   | gag   | tcc   | aat   | tca   | cca   | att   | 5610 |
| Pro   | Pro   | Gly   | Thr   | Ser   | Asp   | Pro   | Phe   | Pro   | Glu   | Ser   | Asn   | Ser   | Pro   | Ile   |      |
|       | 1825  |       |       |       |       | 1830  |       |       |       |       | 1835  |       |       |       |      |
| tcc   | gac   | tta   | cag   | act   | gag   | atc   | ccg   | gat   | cga   | gct   | tgg   | aac   | tct   | gga   | 5655 |
| Ser   | Asp   | Leu   | Gln   | Thr   | Glu   | Ile   | Pro   | Asp   | Arg   | Ala   | Trp   | Asn   | Ser   | Gly   |      |
|       | 1840  |       |       |       |       | 1845  |       |       |       |       | 1850  |       |       |       |      |
| tac   | gaa   | tgg   | atc   | aca   | gaa   | tac   | acc   | ggg   | aag   | acg   | gtt   | tgg   | ttt   | gtg   | 5700 |
| Tyr   | Glu   | Trp   | Ile   | Thr   | Glu   | Tyr   | Thr   | Gly   | Lys   | Thr   | Val   | Trp   | Phe   | Val   |      |
|       | 1855  |       |       |       |       | 1860  |       |       |       |       | 1865  |       |       |       |      |
| cct   | agt   | gtc   | aag   | atg   | ggg   | aat   | gag   | att   | gcc   | ctt   | tgc   | cta   | caa   | cgt   | 5745 |
| Pro   | Ser   | Val   | Lys   | Met   | Gly   | Asn   | Glu   | Ile   | Ala   | Leu   | Cys   | Leu   | Gln   | Arg   |      |
|       | 1870  |       |       |       |       | 1875  |       |       |       |       | 1880  |       |       |       |      |
| gct   | gga   | aag   | aaa   | gta   | gtc   | caa   | ttg   | aac   | aga   | aag   | tcg   | tac   | gag   | acg   | 5790 |
| Ala   | Gly   | Lys   | Lys   | Val   | Val   | Gln   | Leu   | Asn   | Arg   | Lys   | Ser   | Tyr   | Glu   | Thr   |      |
|       | 1885  |       |       |       |       | 1890  |       |       |       |       | 1895  |       |       |       |      |
| gag   | tac   | cca   | aaa   | tgt   | aag   | aac   | gat   | gat   | tgg   | gac   | ttt   | gtt   | atc   | aca   | 5835 |
| Glu   | Tyr   | Pro   | Lys   | Cys   | Lys   | Asn   | Asp   | Asp   | Trp   | Asp   | Phe   | Val   | Ile   | Thr   |      |
|       | 1900  |       |       |       |       | 1905  |       |       |       |       | 1910  |       |       |       |      |
| aca   | gac   | ata   | tct   | gaa   | atg   | ggg   | gct   | aac   | ttc   | aag   | gcg   | agc   | agg   | gtg   | 5880 |
| Thr   | Asp   | Ile   | Ser   | Glu   | Met   | Gly   | Ala   | Asn   | Phe   | Lys   | Ala   | Ser   | Arg   | Val   |      |
|       | 1915  |       |       |       |       | 1920  |       |       |       |       | 1925  |       |       |       |      |
| att   | gac   | agc   | cgg   | aag   | agt   | gtg   | aaa   | cca   | acc   | atc   | ata   | aca   | gaa   | gga   | 5925 |

```
Ile Asp Ser Arg Lys Ser Val Lys Pro Thr Ile Ile Thr Glu Gly
    1930            1935                1940 gaa ggg aga gtg atc ctg gga gaa cca tct gca gtg aca gca gct      5970
Glu Gly Arg Val Ile Leu Gly Glu Pro Ser Ala Val Thr Ala Ala
    1945            1950                1955 agt gcc gcc cag aga cgt gga cgt atc ggt aga aat ccg tcg caa      6015
Ser Ala Ala Gln Arg Arg Gly Arg Ile Gly Arg Asn Pro Ser Gln
    1960            1965                1970 gtt ggt gat gag tac tgt tat ggg ggg cac acg aat gaa gac gac      6060
Val Gly Asp Glu Tyr Cys Tyr Gly Gly His Thr Asn Glu Asp Asp
    1975            1980                1985 tcg aac ttc gcc cat tgg act gag gca cga atc atg ccg gac aac      6105
Ser Asn Phe Ala His Trp Thr Glu Ala Arg Ile Met Pro Asp Asn
    1990            1995                2000 atc aac atg cca aac gga ctg atc gct caa ttc tac caa cca gag      6150
Ile Asn Met Pro Asn Gly Leu Ile Ala Gln Phe Tyr Gln Pro Glu
    2005            2010                2015 cgt gag aag gta tat acc atg gag ggg gaa tac cgg ctc aga gga      6195
Arg Glu Lys Val Tyr Thr Met Glu Gly Glu Tyr Arg Leu Arg Gly
    2020            2025                2030 gaa gag agg aaa aac ttt ctg gaa ctg ttg agg act gca gat ctg      6240
Glu Glu Arg Lys Asn Phe Leu Glu Leu Leu Arg Thr Ala Asp Leu
    2035            2040                2045 cca gtt tgg ctg gct tac aag gtt gca gcg gct gga gtg tca tac      6285
Pro Val Trp Leu Ala Tyr Lys Val Ala Ala Ala Gly Val Ser Tyr
    2050            2055                2060 cac gac cgg agg tgg tgc ttt gat ggt cct agg aca aac aca att      6330
His Asp Arg Arg Trp Cys Phe Asp Gly Pro Arg Thr Asn Thr Ile
    2065            2070                2075 tta gaa gac aac aac gaa gtg gaa gtc atc acg aag ctt ggt gaa      6375
Leu Glu Asp Asn Asn Glu Val Glu Val Ile Thr Lys Leu Gly Glu
    2080            2085                2090 agg aag att ctg agg ccg cgc tgg att gac gcc agg gtg tac tcg      6420
Arg Lys Ile Leu Arg Pro Arg Trp Ile Asp Ala Arg Val Tyr Ser
    2095            2100                2105 gat cac cag gca cta aag gcg ttc aag gac ttc gcc tcg gga aaa      6465
Asp His Gln Ala Leu Lys Ala Phe Lys Asp Phe Ala Ser Gly Lys
    2110            2115                2120 cgt tct cag ata ggg ctc att gag gtt ctg gga aag atg cct gag      6510
Arg Ser Gln Ile Gly Leu Ile Glu Val Leu Gly Lys Met Pro Glu
    2125            2130                2135 cac ttc atg ggg aag aca tgg gaa gca ctt gac acc atg tac gtt      6555
His Phe Met Gly Lys Thr Trp Glu Ala Leu Asp Thr Met Tyr Val
    2140            2145                2150 gtg gcc act gca gag aaa gga gga aga gct cac aga atg gcc ctg      6600
Val Ala Thr Ala Glu Lys Gly Gly Arg Ala His Arg Met Ala Leu
    2155            2160                2165 gag gaa ctg cca gat gct ctt cag aca att gcc ttg att gcc tta      6645
Glu Glu Leu Pro Asp Ala Leu Gln Thr Ile Ala Leu Ile Ala Leu
    2170            2175                2180 ttg agt gtg atg acc atg gga gta ttc ttc ctc ctc atg cag cgg      6690
Leu Ser Val Met Thr Met Gly Val Phe Phe Leu Leu Met Gln Arg
    2185            2190                2195 aag ggc att gga aag ata ggt ttg gga ggc gct gtc ttg gga gtc      6735
Lys Gly Ile Gly Lys Ile Gly Leu Gly Gly Ala Val Leu Gly Val
    2200            2205                2210 gcg acc ttt ttc tgt tgg atg gct gaa gtt cca gga acg aag atc      6780
Ala Thr Phe Phe Cys Trp Met Ala Glu Val Pro Gly Thr Lys Ile
    2215            2220                2225
```

-continued

| | | | | | | | | | | | | | | |
|---|---|---|---|---|---|---|---|---|---|---|---|---|---|---|
| gcc | gga | atg | ttg | ctg | ctc | tcc | ctt | ctc | ttg | atg | att | gtg | cta | att | 6825 |
| Ala | Gly | Met | Leu | Leu | Leu | Ser | Leu | Leu | Leu | Met | Ile | Val | Leu | Ile | |
| 2230 | | | | | 2235 | | | | | 2240 | | | | | |

| | | | | | | | | | | | | | | | |
|---|---|---|---|---|---|---|---|---|---|---|---|---|---|---|---|
| cct | gag | cca | gag | aag | caa | cgt | tcg | cag | aca | gac | aac | cag | cta | gcc | 6870 |
| Pro | Glu | Pro | Glu | Lys | Gln | Arg | Ser | Gln | Thr | Asp | Asn | Gln | Leu | Ala | |
| 2245 | | | | | 2250 | | | | | 2255 | | | | | |

| | | | | | | | | | | | | | | | |
|---|---|---|---|---|---|---|---|---|---|---|---|---|---|---|---|
| gtg | ttc | ctg | att | tgt | gtc | atg | acc | ctt | gtg | agc | gca | gtg | gca | gcc | 6915 |
| Val | Phe | Leu | Ile | Cys | Val | Met | Thr | Leu | Val | Ser | Ala | Val | Ala | Ala | |
| 2260 | | | | | 2265 | | | | | 2270 | | | | | |

| | | | | | | | | | | | | | | | |
|---|---|---|---|---|---|---|---|---|---|---|---|---|---|---|---|
| aac | gag | atg | ggt | tgg | cta | gac | aag | acc | aag | agt | gac | ata | agc | agt | 6960 |
| Asn | Glu | Met | Gly | Trp | Leu | Asp | Lys | Thr | Lys | Ser | Asp | Ile | Ser | Ser | |
| 2275 | | | | | 2280 | | | | | 2285 | | | | | |

| | | | | | | | | | | | | | | | |
|---|---|---|---|---|---|---|---|---|---|---|---|---|---|---|---|
| ttg | ttt | ggg | caa | aga | att | gag | gtc | aag | gag | aat | ttc | agc | atg | gga | 7005 |
| Leu | Phe | Gly | Gln | Arg | Ile | Glu | Val | Lys | Glu | Asn | Phe | Ser | Met | Gly | |
| 2290 | | | | | 2295 | | | | | 2300 | | | | | |

| | | | | | | | | | | | | | | | |
|---|---|---|---|---|---|---|---|---|---|---|---|---|---|---|---|
| gag | ttt | ctt | ctg | gac | ttg | agg | ccg | gca | aca | gcc | tgg | tca | ctg | tac | 7050 |
| Glu | Phe | Leu | Leu | Asp | Leu | Arg | Pro | Ala | Thr | Ala | Trp | Ser | Leu | Tyr | |
| 2305 | | | | | 2310 | | | | | 2315 | | | | | |

| | | | | | | | | | | | | | | | |
|---|---|---|---|---|---|---|---|---|---|---|---|---|---|---|---|
| gct | gtg | aca | aca | gcg | gtc | ctc | act | cca | ctg | cta | aag | cat | ttg | atc | 7095 |
| Ala | Val | Thr | Thr | Ala | Val | Leu | Thr | Pro | Leu | Leu | Lys | His | Leu | Ile | |
| 2320 | | | | | 2325 | | | | | 2330 | | | | | |

| | | | | | | | | | | | | | | | |
|---|---|---|---|---|---|---|---|---|---|---|---|---|---|---|---|
| acg | tca | gat | tac | atc | aac | acc | tca | ttg | acc | tca | ata | aac | gtt | cag | 7140 |
| Thr | Ser | Asp | Tyr | Ile | Asn | Thr | Ser | Leu | Thr | Ser | Ile | Asn | Val | Gln | |
| 2335 | | | | | 2340 | | | | | 2345 | | | | | |

| | | | | | | | | | | | | | | | |
|---|---|---|---|---|---|---|---|---|---|---|---|---|---|---|---|
| gca | agt | gca | cta | ttc | aca | ctc | gcg | cga | ggc | ttc | ccc | ttc | gtc | gat | 7185 |
| Ala | Ser | Ala | Leu | Phe | Thr | Leu | Ala | Arg | Gly | Phe | Pro | Phe | Val | Asp | |
| 2350 | | | | | 2355 | | | | | 2360 | | | | | |

| | | | | | | | | | | | | | | | |
|---|---|---|---|---|---|---|---|---|---|---|---|---|---|---|---|
| gtt | gga | gtg | tcg | gct | ctc | ctg | cta | gca | gcc | gga | tgc | tgg | gga | caa | 7230 |
| Val | Gly | Val | Ser | Ala | Leu | Leu | Leu | Ala | Ala | Gly | Cys | Trp | Gly | Gln | |
| 2365 | | | | | 2370 | | | | | 2375 | | | | | |

| | | | | | | | | | | | | | | | |
|---|---|---|---|---|---|---|---|---|---|---|---|---|---|---|---|
| gtc | acc | ctc | acc | gtt | acg | gta | aca | gcg | gca | aca | ctc | ctt | ttt | tgc | 7275 |
| Val | Thr | Leu | Thr | Val | Thr | Val | Thr | Ala | Ala | Thr | Leu | Leu | Phe | Cys | |
| 2380 | | | | | 2385 | | | | | 2390 | | | | | |

| | | | | | | | | | | | | | | | |
|---|---|---|---|---|---|---|---|---|---|---|---|---|---|---|---|
| cac | tat | gcc | tac | atg | gtt | ccc | ggt | tgg | caa | gct | gag | gca | atg | cgc | 7320 |
| His | Tyr | Ala | Tyr | Met | Val | Pro | Gly | Trp | Gln | Ala | Glu | Ala | Met | Arg | |
| 2395 | | | | | 2400 | | | | | 2405 | | | | | |

| | | | | | | | | | | | | | | | |
|---|---|---|---|---|---|---|---|---|---|---|---|---|---|---|---|
| tca | gcc | cag | cgg | cgg | aca | gcg | gcc | gga | atc | atg | aaa | aac | gct | gta | 7365 |
| Ser | Ala | Gln | Arg | Arg | Thr | Ala | Ala | Gly | Ile | Met | Lys | Asn | Ala | Val | |
| 2410 | | | | | 2415 | | | | | 2420 | | | | | |

| | | | | | | | | | | | | | | | |
|---|---|---|---|---|---|---|---|---|---|---|---|---|---|---|---|
| gtg | gat | ggc | atc | gtg | gcc | acg | gac | gtc | cca | gaa | tta | gag | cgc | acc | 7410 |
| Val | Asp | Gly | Ile | Val | Ala | Thr | Asp | Val | Pro | Glu | Leu | Glu | Arg | Thr | |
| 2425 | | | | | 2430 | | | | | 2435 | | | | | |

| | | | | | | | | | | | | | | | |
|---|---|---|---|---|---|---|---|---|---|---|---|---|---|---|---|
| aca | ccc | atc | atg | cag | aag | aaa | gtt | gga | cag | atc | atg | ctg | atc | ttg | 7455 |
| Thr | Pro | Ile | Met | Gln | Lys | Lys | Val | Gly | Gln | Ile | Met | Leu | Ile | Leu | |
| 2440 | | | | | 2445 | | | | | 2450 | | | | | |

| | | | | | | | | | | | | | | | |
|---|---|---|---|---|---|---|---|---|---|---|---|---|---|---|---|
| gtg | tct | cta | gct | gca | gta | gtg | aac | ccg | tct | gtg | aag | aca | gta | 7500 |
| Val | Ser | Leu | Ala | Ala | Val | Val | Asn | Pro | Ser | Val | Lys | Thr | Val | | |
| 2455 | | | | | 2460 | | | | | 2465 | | | | | |

| | | | | | | | | | | | | | | | |
|---|---|---|---|---|---|---|---|---|---|---|---|---|---|---|---|
| cga | gaa | gcc | gga | att | ttg | atc | acg | gcc | gca | gcg | gtg | acg | ctt | tgg | 7545 |
| Arg | Glu | Ala | Gly | Ile | Leu | Ile | Thr | Ala | Ala | Ala | Val | Thr | Leu | Trp | |
| 2470 | | | | | 2475 | | | | | 2480 | | | | | |

| | | | | | | | | | | | | | | | |
|---|---|---|---|---|---|---|---|---|---|---|---|---|---|---|---|
| gag | aat | gga | gca | agc | tct | gtt | tgg | aac | gca | aca | act | gcc | atc | gga | 7590 |
| Glu | Asn | Gly | Ala | Ser | Ser | Val | Trp | Asn | Ala | Thr | Thr | Ala | Ile | Gly | |
| 2485 | | | | | 2490 | | | | | 2495 | | | | | |

| | | | | | | | | | | | | | | | |
|---|---|---|---|---|---|---|---|---|---|---|---|---|---|---|---|
| ctc | tgc | cac | atc | atg | cgt | ggg | ggt | tgg | ttg | tca | tgt | cta | tcc | ata | 7635 |
| Leu | Cys | His | Ile | Met | Arg | Gly | Gly | Trp | Leu | Ser | Cys | Leu | Ser | Ile | |
| 2500 | | | | | 2505 | | | | | 2510 | | | | | |

| | | | | | | | | | | | | | | | |
|---|---|---|---|---|---|---|---|---|---|---|---|---|---|---|---|
| aca | tgg | aca | ctc | ata | aag | aac | atg | gaa | aaa | cca | gga | cta | aaa | aga | 7680 |
| Thr | Trp | Thr | Leu | Ile | Lys | Asn | Met | Glu | Lys | Pro | Gly | Leu | Lys | Arg | |
| 2515 | | | | | 2520 | | | | | 2525 | | | | | |

| | | | | | | | | | | | |
|---|---|---|---|---|---|---|---|---|---|---|---|
| ggt | ggg | gca | aaa | gga | cgc | acc | ttg | gga | gag | gtt | tgg | aaa | gaa | aga | 7725 |
| Gly | Gly | Ala | Lys | Gly | Arg | Thr | Leu | Gly | Glu | Val | Trp | Lys | Glu | Arg |
| | 2530 | | | | 2535 | | | | | 2540 | | | | | ggt ggg gca aaa gga cgc acc ttg gga gag gtt tgg aaa gaa aga   7725
Gly Gly Ala Lys Gly Arg Thr Leu Gly Glu Val Trp Lys Glu Arg
    2530            2535                2540 ctc aac cag atg aca aaa gaa gag ttc act agg tac cgc aaa gag   7770
Leu Asn Gln Met Thr Lys Glu Glu Phe Thr Arg Tyr Arg Lys Glu
    2545            2550                2555 gcc atc atc gaa gtc gat cgc tca gcg gca aaa cac gcc agg aaa   7815
Ala Ile Ile Glu Val Asp Arg Ser Ala Ala Lys His Ala Arg Lys
    2560            2565                2570 gaa ggc aat gtc act gga ggg cat tca gtc tct agg ggc aca gca   7860
Glu Gly Asn Val Thr Gly Gly His Ser Val Ser Arg Gly Thr Ala
    2575            2580                2585 aaa ctg aga tgg ctg gtc gaa cgg agg ttt ctc gaa ccg gtc gga   7905
Lys Leu Arg Trp Leu Val Glu Arg Arg Phe Leu Glu Pro Val Gly
    2590            2595                2600 aaa gtg att gac ctt gga tgt gga aga ggc ggt tgg tgt tac tat   7950
Lys Val Ile Asp Leu Gly Cys Gly Arg Gly Gly Trp Cys Tyr Tyr
    2605            2610                2615 atg gca acc caa aaa aga gtc caa gaa gtc aga ggg tac aca aag   7995
Met Ala Thr Gln Lys Arg Val Gln Glu Val Arg Gly Tyr Thr Lys
    2620            2625                2630 ggc ggt ccc gga cat gaa gag ccc caa cta gtg caa agt tat gga   8040
Gly Gly Pro Gly His Glu Glu Pro Gln Leu Val Gln Ser Tyr Gly
    2635            2640                2645 tgg aac att gtc acc atg aag agt gga gtg gat gtg ttc tac aga   8085
Trp Asn Ile Val Thr Met Lys Ser Gly Val Asp Val Phe Tyr Arg
    2650            2655                2660 cct tct gag tgt tgt gac acc ctc ctt tgt gac atc gga gag tcc   8130
Pro Ser Glu Cys Cys Asp Thr Leu Leu Cys Asp Ile Gly Glu Ser
    2665            2670                2675 tcg tca agt gct gag gtt gaa gag cat agg acg att cgt gtc ctt   8175
Ser Ser Ser Ala Glu Val Glu Glu His Arg Thr Ile Arg Val Leu
    2680            2685                2690 gaa atg gtt gag gac tgg ctg cac cga ggg cca agg gaa ttt tgc   8220
Glu Met Val Glu Asp Trp Leu His Arg Gly Pro Arg Glu Phe Cys
    2695            2700                2705 gtg aag gtg ctc tgc ccc tac atg ccg aaa gtc ata gag aag atg   8265
Val Lys Val Leu Cys Pro Tyr Met Pro Lys Val Ile Glu Lys Met
    2710            2715                2720 gag ctg ctc caa cgc cgg tat ggg ggg gga ctg gtc aga aac cca   8310
Glu Leu Leu Gln Arg Arg Tyr Gly Gly Gly Leu Val Arg Asn Pro
    2725            2730                2735 ctc tca cgg aat tcc acg cac gag atg tat tgg gtg agt cga gct   8355
Leu Ser Arg Asn Ser Thr His Glu Met Tyr Trp Val Ser Arg Ala
    2740            2745                2750 tca ggc aat gtg gta cat tca gtg aat atg acc agc cag gtg ctc   8400
Ser Gly Asn Val Val His Ser Val Asn Met Thr Ser Gln Val Leu
    2755            2760                2765 cta gga aga atg gaa aaa agg acc tgg aag gga ccc caa tac gag   8445
Leu Gly Arg Met Glu Lys Arg Thr Trp Lys Gly Pro Gln Tyr Glu
    2770            2775                2780 gaa gat gta aac ttg gga agc gga acc agg gcg gtg gga aaa ccc   8490
Glu Asp Val Asn Leu Gly Ser Gly Thr Arg Ala Val Gly Lys Pro
    2785            2790                2795 ctg ctc aac tca gac acc agt aaa atc aac aac agg att gaa cga   8535
Leu Leu Asn Ser Asp Thr Ser Lys Ile Asn Asn Arg Ile Glu Arg
    2800            2805                2810 ctc agg cgt gag tac agt tcg acg tgg cac cac gat gag aac cac   8580
Leu Arg Arg Glu Tyr Ser Ser Thr Trp His His Asp Glu Asn His

```
                2815                    2820                    2825
cca tat aga acc tgg aac tat cac ggc agt tat gat gtg aag ccc            8625
Pro Tyr Arg Thr Trp Asn Tyr His Gly Ser Tyr Asp Val Lys Pro
    2830                    2835                    2840 aca ggc tcc gcc agt tcg ctg gtc aat gga gtg gtc agg ctc ctc            8670
Thr Gly Ser Ala Ser Ser Leu Val Asn Gly Val Val Arg Leu Leu
    2845                    2850                    2855 tca aaa cca tgg gac acc atc acg aat gtt acc acc atg gcc atg            8715
Ser Lys Pro Trp Asp Thr Ile Thr Asn Val Thr Thr Met Ala Met
    2860                    2865                    2870 act gac act act ccc ttc ggg cag cag cga gtg ttc aaa gag aag            8760
Thr Asp Thr Thr Pro Phe Gly Gln Gln Arg Val Phe Lys Glu Lys
    2875                    2880                    2885 gtg gac acg aaa gct cct gaa ccg cca gaa gga gcg aag tac gtg            8805
Val Asp Thr Lys Ala Pro Glu Pro Pro Glu Gly Ala Lys Tyr Val
    2890                    2895                    2900 ctc aac gag acc acc aac tgg ttg tgg gcg ttt ttg gcc aga gaa            8850
Leu Asn Glu Thr Thr Asn Trp Leu Trp Ala Phe Leu Ala Arg Glu
    2905                    2910                    2915 aaa cgt ccc aga atg tgc tct cga gag gaa ttc ata aga aag gtc            8895
Lys Arg Pro Arg Met Cys Ser Arg Glu Glu Phe Ile Arg Lys Val
    2920                    2925                    2930 aac agc aat gca gct ttg ggt gcc atg ttt gaa gag cag aat caa            8940
Asn Ser Asn Ala Ala Leu Gly Ala Met Phe Glu Glu Gln Asn Gln
    2935                    2940                    2945 tgg agg agc gcc aga gaa gca gtt gaa gat cca aaa ttt tgg gag            8985
Trp Arg Ser Ala Arg Glu Ala Val Glu Asp Pro Lys Phe Trp Glu
    2950                    2955                    2960 atg gtg gat gag gag cgc gag gca cat ctg cgg ggg gaa tgt cac            9030
Met Val Asp Glu Glu Arg Glu Ala His Leu Arg Gly Glu Cys His
    2965                    2970                    2975 act tgc att tac aac atg atg gga aag aga gag aaa aaa ccc gga            9075
Thr Cys Ile Tyr Asn Met Met Gly Lys Arg Glu Lys Lys Pro Gly
    2980                    2985                    2990 gag ttc gga aag gcc aag gga agc aga gcc att tgg ttc atg tgg            9120
Glu Phe Gly Lys Ala Lys Gly Ser Arg Ala Ile Trp Phe Met Trp
    2995                    3000                    3005 ctc gga gct cgc ttt ctg gag ttc gag gct ctg ggt ttt ctc aat            9165
Leu Gly Ala Arg Phe Leu Glu Phe Glu Ala Leu Gly Phe Leu Asn
    3010                    3015                    3020 gaa gac cac tgg ctt gga aga aag aac tca gga gga ggt gtc gag            9210
Glu Asp His Trp Leu Gly Arg Lys Asn Ser Gly Gly Gly Val Glu
    3025                    3030                    3035 ggc ttg ggc ctc caa aaa ctg ggt tac atc ctg cgt gaa gtt ggc            9255
Gly Leu Gly Leu Gln Lys Leu Gly Tyr Ile Leu Arg Glu Val Gly
    3040                    3045                    3050 acc cgg cct ggg ggc aag atc tat gct gat gac aca gct ggc tgg            9300
Thr Arg Pro Gly Gly Lys Ile Tyr Ala Asp Asp Thr Ala Gly Trp
    3055                    3060                    3065 gac acc cgc atc acg aga gct gac ttg gaa aat gaa gct aag gtg            9345
Asp Thr Arg Ile Thr Arg Ala Asp Leu Glu Asn Glu Ala Lys Val
    3070                    3075                    3080 ctt gag ctg ctt gat ggg gaa cat cgg cgt ctt gcc agg gcc atc            9390
Leu Glu Leu Leu Asp Gly Glu His Arg Arg Leu Ala Arg Ala Ile
    3085                    3090                    3095 att gag ctc acc tat cgt cac aaa gtt gtg aaa gtg atg cgc ccg            9435
Ile Glu Leu Thr Tyr Arg His Lys Val Val Lys Val Met Arg Pro
    3100                    3105                    3110 gct gct gat gga aga acc gtc atg gat gtt atc tcc aga gaa gat            9480
```

|   |   |   |   |   |   |   |   |   |   |   |   |   |   |   |
|---|---|---|---|---|---|---|---|---|---|---|---|---|---|---|
| Ala | Ala<br>3115 | Asp | Gly | Arg | Thr<br>3120 | Val | Met | Asp | Val | Ile<br>3125 | Ser | Arg | Glu | Asp |

| cag<br>Gln | agg<br>Arg<br>3130 | ggg<br>Gly | agt<br>Ser | gga<br>Gly | caa<br>Gln<br>3135 | gtt<br>Val | gtc<br>Val | acc<br>Thr | tac<br>Tyr | gcc<br>Ala<br>3140 | cta<br>Leu | aac<br>Asn | act<br>Thr | ttc<br>Phe | 9525 |

| acc<br>Thr | aac<br>Asn<br>3145 | ctg<br>Leu | gcc<br>Ala | gtc<br>Val | cag<br>Gln<br>3150 | ctg<br>Leu | gtg<br>Val | agg<br>Arg | atg<br>Met | atg<br>Met<br>3155 | gaa<br>Glu | ggg<br>Gly | gaa<br>Glu | gga<br>Gly | 9570 |

| gtg<br>Val | att<br>Ile<br>3160 | ggc<br>Gly | cca<br>Pro | gat<br>Asp | gat<br>Asp<br>3165 | gtg<br>Val | gag<br>Glu | aaa<br>Lys | ctc<br>Leu | aca<br>Thr<br>3170 | aaa<br>Lys | ggg<br>Gly | aaa<br>Lys | gga<br>Gly | 9615 |

| ccc<br>Pro | aaa<br>Lys<br>3175 | gtc<br>Val | agg<br>Arg | acc<br>Thr | tgg<br>Trp<br>3180 | ctg<br>Leu | ttt<br>Phe | gag<br>Glu | aat<br>Asn | ggg<br>Gly<br>3185 | gaa<br>Glu | gaa<br>Glu | aga<br>Arg | ctc<br>Leu | 9660 |

| agc<br>Ser | cgc<br>Arg<br>3190 | atg<br>Met | gct<br>Ala | gtc<br>Val | agt<br>Ser<br>3195 | gga<br>Gly | gat<br>Asp | gac<br>Asp | tgt<br>Cys | gtg<br>Val<br>3200 | gta<br>Val | aag<br>Lys | ccc<br>Pro | ctg<br>Leu | 9705 |

| gac<br>Asp | gat<br>Asp<br>3205 | cgc<br>Arg | ttt<br>Phe | gcc<br>Ala | acc<br>Thr<br>3210 | tcg<br>Ser | ctc<br>Leu | cac<br>His | ttc<br>Phe | ctc<br>Leu<br>3215 | aat<br>Asn | gct<br>Ala | atg<br>Met | tca<br>Ser | 9750 |

| aag<br>Lys | gtt<br>Val<br>3220 | cgc<br>Arg | aaa<br>Lys | gac<br>Asp | atc<br>Ile<br>3225 | caa<br>Gln | gag<br>Glu | tgg<br>Trp | aaa<br>Lys | ccg<br>Pro<br>3230 | tca<br>Ser | act<br>Thr | gga<br>Gly | tgg<br>Trp | 9795 |

| tat<br>Tyr | gat<br>Asp<br>3235 | tgg<br>Trp | cag<br>Gln | cag<br>Gln | gtt<br>Val<br>3240 | cca<br>Pro | ttt<br>Phe | tgc<br>Cys | tca<br>Ser | aac<br>Asn<br>3245 | cat<br>His | ttc<br>Phe | act<br>Thr | gaa<br>Glu | 9840 |

| ttg<br>Leu | atc<br>Ile<br>3250 | atg<br>Met | aaa<br>Lys | gat<br>Asp | gga<br>Gly<br>3255 | aga<br>Arg | aca<br>Thr | ctg<br>Leu | gtg<br>Val | gtt<br>Val<br>3260 | cca<br>Pro | tgc<br>Cys | cga<br>Arg | gga<br>Gly | 9885 |

| cag<br>Gln | gat<br>Asp<br>3265 | gaa<br>Glu | ttg<br>Leu | gta<br>Val | ggc<br>Gly<br>3270 | aga<br>Arg | gct<br>Ala | cgc<br>Arg | ata<br>Ile | tct<br>Ser<br>3275 | cca<br>Pro | ggg<br>Gly | gcc<br>Ala | gga<br>Gly | 9930 |

| tgg<br>Trp | aac<br>Asn<br>3280 | gtc<br>Val | cgc<br>Arg | gac<br>Asp | act<br>Thr<br>3285 | gct<br>Ala | tgt<br>Cys | ctg<br>Leu | gct<br>Ala | aag<br>Lys<br>3290 | tct<br>Ser | tat<br>Tyr | gcc<br>Ala | cag<br>Gln | 9975 |

| atg<br>Met | tgg<br>Trp<br>3295 | ctg<br>Leu | ctt<br>Leu | ctg<br>Leu | tac<br>Tyr<br>3300 | ttc<br>Phe | cac<br>His | aga<br>Arg | aga<br>Arg | gac<br>Asp<br>3305 | ctg<br>Leu | cgg<br>Arg | ctc<br>Leu | atg<br>Met | 10020 |

| gcc<br>Ala | aac<br>Asn<br>3310 | gcc<br>Ala | att<br>Ile | tgc<br>Cys | tcc<br>Ser<br>3315 | gct<br>Ala | gtc<br>Val | cct<br>Pro | gtg<br>Val | aat<br>Asn<br>3320 | tgg<br>Trp | gtc<br>Val | cct<br>Pro | acc<br>Thr | 10065 |

| gga<br>Gly | aga<br>Arg<br>3325 | acc<br>Thr | acg<br>Thr | tgg<br>Trp | tcc<br>Ser<br>3330 | atc<br>Ile | cat<br>His | gca<br>Ala | gga<br>Gly | gga<br>Gly<br>3335 | gag<br>Glu | tgg<br>Trp | atg<br>Met | aca<br>Thr | 10110 |

| aca<br>Thr | gag<br>Glu<br>3340 | gac<br>Asp | atg<br>Met | ttg<br>Leu | gag<br>Glu<br>3345 | gtc<br>Val | tgg<br>Trp | aac<br>Asn | cgt<br>Arg | gtt<br>Val<br>3350 | tgg<br>Trp | ata<br>Ile | gag<br>Glu | gag<br>Glu | 10155 |

| aat<br>Asn | gaa<br>Glu<br>3355 | tgg<br>Trp | atg<br>Met | gaa<br>Glu | gac<br>Asp<br>3360 | aaa<br>Lys | acc<br>Thr | cca<br>Pro | gtg<br>Val | gag<br>Glu<br>3365 | aaa<br>Lys | tgg<br>Trp | agt<br>Ser | gac<br>Asp | 10200 |

| gtc<br>Val | cca<br>Pro<br>3370 | tat<br>Tyr | tca<br>Ser | gga<br>Gly | aaa<br>Lys<br>3375 | cga<br>Arg | gag<br>Glu | gac<br>Asp | atc<br>Ile | tgg<br>Trp<br>3380 | tgt<br>Cys | ggc<br>Gly | agc<br>Ser | ctg<br>Leu | 10245 |

| att<br>Ile | ggc<br>Gly<br>3385 | aca<br>Thr | aga<br>Arg | gcc<br>Ala | cga<br>Arg<br>3390 | gcc<br>Ala | acg<br>Thr | tgg<br>Trp | gca<br>Ala | gaa<br>Glu<br>3395 | aac<br>Asn | atc<br>Ile | cag<br>Gln | gtg<br>Val | 10290 |

| gct<br>Ala | atc<br>Ile<br>3400 | aac<br>Asn | caa<br>Gln | gtc<br>Val | aga<br>Arg<br>3405 | gca<br>Ala | atc<br>Ile | atc<br>Ile | gga<br>Gly | gat<br>Asp<br>3410 | gag<br>Glu | aag<br>Lys | tat<br>Tyr | gtg<br>Val | 10335 |

-continued

```
gat tac  atg agt tca cta aag  aga tat gaa gac aca  act ttg gtt      10380
Asp Tyr  Met Ser Ser Leu Lys  Arg Tyr Glu Asp Thr  Thr Leu Val
    3415                 3420                 3425 gag gac  aca gta ctg tagatattta atcaattgta aatagacaat ataagtatgc   10435
Glu Asp  Thr Val Leu
    3430 ataaaagtgt agttttatag tagtatttag tggtgttagt gtaaatagtt aagaaaattt  10495 tgaggagaaa gtcaggccgg gaagttcccg ccaccggaag ttgagtagac ggtgctgcct  10555 gcgactcaac cccaggagga ctgggtgaac aaagccgcga agtgatccat gtaagccctc  10615 agaaccgtct cggaaggagg accccacatg ttgtaacttc aaagcccaat gtcagaccac  10675 gctacggcgt gctactctgc ggagagtgca gtctgcgata gtgccccagg aggactgggt  10735 taacaaaggc aaaccaacgc cccacgcggc cctagccccg gtaatggtgt taaccagggc  10795 gaaaggacta gaggttagag gagaccccgc ggtttaaagt gcacggccca gcctgactga  10855 agctgtaggt caggggaagg actagaggtt agtggagacc ccgtgccaca aaacaccaca  10915 acaaaacagc atattgacac ctgggataga ctaggagatc ttctgctctg cacaaccagc  10975 cacacggcac agtgcgccga caatggtggc tggtggtgcg agaacacagg atct        11029

<210> SEQ ID NO 2
<211> LENGTH: 3433
<212> TYPE: PRT
<213> ORGANISM: Flavivirus sp.

<400> SEQUENCE: 2

Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
            100                 105                 110

Val Met Ile Gly Leu Ile Ala Ser Val Gly Ala Val Thr Leu Ser Asn
        115                 120                 125

Phe Gln Gly Lys Val Met Met Thr Val Asn Ala Thr Asp Val Thr Asp
    130                 135                 140

Val Ile Thr Ile Pro Thr Ala Ala Gly Lys Asn Leu Cys Ile Val Arg
145                 150                 155                 160

Ala Met Asp Val Gly Tyr Met Cys Asp Asp Thr Ile Thr Tyr Glu Cys
                165                 170                 175

Pro Val Leu Ser Ala Gly Asn Asp Pro Glu Asp Ile Asp Cys Trp Cys
            180                 185                 190

Thr Lys Ser Ala Val Tyr Val Arg Tyr Gly Arg Cys Thr Lys Thr Arg
        195                 200                 205

His Ser Arg Arg Ser Arg Arg Ser Leu Thr Val Gln Thr His Gly Glu
    210                 215                 220

Ser Thr Leu Ala Asn Lys Lys Gly Ala Trp Met Asp Ser Thr Lys Ala
```

```
                    225                 230                 235                 240

Thr Arg Tyr Leu Val Lys Thr Glu Ser Trp Ile Leu Arg Asn Pro Gly
                            245                 250                 255

Tyr Ala Leu Val Ala Val Ile Gly Trp Met Leu Gly Ser Asn Thr
                        260                 265                 270

Met Gln Arg Val Val Phe Val Leu Leu Leu Val Ala Pro Ala
                    275                 280                 285

Tyr Ser Phe Asn Cys Leu Gly Met Ser Asn Arg Asp Phe Leu Glu Gly
                290                 295                 300

Val Ser Gly Ala Thr Trp Val Asp Leu Val Leu Glu Gly Asp Ser Cys
            305                 310                 315                 320

Val Thr Ile Met Ser Lys Asp Lys Pro Thr Ile Asp Val Lys Met Met
                            325                 330                 335

Asn Met Glu Ala Ala Asn Leu Ala Glu Val Arg Ser Tyr Cys Tyr Leu
                        340                 345                 350

Ala Thr Val Ser Asp Leu Ser Thr Lys Ala Ala Cys Pro Thr Met Gly
                    355                 360                 365

Glu Ala His Asn Asp Lys Arg Ala Asp Pro Ala Phe Val Cys Arg Gln
                370                 375                 380

Gly Val Val Asp Arg Gly Trp Gly Asn Gly Cys Gly Leu Phe Gly Lys
            385                 390                 395                 400

Gly Ser Ile Asp Thr Cys Ala Lys Phe Ala Cys Ser Thr Lys Ala Ile
                            405                 410                 415

Gly Arg Thr Ile Leu Lys Glu Asn Ile Lys Tyr Glu Val Ala Ile Phe
                        420                 425                 430

Val His Gly Pro Thr Thr Val Glu Ser His Gly Asn Tyr Ser Thr Gln
                    435                 440                 445

Val Gly Ala Thr Gln Ala Gly Arg Phe Ser Ile Thr Pro Ala Ala Pro
                450                 455                 460

Ser Tyr Thr Leu Lys Leu Gly Glu Tyr Gly Glu Val Thr Val Asp Cys
            465                 470                 475                 480

Glu Pro Arg Ser Gly Ile Asp Thr Asn Ala Tyr Tyr Val Met Thr Val
                            485                 490                 495

Gly Thr Lys Thr Phe Leu Val His Arg Glu Trp Phe Met Asp Leu Asn
                        500                 505                 510

Leu Pro Trp Ser Ser Ala Gly Ser Thr Val Trp Arg Asn Arg Glu Thr
                    515                 520                 525

Leu Met Glu Phe Glu Glu Pro His Ala Thr Lys Gln Ser Val Ile Ala
                530                 535                 540

Leu Gly Ser Gln Glu Gly Ala Leu His Gln Ala Leu Ala Gly Ala Ile
            545                 550                 555                 560

Pro Val Glu Phe Ser Ser Asn Thr Val Lys Leu Thr Ser Gly His Leu
                            565                 570                 575

Lys Cys Arg Val Lys Met Glu Lys Leu Gln Leu Lys Gly Thr Thr Tyr
                        580                 585                 590

Gly Val Cys Ser Lys Ala Phe Lys Phe Leu Gly Thr Pro Ala Asp Thr
                    595                 600                 605

Gly His Gly Thr Val Val Leu Glu Leu Gln Tyr Thr Gly Thr Asp Gly
                610                 615                 620

Pro Cys Lys Val Pro Ile Ser Ser Val Ala Ser Leu Asn Asp Leu Thr
            625                 630                 635                 640

Pro Val Gly Arg Leu Val Thr Val Asn Pro Phe Val Ser Val Ala Thr
                            645                 650                 655
```

-continued

```
Ala Asn Ala Lys Val Leu Ile Glu Leu Glu Pro Pro Phe Gly Asp Ser
            660                 665                 670

Tyr Ile Val Val Gly Arg Gly Glu Gln Gln Ile Asn His His Trp His
        675                 680                 685

Lys Ser Gly Ser Ser Ile Gly Lys Ala Phe Thr Thr Thr Leu Lys Gly
    690                 695                 700

Ala Gln Arg Leu Ala Ala Leu Gly Asp Thr Ala Trp Asp Phe Gly Ser
705                 710                 715                 720

Val Gly Gly Val Phe Thr Ser Val Gly Lys Ala Val His Gln Val Phe
                725                 730                 735

Gly Gly Ala Phe Arg Ser Leu Phe Gly Gly Met Ser Trp Ile Thr Gln
            740                 745                 750

Gly Leu Leu Gly Ala Leu Leu Leu Trp Met Gly Ile Asn Ala Arg Asp
        755                 760                 765

Arg Ser Ile Ala Leu Thr Phe Leu Ala Val Gly Gly Val Leu Leu Phe
    770                 775                 780

Leu Ser Val Asn Val His Ala Asp Thr Gly Cys Ala Ile Asp Ile Ser
785                 790                 795                 800

Arg Gln Glu Leu Arg Cys Gly Asn Gly Val Phe Ile His Asn Asp Val
                805                 810                 815

Glu Ala Trp Met Asp Arg Tyr Lys Tyr Tyr Pro Glu Thr Pro Gln Gly
            820                 825                 830

Leu Ala Lys Ile Ile Gln Lys Ala His Lys Glu Gly Val Cys Gly Leu
        835                 840                 845

Arg Ser Val Ser Arg Leu Glu His Gln Met Trp Glu Ala Val Lys Asp
    850                 855                 860

Glu Leu Asn Thr Leu Leu Lys Glu Asn Gly Val Asp Leu Ser Val Val
865                 870                 875                 880

Val Glu Lys Gln Glu Gly Met Tyr Lys Ser Ala Pro Lys Arg Leu Thr
                885                 890                 895

Ala Thr Thr Glu Lys Leu Glu Ile Gly Trp Lys Ala Trp Gly Lys Ser
            900                 905                 910

Ile Leu Phe Ala Pro Glu Leu Ala Asn Asn Thr Phe Val Val Asp Gly
        915                 920                 925

Pro Glu Thr Lys Glu Cys Pro Thr Gln Asn Arg Ala Trp Asn Ser Leu
    930                 935                 940

Glu Val Glu Asp Phe Gly Phe Gly Leu Thr Ser Thr Arg Met Phe Leu
945                 950                 955                 960

Lys Val Arg Glu Ser Asn Thr Thr Glu Cys Asp Ser Lys Ile Ile Gly
                965                 970                 975

Thr Ala Val Lys Asn Asn Leu Ala Ile His Ser Asp Leu Ser Tyr Trp
            980                 985                 990

Ile Glu Ser Arg Leu Asn Asp Thr Trp Lys Leu Glu Arg Ala Val Leu
        995                 1000                1005

Gly Glu Val Lys Ser Cys Thr Trp Pro Glu Thr His Thr Leu Trp
    1010                1015                1020

Gly Asp Gly Ile Leu Glu Ser Asp Leu Ile Ile Pro Val Thr Leu
    1025                1030                1035

Ala Gly Pro Arg Ser Asn His Asn Arg Arg Pro Gly Tyr Lys Thr
    1040                1045                1050

Gln Asn Gln Gly Pro Trp Asp Glu Gly Arg Val Glu Ile Asp Phe
    1055                1060                1065
```

```
Asp Tyr Cys Pro Gly Thr Thr Val Thr Leu Ser Glu Ser Cys Gly
    1070             1075             1080

His Arg Gly Pro Ala Thr Arg Thr Thr Thr Glu Ser Gly Lys Leu
    1085             1090             1095

Ile Thr Asp Trp Cys Cys Arg Ser Cys Thr Leu Pro Pro Leu Arg
    1100             1105             1110

Tyr Gln Thr Asp Ser Gly Cys Trp Tyr Gly Met Glu Ile Arg Pro
    1115             1120             1125

Gln Arg His Asp Glu Lys Thr Leu Val Gln Ser Gln Val Asn Ala
    1130             1135             1140

Tyr Asn Ala Asp Met Ile Asp Pro Phe Gln Leu Gly Leu Leu Val
    1145             1150             1155

Val Phe Leu Ala Thr Gln Glu Val Leu Arg Lys Arg Trp Thr Ala
    1160             1165             1170

Lys Ile Ser Met Pro Ala Ile Leu Ile Ala Leu Leu Val Leu Val
    1175             1180             1185

Phe Gly Gly Ile Thr Tyr Thr Asp Val Leu Arg Tyr Val Ile Leu
    1190             1195             1200

Val Gly Ala Ala Phe Ala Glu Ser Asn Ser Gly Gly Asp Val Val
    1205             1210             1215

His Leu Ala Leu Met Ala Thr Phe Lys Ile Gln Pro Val Phe Met
    1220             1225             1230

Val Ala Ser Phe Leu Lys Ala Arg Trp Thr Asn Gln Glu Asn Ile
    1235             1240             1245

Leu Leu Met Leu Ala Ala Val Phe Phe Gln Met Ala Tyr His Asp
    1250             1255             1260

Ala Arg Gln Ile Leu Leu Trp Glu Ile Pro Asp Val Leu Asn Ser
    1265             1270             1275

Leu Ala Val Ala Trp Met Ile Leu Arg Ala Ile Thr Phe Thr Thr
    1280             1285             1290

Thr Ser Asn Val Val Pro Leu Leu Ala Leu Leu Thr Pro Arg
    1295             1300             1305

Leu Arg Cys Leu Asn Leu Asp Val Tyr Arg Ile Leu Leu Leu Met
    1310             1315             1320

Val Gly Ile Gly Ser Leu Ile Arg Glu Lys Arg Ser Ala Ala Ala
    1325             1330             1335

Lys Lys Lys Gly Ala Ser Leu Leu Cys Leu Ala Leu Ala Ser Thr
    1340             1345             1350

Gly Leu Phe Asn Pro Met Ile Leu Ala Ala Gly Leu Ile Ala Cys
    1355             1360             1365

Asp Pro Asn Arg Lys Arg Gly Trp Pro Ala Thr Glu Val Met Thr
    1370             1375             1380

Ala Val Gly Leu Met Phe Ala Ile Val Gly Gly Leu Ala Glu Leu
    1385             1390             1395

Asp Ile Asp Ser Met Ala Ile Pro Met Thr Ile Ala Gly Leu Met
    1400             1405             1410

Phe Ala Ala Phe Val Ile Ser Gly Lys Ser Thr Asp Met Trp Ile
    1415             1420             1425

Glu Arg Thr Ala Asp Ile Ser Trp Glu Ser Asp Ala Glu Ile Thr
    1430             1435             1440

Gly Ser Ser Glu Arg Val Asp Val Arg Leu Asp Asp Gly Glu Asn
    1445             1450             1455

Phe Gln Leu Met Asn Asp Pro Gly Ala Pro Trp Lys Ile Trp Met
```

```
                1460                1465                1470
Leu Arg Met Val Cys Leu Ala Ile Ser Ala Tyr Thr Pro Trp Ala
    1475                1480                1485
Ile Leu Pro Ser Val Val Gly Phe Trp Ile Thr Leu Gln Tyr Thr
    1490                1495                1500
Lys Arg Gly Gly Val Leu Trp Asp Thr Pro Ser Pro Lys Glu Tyr
    1505                1510                1515
Lys Lys Gly Asp Thr Thr Thr Gly Val Tyr Arg Ile Met Thr Arg
    1520                1525                1530
Gly Leu Leu Gly Ser Tyr Gln Ala Gly Ala Gly Val Met Val Glu
    1535                1540                1545
Gly Val Phe His Thr Leu Trp His Thr Thr Lys Gly Ala Ala Leu
    1550                1555                1560
Met Ser Gly Glu Gly Arg Leu Asp Pro Tyr Trp Gly Ser Val Lys
    1565                1570                1575
Glu Asp Arg Leu Cys Tyr Gly Gly Pro Trp Lys Leu Gln His Lys
    1580                1585                1590
Trp Asn Gly Gln Asp Glu Val Gln Met Ile Val Val Glu Pro Gly
    1595                1600                1605
Lys Asn Val Lys Asn Val Gln Thr Lys Pro Gly Val Phe Lys Thr
    1610                1615                1620
Pro Glu Gly Glu Ile Gly Ala Val Thr Leu Asp Phe Pro Thr Gly
    1625                1630                1635
Thr Ser Gly Ser Pro Ile Val Asp Lys Asn Gly Asp Val Ile Gly
    1640                1645                1650
Leu Tyr Gly Asn Gly Val Ile Met Pro Asn Gly Ser Tyr Ile Ser
    1655                1660                1665
Ala Ile Val Gln Gly Glu Arg Met Asp Glu Pro Ile Pro Ala Gly
    1670                1675                1680
Phe Glu Pro Glu Met Leu Arg Lys Lys Gln Ile Thr Val Leu Asp
    1685                1690                1695
Leu His Pro Gly Ala Gly Lys Thr Arg Arg Ile Leu Pro Gln Ile
    1700                1705                1710
Ile Lys Glu Ala Ile Asn Arg Arg Leu Arg Thr Ala Val Leu Ala
    1715                1720                1725
Pro Thr Arg Val Val Ala Ala Glu Met Ala Glu Ala Leu Arg Gly
    1730                1735                1740
Leu Pro Ile Arg Tyr Gln Thr Ser Ala Val Pro Arg Glu His Asn
    1745                1750                1755
Gly Asn Glu Ile Val Asp Val Met Cys His Ala Thr Leu Thr His
    1760                1765                1770
Arg Leu Met Ser Pro His Arg Val Pro Asn Tyr Asn Leu Phe Val
    1775                1780                1785
Met Asp Glu Ala His Phe Thr Asp Pro Ala Ser Ile Ala Ala Arg
    1790                1795                1800
Gly Tyr Ile Ser Thr Lys Val Glu Leu Gly Glu Ala Ala Ala Ile
    1805                1810                1815
Phe Met Thr Ala Thr Pro Pro Gly Thr Ser Asp Pro Phe Pro Glu
    1820                1825                1830
Ser Asn Ser Pro Ile Ser Asp Leu Gln Thr Glu Ile Pro Asp Arg
    1835                1840                1845
Ala Trp Asn Ser Gly Tyr Glu Trp Ile Thr Glu Tyr Thr Gly Lys
    1850                1855                1860
```

```
Thr Val Trp Phe Val Pro Ser Val Lys Met Gly Asn Glu Ile Ala
    1865            1870            1875

Leu Cys Leu Gln Arg Ala Gly Lys Lys Val Val Gln Leu Asn Arg
    1880            1885            1890

Lys Ser Tyr Glu Thr Glu Tyr Pro Lys Cys Lys Asn Asp Asp Trp
    1895            1900            1905

Asp Phe Val Ile Thr Thr Asp Ile Ser Glu Met Gly Ala Asn Phe
    1910            1915            1920

Lys Ala Ser Arg Val Ile Asp Ser Arg Lys Ser Val Lys Pro Thr
    1925            1930            1935

Ile Ile Thr Glu Gly Glu Gly Arg Val Ile Leu Gly Glu Pro Ser
    1940            1945            1950

Ala Val Thr Ala Ala Ser Ala Ala Gln Arg Arg Gly Arg Ile Gly
    1955            1960            1965

Arg Asn Pro Ser Gln Val Gly Asp Glu Tyr Cys Tyr Gly Gly His
    1970            1975            1980

Thr Asn Glu Asp Asp Ser Asn Phe Ala His Trp Thr Glu Ala Arg
    1985            1990            1995

Ile Met Pro Asp Asn Ile Asn Met Pro Asn Gly Leu Ile Ala Gln
    2000            2005            2010

Phe Tyr Gln Pro Glu Arg Glu Lys Val Tyr Thr Met Glu Gly Glu
    2015            2020            2025

Tyr Arg Leu Arg Gly Glu Glu Arg Lys Asn Phe Leu Glu Leu Leu
    2030            2035            2040

Arg Thr Ala Asp Leu Pro Val Trp Leu Ala Tyr Lys Val Ala Ala
    2045            2050            2055

Ala Gly Val Ser Tyr His Asp Arg Arg Trp Cys Phe Asp Gly Pro
    2060            2065            2070

Arg Thr Asn Thr Ile Leu Glu Asp Asn Asn Glu Val Glu Val Ile
    2075            2080            2085

Thr Lys Leu Gly Glu Arg Lys Ile Leu Arg Pro Arg Trp Ile Asp
    2090            2095            2100

Ala Arg Val Tyr Ser Asp His Gln Ala Leu Lys Ala Phe Lys Asp
    2105            2110            2115

Phe Ala Ser Gly Lys Arg Ser Gln Ile Gly Leu Ile Glu Val Leu
    2120            2125            2130

Gly Lys Met Pro Glu His Phe Met Gly Lys Thr Trp Glu Ala Leu
    2135            2140            2145

Asp Thr Met Tyr Val Val Ala Thr Ala Glu Lys Gly Gly Arg Ala
    2150            2155            2160

His Arg Met Ala Leu Glu Glu Leu Pro Asp Ala Leu Gln Thr Ile
    2165            2170            2175

Ala Leu Ile Ala Leu Leu Ser Val Met Thr Met Gly Val Phe Phe
    2180            2185            2190

Leu Leu Met Gln Arg Lys Gly Ile Gly Lys Ile Gly Leu Gly Gly
    2195            2200            2205

Ala Val Leu Gly Val Ala Thr Phe Phe Cys Trp Met Ala Glu Val
    2210            2215            2220

Pro Gly Thr Lys Ile Ala Gly Met Leu Leu Leu Ser Leu Leu Leu
    2225            2230            2235

Met Ile Val Leu Ile Pro Glu Pro Glu Lys Gln Arg Ser Gln Thr
    2240            2245            2250
```

-continued

```
Asp Asn Gln Leu Ala Val Phe Leu Ile Cys Val Met Thr Leu Val
2255                2260                2265

Ser Ala Val Ala Ala Asn Glu Met Gly Trp Leu Asp Lys Thr Lys
2270                2275                2280

Ser Asp Ile Ser Ser Leu Phe Gly Gln Arg Ile Glu Val Lys Glu
2285                2290                2295

Asn Phe Ser Met Gly Glu Phe Leu Leu Asp Leu Arg Pro Ala Thr
2300                2305                2310

Ala Trp Ser Leu Tyr Ala Val Thr Thr Ala Val Leu Thr Pro Leu
2315                2320                2325

Leu Lys His Leu Ile Thr Ser Asp Tyr Ile Asn Thr Ser Leu Thr
2330                2335                2340

Ser Ile Asn Val Gln Ala Ser Ala Leu Phe Thr Leu Ala Arg Gly
2345                2350                2355

Phe Pro Phe Val Asp Val Gly Val Ser Ala Leu Leu Leu Ala Ala
2360                2365                2370

Gly Cys Trp Gly Gln Val Thr Leu Thr Val Thr Val Thr Ala Ala
2375                2380                2385

Thr Leu Leu Phe Cys His Tyr Ala Tyr Met Val Pro Gly Trp Gln
2390                2395                2400

Ala Glu Ala Met Arg Ser Ala Gln Arg Arg Thr Ala Ala Gly Ile
2405                2410                2415

Met Lys Asn Ala Val Val Asp Gly Ile Val Ala Thr Asp Val Pro
2420                2425                2430

Glu Leu Glu Arg Thr Thr Pro Ile Met Gln Lys Lys Val Gly Gln
2435                2440                2445

Ile Met Leu Ile Leu Val Ser Leu Ala Ala Val Val Val Asn Pro
2450                2455                2460

Ser Val Lys Thr Val Arg Glu Ala Gly Ile Leu Ile Thr Ala Ala
2465                2470                2475

Ala Val Thr Leu Trp Glu Asn Gly Ala Ser Ser Val Trp Asn Ala
2480                2485                2490

Thr Thr Ala Ile Gly Leu Cys His Ile Met Arg Gly Gly Trp Leu
2495                2500                2505

Ser Cys Leu Ser Ile Thr Trp Thr Leu Ile Lys Asn Met Glu Lys
2510                2515                2520

Pro Gly Leu Lys Arg Gly Gly Ala Lys Gly Arg Thr Leu Gly Glu
2525                2530                2535

Val Trp Lys Glu Arg Leu Asn Gln Met Thr Lys Glu Glu Phe Thr
2540                2545                2550

Arg Tyr Arg Lys Glu Ala Ile Ile Glu Val Asp Arg Ser Ala Ala
2555                2560                2565

Lys His Ala Arg Lys Glu Gly Asn Val Thr Gly Gly His Ser Val
2570                2575                2580

Ser Arg Gly Thr Ala Lys Leu Arg Trp Leu Val Glu Arg Arg Phe
2585                2590                2595

Leu Glu Pro Val Gly Lys Val Ile Asp Leu Gly Cys Gly Arg Gly
2600                2605                2610

Gly Trp Cys Tyr Tyr Met Ala Thr Gln Lys Arg Val Gln Glu Val
2615                2620                2625

Arg Gly Tyr Thr Lys Gly Gly Pro Gly His Glu Glu Pro Gln Leu
2630                2635                2640

Val Gln Ser Tyr Gly Trp Asn Ile Val Thr Met Lys Ser Gly Val
```

```
            2645                2650                2655

Asp Val Phe Tyr Arg Pro Ser Glu Cys Cys Asp Thr Leu Leu Cys
    2660                2665                2670

Asp Ile Gly Glu Ser Ser Ser Ala Glu Val Glu Glu His Arg
    2675                2680                2685

Thr Ile Arg Val Leu Glu Met Val Glu Asp Trp Leu His Arg Gly
    2690                2695                2700

Pro Arg Glu Phe Cys Val Lys Val Leu Cys Pro Tyr Met Pro Lys
    2705                2710                2715

Val Ile Glu Lys Met Glu Leu Leu Gln Arg Arg Tyr Gly Gly Gly
    2720                2725                2730

Leu Val Arg Asn Pro Leu Ser Arg Asn Ser Thr His Glu Met Tyr
    2735                2740                2745

Trp Val Ser Arg Ala Ser Gly Asn Val Val His Ser Val Asn Met
    2750                2755                2760

Thr Ser Gln Val Leu Leu Gly Arg Met Glu Lys Arg Thr Trp Lys
    2765                2770                2775

Gly Pro Gln Tyr Glu Glu Asp Val Asn Leu Gly Ser Gly Thr Arg
    2780                2785                2790

Ala Val Gly Lys Pro Leu Leu Asn Ser Asp Thr Ser Lys Ile Asn
    2795                2800                2805

Asn Arg Ile Glu Arg Leu Arg Arg Glu Tyr Ser Ser Thr Trp His
    2810                2815                2820

His Asp Glu Asn His Pro Tyr Arg Thr Trp Asn Tyr His Gly Ser
    2825                2830                2835

Tyr Asp Val Lys Pro Thr Gly Ser Ala Ser Ser Leu Val Asn Gly
    2840                2845                2850

Val Val Arg Leu Leu Ser Lys Pro Trp Asp Thr Ile Thr Asn Val
    2855                2860                2865

Thr Thr Met Ala Met Thr Asp Thr Thr Pro Phe Gly Gln Gln Arg
    2870                2875                2880

Val Phe Lys Glu Lys Val Asp Thr Lys Ala Pro Glu Pro Pro Glu
    2885                2890                2895

Gly Ala Lys Tyr Val Leu Asn Glu Thr Thr Asn Trp Leu Trp Ala
    2900                2905                2910

Phe Leu Ala Arg Glu Lys Arg Pro Arg Met Cys Ser Arg Glu Glu
    2915                2920                2925

Phe Ile Arg Lys Val Asn Ser Asn Ala Ala Leu Gly Ala Met Phe
    2930                2935                2940

Glu Glu Gln Asn Gln Trp Arg Ser Ala Arg Glu Ala Val Glu Asp
    2945                2950                2955

Pro Lys Phe Trp Glu Met Val Asp Glu Glu Arg Glu Ala His Leu
    2960                2965                2970

Arg Gly Glu Cys His Thr Cys Ile Tyr Asn Met Met Gly Lys Arg
    2975                2980                2985

Glu Lys Lys Pro Gly Glu Phe Gly Lys Ala Lys Gly Ser Arg Ala
    2990                2995                3000

Ile Trp Phe Met Trp Leu Gly Ala Arg Phe Leu Glu Phe Glu Ala
    3005                3010                3015

Leu Gly Phe Leu Asn Glu Asp His Trp Leu Gly Arg Lys Asn Ser
    3020                3025                3030

Gly Gly Gly Val Glu Gly Leu Gly Leu Gln Lys Leu Gly Tyr Ile
    3035                3040                3045
```

-continued

```
Leu Arg Glu Val Gly Thr Arg Pro Gly Gly Lys Ile Tyr Ala Asp
3050                3055                3060

Asp Thr Ala Gly Trp Asp Thr Arg Ile Thr Arg Ala Asp Leu Glu
3065                3070                3075

Asn Glu Ala Lys Val Leu Glu Leu Leu Asp Gly Glu His Arg Arg
3080                3085                3090

Leu Ala Arg Ala Ile Ile Glu Leu Thr Tyr Arg His Lys Val Val
3095                3100                3105

Lys Val Met Arg Pro Ala Ala Asp Gly Arg Thr Val Met Asp Val
3110                3115                3120

Ile Ser Arg Glu Asp Gln Arg Gly Ser Gly Gln Val Val Thr Tyr
3125                3130                3135

Ala Leu Asn Thr Phe Thr Asn Leu Ala Val Gln Leu Val Arg Met
3140                3145                3150

Met Glu Gly Glu Gly Val Ile Gly Pro Asp Asp Val Glu Lys Leu
3155                3160                3165

Thr Lys Gly Lys Gly Pro Lys Val Arg Thr Trp Leu Phe Glu Asn
3170                3175                3180

Gly Glu Glu Arg Leu Ser Arg Met Ala Val Ser Gly Asp Asp Cys
3185                3190                3195

Val Val Lys Pro Leu Asp Asp Arg Phe Ala Thr Ser Leu His Phe
3200                3205                3210

Leu Asn Ala Met Ser Lys Val Arg Lys Asp Ile Gln Glu Trp Lys
3215                3220                3225

Pro Ser Thr Gly Trp Tyr Asp Trp Gln Gln Val Pro Phe Cys Ser
3230                3235                3240

Asn His Phe Thr Glu Leu Ile Met Lys Asp Gly Arg Thr Leu Val
3245                3250                3255

Val Pro Cys Arg Gly Gln Asp Glu Leu Val Gly Arg Ala Arg Ile
3260                3265                3270

Ser Pro Gly Ala Gly Trp Asn Val Arg Asp Thr Ala Cys Leu Ala
3275                3280                3285

Lys Ser Tyr Ala Gln Met Trp Leu Leu Leu Tyr Phe His Arg Arg
3290                3295                3300

Asp Leu Arg Leu Met Ala Asn Ala Ile Cys Ser Ala Val Pro Val
3305                3310                3315

Asn Trp Val Pro Thr Gly Arg Thr Thr Trp Ser Ile His Ala Gly
3320                3325                3330

Gly Glu Trp Met Thr Thr Glu Asp Met Leu Glu Val Trp Asn Arg
3335                3340                3345

Val Trp Ile Glu Glu Asn Glu Trp Met Glu Asp Lys Thr Pro Val
3350                3355                3360

Glu Lys Trp Ser Asp Val Pro Tyr Ser Gly Lys Arg Glu Asp Ile
3365                3370                3375

Trp Cys Gly Ser Leu Ile Gly Thr Arg Ala Arg Ala Thr Trp Ala
3380                3385                3390

Glu Asn Ile Gln Val Ala Ile Asn Gln Val Arg Ala Ile Ile Gly
3395                3400                3405

Asp Glu Lys Tyr Val Asp Tyr Met Ser Ser Leu Lys Arg Tyr Glu
3410                3415                3420

Asp Thr Thr Leu Val Glu Asp Thr Val Leu
3425                3430
```

<210> SEQ ID NO 3
<211> LENGTH: 37
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 3
tagcacgaag aattcgatgt ctaagaaacc aggaggg                          37

<210> SEQ ID NO 4
<211> LENGTH: 50
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 4
aagttagccc gggttaatgc tcctacgctg gcgatcaggc caatcaggac            50

<210> SEQ ID NO 5
<211> LENGTH: 28
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 5
agtagttcgc ctgtgtgagc tgacaaac                                    28

<210> SEQ ID NO 6
<211> LENGTH: 29
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 6
agatcctgtg ttctcgcacc accagccac                                   29

<210> SEQ ID NO 7
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 7
ggatggatgc twggkagcaa c                                           21

<210> SEQ ID NO 8
<211> LENGTH: 19
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 8
ccatccaagc ctccacatc                                              19

<210> SEQ ID NO 9
<211> LENGTH: 30
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 9
tggatgggat ccaatatgcg tgataggtcc                                                    30

<210> SEQ ID NO 10
<211> LENGTH: 39
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 10
aaaagggtca atggtaccag cattttaagc attcacgtt                                          39

<210> SEQ ID NO 11
<211> LENGTH: 36
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 11
tagcacgaag aattcgatgt ctaaaaacca ggaggg                                             36

<210> SEQ ID NO 12
<211> LENGTH: 3433
<212> TYPE: PRT
<213> ORGANISM: West Nile virus strain NY99-flamingo382-99

<400> SEQUENCE: 12

Met Ser Lys Lys Pro Gly Gly Pro Gly Lys Ser Arg Ala Val Asn Met
1               5                   10                  15

Leu Lys Arg Gly Met Pro Arg Val Leu Ser Leu Ile Gly Leu Lys Arg
            20                  25                  30

Ala Met Leu Ser Leu Ile Asp Gly Lys Gly Pro Ile Arg Phe Val Leu
        35                  40                  45

Ala Leu Leu Ala Phe Phe Arg Phe Thr Ala Ile Ala Pro Thr Arg Ala
    50                  55                  60

Val Leu Asp Arg Trp Arg Gly Val Asn Lys Gln Thr Ala Met Lys His
65                  70                  75                  80

Leu Leu Ser Phe Lys Lys Glu Leu Gly Thr Leu Thr Ser Ala Ile Asn
                85                  90                  95

Arg Arg Ser Ser Lys Gln Lys Lys Arg Gly Gly Lys Thr Gly Ile Ala
            100                 105                 110

Val Met Ile Gly Leu Ile Ala Ser Val Gly Ala Val Thr Leu Ser Asn
        115                 120                 125

Phe Gln Gly Lys Val Met Met Thr Val Asn Ala Thr Asp Val Thr Asp
    130                 135                 140

Val Ile Thr Ile Pro Thr Ala Ala Gly Lys Asn Leu Cys Ile Val Arg
145                 150                 155                 160

Ala Met Asp Val Gly Tyr Met Cys Asp Asp Thr Ile Thr Tyr Glu Cys
                165                 170                 175

Pro Val Leu Ser Ala Gly Asn Asp Pro Glu Asp Ile Asp Cys Trp Cys
            180                 185                 190

Thr Lys Ser Ala Val Tyr Val Arg Tyr Gly Arg Cys Thr Lys Thr Arg
        195                 200                 205

His Ser Arg Arg Ser Arg Arg Ser Leu Thr Val Gln Thr His Gly Glu
    210                 215                 220

-continued

```
Ser Thr Leu Ala Asn Lys Lys Gly Ala Trp Met Asp Ser Thr Lys Ala
225                 230                 235                 240

Thr Arg Tyr Leu Val Lys Thr Glu Ser Trp Ile Leu Arg Asn Pro Gly
            245                 250                 255

Tyr Ala Leu Val Ala Ala Val Ile Gly Trp Met Leu Gly Ser Asn Thr
        260                 265                 270

Met Gln Arg Val Val Phe Val Leu Leu Leu Val Ala Pro Ala
    275                 280                 285

Tyr Ser Phe Asn Cys Leu Gly Met Ser Asn Arg Asp Phe Leu Glu Gly
290                 295                 300

Val Ser Gly Ala Thr Trp Val Asp Leu Val Leu Glu Gly Asp Ser Cys
305                 310                 315                 320

Val Thr Ile Met Ser Lys Asp Lys Pro Thr Ile Asp Val Lys Met Met
                325                 330                 335

Asn Met Glu Ala Ala Asn Leu Ala Glu Val Arg Ser Tyr Cys Tyr Leu
                340                 345                 350

Ala Thr Val Ser Asp Leu Ser Thr Lys Ala Ala Cys Pro Thr Met Gly
        355                 360                 365

Glu Ala His Asn Asp Lys Arg Ala Asp Pro Ala Phe Val Cys Arg Gln
370                 375                 380

Gly Val Val Asp Arg Gly Trp Gly Asn Gly Cys Gly Leu Phe Gly Lys
385                 390                 395                 400

Gly Ser Ile Asp Thr Cys Ala Lys Phe Ala Cys Ser Thr Lys Ala Ile
                405                 410                 415

Gly Arg Thr Ile Leu Lys Glu Asn Ile Lys Tyr Glu Val Ala Ile Phe
                420                 425                 430

Val His Gly Pro Thr Thr Val Glu Ser His Gly Asn Tyr Ser Thr Gln
        435                 440                 445

Val Gly Ala Thr Gln Ala Gly Arg Phe Ser Ile Thr Pro Ala Ala Pro
    450                 455                 460

Ser Tyr Thr Leu Lys Leu Gly Glu Tyr Gly Glu Val Thr Val Asp Cys
465                 470                 475                 480

Glu Pro Arg Ser Gly Ile Asp Thr Asn Ala Tyr Tyr Val Met Thr Val
                485                 490                 495

Gly Thr Lys Thr Phe Leu Val His Arg Glu Trp Phe Met Asp Leu Asn
                500                 505                 510

Leu Pro Trp Ser Ser Ala Gly Ser Thr Val Trp Arg Asn Arg Glu Thr
        515                 520                 525

Leu Met Glu Phe Glu Glu Pro His Ala Thr Lys Gln Ser Val Ile Ala
530                 535                 540

Leu Gly Ser Gln Glu Gly Ala Leu His Gln Ala Leu Ala Gly Ala Ile
545                 550                 555                 560

Pro Val Glu Phe Ser Ser Asn Thr Val Lys Leu Thr Ser Gly His Leu
                565                 570                 575

Lys Cys Arg Val Lys Met Glu Lys Leu Gln Leu Lys Gly Thr Thr Tyr
                580                 585                 590

Gly Val Cys Ser Lys Ala Phe Lys Phe Leu Gly Thr Pro Ala Asp Thr
        595                 600                 605

Gly His Gly Thr Val Val Leu Glu Leu Gln Tyr Thr Gly Thr Asp Gly
    610                 615                 620

Pro Cys Lys Val Pro Ile Ser Ser Val Ala Ser Leu Asn Asp Leu Thr
625                 630                 635                 640

Pro Val Gly Arg Leu Val Thr Val Asn Pro Phe Val Ser Val Ala Thr
```

```
                    645                 650                 655
Ala Asn Ala Lys Val Leu Ile Glu Leu Glu Pro Pro Phe Gly Asp Ser
                660                 665                 670

Tyr Ile Val Val Gly Arg Gly Glu Gln Ile Asn His His Trp His
            675                 680                 685

Lys Ser Gly Ser Ser Ile Gly Lys Ala Phe Thr Thr Thr Leu Lys Gly
        690                 695                 700

Ala Gln Arg Leu Ala Ala Leu Gly Asp Thr Ala Trp Asp Phe Gly Ser
705                 710                 715                 720

Val Gly Gly Val Phe Thr Ser Val Gly Lys Ala Val His Gln Val Phe
                725                 730                 735

Gly Gly Ala Phe Arg Ser Leu Phe Gly Gly Met Ser Trp Ile Thr Gln
                740                 745                 750

Gly Leu Leu Gly Ala Leu Leu Leu Trp Met Gly Ile Asn Ala Arg Asp
            755                 760                 765

Arg Ser Ile Ala Leu Thr Phe Leu Ala Val Gly Gly Val Leu Leu Phe
        770                 775                 780

Leu Ser Val Asn Val His Ala Asp Thr Gly Cys Ala Ile Asp Ile Ser
785                 790                 795                 800

Arg Gln Glu Leu Arg Cys Gly Ser Gly Val Phe Ile His Asn Asp Val
                805                 810                 815

Glu Ala Trp Met Asp Arg Tyr Lys Tyr Tyr Pro Glu Thr Pro Gln Gly
                820                 825                 830

Leu Ala Lys Ile Ile Gln Lys Ala His Lys Glu Gly Val Cys Gly Leu
            835                 840                 845

Arg Ser Val Ser Arg Leu Glu His Gln Met Trp Glu Ala Val Lys Asp
        850                 855                 860

Glu Leu Asn Thr Leu Leu Lys Glu Asn Gly Val Asp Leu Ser Val Val
865                 870                 875                 880

Val Glu Lys Gln Glu Gly Met Tyr Lys Ser Ala Pro Lys Arg Leu Thr
                885                 890                 895

Ala Thr Thr Glu Lys Leu Glu Ile Gly Trp Lys Ala Trp Gly Lys Ser
            900                 905                 910

Ile Leu Phe Ala Pro Glu Leu Ala Asn Asn Thr Phe Val Val Asp Gly
        915                 920                 925

Pro Glu Thr Lys Glu Cys Pro Thr Gln Asn Arg Ala Trp Asn Ser Leu
930                 935                 940

Glu Val Glu Asp Phe Gly Phe Gly Leu Thr Ser Thr Arg Met Phe Leu
945                 950                 955                 960

Lys Val Arg Glu Ser Asn Thr Thr Glu Cys Asp Ser Lys Ile Ile Gly
                965                 970                 975

Thr Ala Val Lys Asn Asn Leu Ala Ile His Ser Asp Leu Ser Tyr Trp
            980                 985                 990

Ile Glu Ser Arg Leu Asn Asp Thr Trp Lys Leu Glu Arg Ala Val Leu
        995                 1000                1005

Gly Glu Val Lys Ser Cys Thr Trp Pro Glu Thr His Thr Leu Trp
        1010                1015                1020

Gly Asp Gly Ile Leu Glu Ser Asp Leu Ile Ile Pro Val Thr Leu
        1025                1030                1035

Ala Gly Pro Arg Ser Asn His Asn Arg Arg Pro Gly Tyr Lys Thr
        1040                1045                1050

Gln Asn Gln Gly Pro Trp Asp Glu Gly Arg Val Glu Ile Asp Phe
        1055                1060                1065
```

-continued

```
Asp Tyr Cys Pro Gly Thr Thr Val Thr Leu Ser Glu Ser Cys Gly
    1070                1075                1080

His Arg Gly Pro Ala Thr Arg Thr Thr Thr Glu Ser Gly Lys Leu
    1085                1090                1095

Ile Thr Asp Trp Cys Cys Arg Ser Cys Thr Leu Pro Pro Leu Arg
    1100                1105                1110

Tyr Gln Thr Asp Ser Gly Cys Trp Tyr Gly Met Glu Ile Arg Pro
    1115                1120                1125

Gln Arg His Asp Glu Lys Thr Leu Val Gln Ser Gln Val Asn Ala
    1130                1135                1140

Tyr Asn Ala Asp Met Ile Asp Pro Phe Gln Leu Gly Leu Leu Val
    1145                1150                1155

Val Phe Leu Ala Thr Gln Glu Val Leu Arg Lys Arg Trp Thr Ala
    1160                1165                1170

Lys Ile Ser Met Pro Ala Ile Leu Ile Ala Leu Leu Val Leu Val
    1175                1180                1185

Phe Gly Gly Ile Thr Tyr Thr Asp Val Leu Arg Tyr Val Ile Leu
    1190                1195                1200

Val Gly Ala Ala Phe Ala Glu Ser Asn Ser Gly Gly Asp Val Val
    1205                1210                1215

His Leu Ala Leu Met Ala Thr Phe Lys Ile Gln Pro Val Phe Met
    1220                1225                1230

Val Ala Ser Phe Leu Lys Ala Arg Trp Thr Asn Gln Glu Asn Ile
    1235                1240                1245

Leu Leu Met Leu Ala Ala Val Phe Phe Gln Met Ala Tyr His Asp
    1250                1255                1260

Ala Arg Gln Ile Leu Leu Trp Glu Ile Pro Asp Val Leu Asn Ser
    1265                1270                1275

Leu Ala Val Ala Trp Met Ile Leu Arg Ala Ile Thr Phe Thr Thr
    1280                1285                1290

Thr Ser Asn Val Val Val Pro Leu Leu Ala Leu Leu Thr Pro Gly
    1295                1300                1305

Leu Arg Cys Leu Asn Leu Asp Val Tyr Arg Ile Leu Leu Leu Met
    1310                1315                1320

Val Gly Ile Gly Ser Leu Ile Arg Glu Lys Arg Ser Ala Ala Ala
    1325                1330                1335

Lys Lys Lys Gly Ala Ser Leu Leu Cys Leu Ala Leu Ala Ser Thr
    1340                1345                1350

Gly Leu Phe Asn Pro Met Ile Leu Ala Ala Gly Leu Ile Ala Cys
    1355                1360                1365

Asp Pro Asn Arg Lys Arg Gly Trp Pro Ala Thr Glu Val Met Thr
    1370                1375                1380

Ala Val Gly Leu Met Phe Ala Ile Val Gly Gly Leu Ala Glu Leu
    1385                1390                1395

Asp Ile Asp Ser Met Ala Ile Pro Met Thr Ile Ala Gly Leu Met
    1400                1405                1410

Phe Ala Ala Phe Val Ile Ser Gly Lys Ser Thr Asp Met Trp Ile
    1415                1420                1425

Glu Arg Thr Ala Asp Ile Ser Trp Glu Ser Asp Ala Glu Ile Thr
    1430                1435                1440

Gly Ser Ser Glu Arg Val Asp Val Arg Leu Asp Asp Asp Gly Asn
    1445                1450                1455
```

```
Phe Gln Leu Met Asn Asp Pro Gly Ala Pro Trp Lys Ile Trp Met
    1460                1465                1470

Leu Arg Met Val Cys Leu Ala Ile Ser Ala Tyr Thr Pro Trp Ala
    1475                1480                1485

Ile Leu Pro Ser Val Val Gly Phe Trp Ile Thr Leu Gln Tyr Thr
    1490                1495                1500

Lys Arg Gly Gly Val Leu Trp Asp Thr Pro Ser Pro Lys Glu Tyr
    1505                1510                1515

Lys Lys Gly Asp Thr Thr Thr Gly Val Tyr Arg Ile Met Thr Arg
    1520                1525                1530

Gly Leu Leu Gly Ser Tyr Gln Ala Gly Ala Gly Val Met Val Glu
    1535                1540                1545

Gly Val Phe His Thr Leu Trp His Thr Thr Lys Gly Ala Ala Leu
    1550                1555                1560

Met Ser Gly Glu Gly Arg Leu Asp Pro Tyr Trp Gly Ser Val Lys
    1565                1570                1575

Glu Asp Arg Leu Cys Tyr Gly Gly Pro Trp Lys Leu Gln His Lys
    1580                1585                1590

Trp Asn Gly Gln Asp Glu Val Gln Met Ile Val Val Glu Pro Gly
    1595                1600                1605

Lys Asn Val Lys Asn Val Gln Thr Lys Pro Gly Val Phe Lys Thr
    1610                1615                1620

Pro Glu Gly Glu Ile Gly Ala Val Thr Leu Asp Phe Pro Thr Gly
    1625                1630                1635

Thr Ser Gly Ser Pro Ile Val Asp Lys Asn Gly Asp Val Ile Gly
    1640                1645                1650

Leu Tyr Gly Asn Gly Val Ile Met Pro Asn Gly Ser Tyr Ile Ser
    1655                1660                1665

Ala Ile Val Gln Gly Glu Arg Met Asp Glu Pro Ile Pro Ala Gly
    1670                1675                1680

Phe Glu Pro Glu Met Leu Arg Lys Lys Gln Ile Thr Val Leu Asp
    1685                1690                1695

Leu His Pro Gly Ala Gly Lys Thr Arg Arg Ile Leu Pro Gln Ile
    1700                1705                1710

Ile Lys Glu Ala Ile Asn Arg Arg Leu Arg Thr Ala Val Leu Ala
    1715                1720                1725

Pro Thr Arg Val Val Ala Ala Glu Met Ala Glu Ala Leu Arg Gly
    1730                1735                1740

Leu Pro Ile Arg Tyr Gln Thr Ser Ala Val Pro Arg Glu His Asn
    1745                1750                1755

Gly Asn Glu Ile Val Asp Val Met Cys His Ala Thr Leu Thr His
    1760                1765                1770

Arg Leu Met Ser Pro His Arg Val Pro Asn Tyr Asn Leu Phe Val
    1775                1780                1785

Met Asp Glu Ala His Phe Thr Asp Pro Ala Ser Ile Ala Ala Arg
    1790                1795                1800

Gly Tyr Ile Ser Thr Lys Val Glu Leu Gly Glu Ala Ala Ala Ile
    1805                1810                1815

Phe Met Thr Ala Thr Pro Pro Gly Thr Ser Asp Pro Phe Pro Glu
    1820                1825                1830

Ser Asn Ser Pro Ile Ser Asp Leu Gln Thr Glu Ile Pro Asp Arg
    1835                1840                1845

Ala Trp Asn Ser Gly Tyr Glu Trp Ile Thr Glu Tyr Thr Gly Lys
```

-continued

```
                1850                1855                1860
Thr Val Trp Phe Val Pro Ser Val Lys Met Gly Asn Glu Ile Ala
        1865                1870                1875
Leu Cys Leu Gln Arg Ala Gly Lys Lys Val Val Gln Leu Asn Arg
        1880                1885                1890
Lys Ser Tyr Glu Thr Glu Tyr Pro Lys Cys Lys Asn Asp Asp Trp
        1895                1900                1905
Asp Phe Val Ile Thr Thr Asp Ile Ser Glu Met Gly Ala Asn Phe
        1910                1915                1920
Lys Ala Ser Arg Val Ile Asp Ser Arg Lys Ser Val Lys Pro Thr
        1925                1930                1935
Ile Ile Thr Glu Gly Glu Gly Arg Val Ile Leu Gly Glu Pro Ser
        1940                1945                1950
Ala Val Thr Ala Ala Ser Ala Ala Gln Arg Arg Gly Arg Ile Gly
        1955                1960                1965
Arg Asn Pro Ser Gln Val Gly Asp Glu Tyr Cys Tyr Gly Gly His
        1970                1975                1980
Thr Asn Glu Asp Asp Ser Asn Phe Ala His Trp Thr Glu Ala Arg
        1985                1990                1995
Ile Met Leu Asp Asn Ile Asn Met Pro Asn Gly Leu Ile Ala Gln
        2000                2005                2010
Phe Tyr Gln Pro Glu Arg Glu Lys Val Tyr Thr Met Asp Gly Glu
        2015                2020                2025
Tyr Arg Leu Arg Gly Glu Arg Lys Asn Phe Leu Glu Leu Leu
        2030                2035                2040
Arg Thr Ala Asp Leu Pro Val Trp Leu Ala Tyr Lys Val Ala Ala
        2045                2050                2055
Ala Gly Val Ser Tyr His Asp Arg Arg Trp Cys Phe Asp Gly Pro
        2060                2065                2070
Arg Thr Asn Thr Ile Leu Glu Asp Asn Asn Glu Val Glu Val Ile
        2075                2080                2085
Thr Lys Leu Gly Glu Arg Lys Ile Leu Arg Pro Arg Trp Ile Asp
        2090                2095                2100
Ala Arg Val Tyr Ser Asp His Gln Ala Leu Lys Ala Phe Lys Asp
        2105                2110                2115
Phe Ala Ser Gly Lys Arg Ser Gln Ile Gly Leu Ile Glu Val Leu
        2120                2125                2130
Gly Lys Met Pro Glu His Phe Met Gly Lys Thr Trp Glu Ala Leu
        2135                2140                2145
Asp Thr Met Tyr Val Val Ala Thr Ala Glu Lys Gly Gly Arg Ala
        2150                2155                2160
His Arg Met Ala Leu Glu Glu Leu Pro Asp Ala Leu Gln Thr Ile
        2165                2170                2175
Ala Leu Ile Ala Leu Leu Ser Val Met Thr Met Gly Val Phe Phe
        2180                2185                2190
Leu Leu Met Gln Arg Lys Gly Ile Gly Lys Ile Gly Leu Gly Gly
        2195                2200                2205
Ala Val Leu Gly Val Ala Thr Phe Phe Cys Trp Met Ala Glu Val
        2210                2215                2220
Pro Gly Thr Lys Ile Ala Gly Met Leu Leu Leu Ser Leu Leu Leu
        2225                2230                2235
Met Ile Val Leu Ile Pro Glu Pro Glu Lys Gln Arg Ser Gln Thr
        2240                2245                2250
```

```
Asp Asn Gln Leu Ala Val Phe Leu Ile Cys Val Met Thr Leu Val
    2255                2260                2265

Ser Ala Val Ala Ala Asn Glu Met Gly Trp Leu Asp Lys Thr Lys
    2270                2275                2280

Ser Asp Ile Ser Ser Leu Phe Gly Gln Arg Ile Glu Val Lys Glu
    2285                2290                2295

Asn Phe Ser Met Gly Glu Phe Leu Leu Asp Leu Arg Pro Ala Thr
    2300                2305                2310

Ala Trp Ser Leu Tyr Ala Val Thr Thr Ala Val Leu Thr Pro Leu
    2315                2320                2325

Leu Lys His Leu Ile Thr Ser Asp Tyr Ile Asn Thr Ser Leu Thr
    2330                2335                2340

Ser Ile Asn Val Gln Ala Ser Ala Leu Phe Thr Leu Ala Arg Gly
    2345                2350                2355

Phe Pro Phe Val Asp Val Gly Val Ser Ala Leu Leu Leu Ala Ala
    2360                2365                2370

Gly Cys Trp Gly Gln Val Thr Leu Thr Val Thr Val Thr Ala Ala
    2375                2380                2385

Thr Leu Leu Phe Cys His Tyr Ala Tyr Met Val Pro Gly Trp Gln
    2390                2395                2400

Ala Glu Ala Met Arg Ser Ala Gln Arg Arg Thr Ala Ala Gly Ile
    2405                2410                2415

Met Lys Asn Ala Val Val Asp Gly Ile Val Ala Thr Asp Val Pro
    2420                2425                2430

Glu Leu Glu Arg Thr Thr Pro Ile Met Gln Lys Lys Val Gly Gln
    2435                2440                2445

Ile Met Leu Ile Leu Val Ser Leu Ala Ala Val Val Val Asn Pro
    2450                2455                2460

Ser Val Lys Thr Val Arg Glu Ala Gly Ile Leu Ile Thr Ala Ala
    2465                2470                2475

Ala Val Thr Leu Trp Glu Asn Gly Ala Ser Ser Val Trp Asn Ala
    2480                2485                2490

Thr Thr Ala Ile Gly Leu Cys His Ile Met Arg Gly Gly Trp Leu
    2495                2500                2505

Ser Cys Leu Ser Ile Thr Trp Thr Leu Ile Lys Asn Met Glu Lys
    2510                2515                2520

Pro Gly Leu Lys Arg Gly Gly Ala Lys Gly Arg Thr Leu Gly Glu
    2525                2530                2535

Val Trp Lys Glu Arg Leu Asn Gln Met Thr Lys Glu Glu Phe Thr
    2540                2545                2550

Arg Tyr Arg Lys Glu Ala Ile Ile Glu Val Asp Arg Ser Ala Ala
    2555                2560                2565

Lys His Ala Arg Lys Glu Gly Asn Val Thr Gly Gly His Pro Val
    2570                2575                2580

Ser Arg Gly Thr Ala Lys Leu Arg Trp Leu Val Glu Arg Arg Phe
    2585                2590                2595

Leu Glu Pro Val Gly Lys Val Ile Asp Leu Gly Cys Gly Arg Gly
    2600                2605                2610

Gly Trp Cys Tyr Tyr Met Ala Thr Gln Lys Arg Val Gln Glu Val
    2615                2620                2625

Arg Gly Tyr Thr Lys Gly Gly Pro Gly His Glu Glu Pro Gln Leu
    2630                2635                2640
```

```
Val Gln Ser Tyr Gly Trp Asn Ile Val Thr Met Lys Ser Gly Val
2645                2650                2655

Asp Val Phe Tyr Arg Pro Ser Glu Cys Cys Asp Thr Leu Leu Cys
2660                2665                2670

Asp Ile Gly Glu Ser Ser Ser Ala Glu Val Glu Glu His Arg
2675                2680                2685

Thr Ile Arg Val Leu Glu Met Val Glu Asp Trp Leu His Arg Gly
2690                2695                2700

Pro Arg Glu Phe Cys Val Lys Val Leu Cys Pro Tyr Met Pro Lys
2705                2710                2715

Val Ile Glu Lys Met Glu Leu Leu Gln Arg Arg Tyr Gly Gly Gly
2720                2725                2730

Leu Val Arg Asn Pro Leu Ser Arg Asn Ser Thr His Glu Met Tyr
2735                2740                2745

Trp Val Ser Arg Ala Ser Gly Asn Val Val His Ser Val Asn Met
2750                2755                2760

Thr Ser Gln Val Leu Leu Gly Arg Met Glu Lys Arg Thr Trp Lys
2765                2770                2775

Gly Pro Gln Tyr Glu Glu Asp Val Asn Leu Gly Ser Gly Thr Arg
2780                2785                2790

Ala Val Gly Lys Pro Leu Leu Asn Ser Asp Thr Ser Lys Ile Lys
2795                2800                2805

Asn Arg Ile Glu Arg Leu Arg Arg Glu Tyr Ser Ser Thr Trp His
2810                2815                2820

His Asp Glu Asn His Pro Tyr Arg Thr Trp Asn Tyr His Gly Ser
2825                2830                2835

Tyr Asp Val Lys Pro Thr Gly Ser Ala Ser Ser Leu Val Asn Gly
2840                2845                2850

Val Val Arg Leu Leu Ser Lys Pro Trp Asp Thr Ile Thr Asn Val
2855                2860                2865

Thr Thr Met Ala Met Thr Asp Thr Thr Pro Phe Gly Gln Gln Arg
2870                2875                2880

Val Phe Lys Glu Lys Val Asp Thr Lys Ala Pro Glu Pro Pro Glu
2885                2890                2895

Gly Val Lys Tyr Val Leu Asn Glu Thr Thr Asn Trp Leu Trp Ala
2900                2905                2910

Phe Leu Ala Arg Glu Lys Arg Pro Arg Met Cys Ser Arg Glu Glu
2915                2920                2925

Phe Ile Arg Lys Val Asn Ser Asn Ala Ala Leu Gly Ala Met Phe
2930                2935                2940

Glu Glu Gln Asn Gln Trp Arg Ser Ala Arg Glu Ala Val Glu Asp
2945                2950                2955

Pro Lys Phe Trp Glu Met Val Asp Glu Glu Arg Glu Ala His Leu
2960                2965                2970

Arg Gly Glu Cys His Thr Cys Ile Tyr Asn Met Met Gly Lys Arg
2975                2980                2985

Glu Lys Lys Pro Gly Glu Phe Gly Lys Ala Lys Gly Ser Arg Ala
2990                2995                3000

Ile Trp Phe Met Trp Leu Gly Ala Arg Phe Leu Glu Phe Glu Ala
3005                3010                3015

Leu Gly Phe Leu Asn Glu Asp His Trp Leu Gly Arg Lys Asn Ser
3020                3025                3030

Gly Gly Gly Val Glu Gly Leu Gly Leu Gln Lys Leu Gly Tyr Ile
```

-continued

```
            3035                3040                3045
Leu Arg Glu Val Gly Thr Arg Pro Gly Gly Lys Ile Tyr Ala Asp
    3050                3055                3060

Asp Thr Ala Gly Trp Asp Thr Arg Ile Thr Arg Ala Asp Leu Glu
    3065                3070                3075

Asn Glu Ala Lys Val Leu Glu Leu Leu Asp Gly Glu His Arg Arg
    3080                3085                3090

Leu Ala Arg Ala Ile Ile Glu Leu Thr Tyr Arg His Lys Val Val
    3095                3100                3105

Lys Val Met Arg Pro Ala Ala Asp Gly Arg Thr Val Met Asp Val
    3110                3115                3120

Ile Ser Arg Glu Asp Gln Arg Gly Ser Gly Gln Val Val Thr Tyr
    3125                3130                3135

Ala Leu Asn Thr Phe Thr Asn Leu Ala Val Gln Leu Val Arg Met
    3140                3145                3150

Met Glu Gly Glu Gly Val Ile Gly Pro Asp Asp Val Glu Lys Leu
    3155                3160                3165

Thr Lys Gly Lys Gly Pro Lys Val Arg Thr Trp Leu Phe Glu Asn
    3170                3175                3180

Gly Glu Glu Arg Leu Ser Arg Met Ala Val Ser Gly Asp Asp Cys
    3185                3190                3195

Val Val Lys Pro Leu Asp Asp Arg Phe Ala Thr Ser Leu His Phe
    3200                3205                3210

Leu Asn Ala Met Ser Lys Val Arg Lys Asp Ile Gln Glu Trp Lys
    3215                3220                3225

Pro Ser Thr Gly Trp Tyr Asp Trp Gln Gln Val Pro Phe Cys Ser
    3230                3235                3240

Asn His Phe Thr Glu Leu Ile Met Lys Asp Gly Arg Thr Leu Val
    3245                3250                3255

Val Pro Cys Arg Gly Gln Asp Glu Leu Val Gly Arg Ala Arg Ile
    3260                3265                3270

Ser Pro Gly Ala Gly Trp Asn Val Arg Asp Thr Ala Cys Leu Ala
    3275                3280                3285

Lys Ser Tyr Ala Gln Met Trp Leu Leu Leu Tyr Phe His Arg Arg
    3290                3295                3300

Asp Leu Arg Leu Met Ala Asn Ala Ile Cys Ser Ala Val Pro Val
    3305                3310                3315

Asn Trp Val Pro Thr Gly Arg Thr Thr Trp Ser Ile His Ala Gly
    3320                3325                3330

Gly Glu Trp Met Thr Thr Glu Asp Met Leu Glu Val Trp Asn Arg
    3335                3340                3345

Val Trp Ile Glu Glu Asn Glu Trp Met Glu Asp Lys Thr Pro Val
    3350                3355                3360

Glu Lys Trp Ser Asp Val Pro Tyr Ser Gly Lys Arg Glu Asp Ile
    3365                3370                3375

Trp Cys Gly Ser Leu Ile Gly Thr Arg Ala Arg Ala Thr Trp Ala
    3380                3385                3390

Glu Asn Ile Gln Val Ala Ile Asn Gln Val Arg Ala Ile Ile Gly
    3395                3400                3405

Asp Glu Lys Tyr Val Asp Tyr Met Ser Ser Leu Lys Arg Tyr Glu
    3410                3415                3420
```

```
Asp Thr  Thr Leu Val Glu Asp  Thr Val Leu
    3425                3430
```

UNITED STATES PATENT AND TRADEMARK OFFICE
CERTIFICATE OF CORRECTION

PATENT NO.        : 9,657,276 B2  
APPLICATION NO.   : 14/230776  
DATED             : May 23, 2017  
INVENTOR(S)       : Philippe Despres et al.

Page 1 of 1

It is certified that error appears in the above-identified patent and that said Letters Patent is hereby corrected as shown below:

On the Title Page

Item (75), "Despres Philippe" should read --Philippe Despres--

Signed and Sealed this
Fourteenth Day of August, 2018

Andrei Iancu
*Director of the United States Patent and Trademark Office*